(12) United States Patent
Haupts et al.

(10) Patent No.: US 7,335,504 B2
(45) Date of Patent: Feb. 26, 2008

(54) ENGINEERED ENZYMES AND USES THEREOF

(75) Inventors: Ulrich Haupts, Köln (DE); Andre Koltermann, Köln (DE); Andreas Scheidig, Köln (DE); Christian Votsmeier, Köln (DE); Ulrich Kettling, Köln (DE)

(73) Assignee: DIREVO Biotechnology AG, Nattermannallee 1, Cologne (DE)

( * ) Notice: Subject to any disclaimer, the term of this patent is extended or adjusted under 35 U.S.C. 154(b) by 0 days.

(21) Appl. No.: 10/872,197

(22) Filed: Jun. 18, 2004

(65) Prior Publication Data

US 2005/0059126 A1    Mar. 17, 2005

Related U.S. Application Data

(60) Provisional application No. 60/524,960, filed on Nov. 25, 2003.

(30) Foreign Application Priority Data

| Jun. 18, 2003 | (EP) | ................................. | 03013819 |
| Nov. 10, 2003 | (EP) | ................................. | 03025851 |
| Nov. 11, 2003 | (EP) | ................................. | 03025871 |

(51) Int. Cl.
*C12N 9/64* (2006.01)
*G01N 33/567* (2006.01)
*C12Q 1/37* (2006.01)
*C12P 21/06* (2006.01)
*C12P 21/04* (2006.01)

(52) U.S. Cl. ...................... 435/226; 435/7.72; 435/23; 435/69.1; 435/70.1; 435/71.1

(58) Field of Classification Search ..................... None
See application file for complete search history.

(56) References Cited

U.S. PATENT DOCUMENTS 5,258,289 A    11/1993 Davis et al. ............... 435/69.6

FOREIGN PATENT DOCUMENTS

| EP | 1 361 284 | 5/2002 |
| EP | 1 321 513 | 6/2003 |
| WO | WO 92/18645 | 10/1992 |
| WO | WO 95/22625 | 8/1995 |
| WO | WO 96/21009 | 7/1996 |
| WO | WO 96/27671 | 9/1996 |
| WO | WO 98/11237 | 3/1998 |
| WO | WO 98/42728 | 10/1998 |
| WO | WO 02/31177 | 4/2000 |
| WO | WO 01/24933 | 4/2001 |
| WO | WO 01/34835 | 5/2001 |
| WO | WO 01/42432 | * 6/2001 |
| WO | WO 02/12543 | 2/2002 |
| WO | WO 02/090300 A2 | 11/2002 |
| WO | WO 03/095670 | 11/2003 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Hedstrom et al, Converting trypsin to chymotrypsin: residue 172 is a substrate specificity determinant. Biochemistry. Jul. 26, 1994;33(29):8757-63.*
Horrevoets et al, Thrombin-variable region 1 (VR1). Evidence for the dominant contribution of VR1 of serine proteases to their interaction with plasminogen activator inhibitor 1. J Biol Chem. Jan. 15, 1993;268(2):779-82.*
Lesk et al, Conservation and variability in the structures of serine proteinases of the chymotrypsin family. J Mol Biol. May 10, 1996;258(3):501-37.*
Kurth et al, Converting trypsin to chymotrypsin: structural determinants of S1' specificity. Biochemistry. Aug. 19, 1997;36(33):10098-104.*
Barrett et al, Introduction: family of S1 trypsin (clan SA). In: Handbook of Proteolytic Enzymes. Academic Press 1998 pp. 5-12.*
Tatiana et al, (1999), "Blast 2 sequences—a new tool for comparing protein and nucleotide sequences", FEMS Microbiol Lett. 174:247-250.*
BLAST alignment of SEQ ID No. 1 with thrombin and endopeptidase.*
BLAST alignment of SEQ ID No. 1 with complement component C2.*
Haupts et al, Single-molecule detection technologies in miniaturized high-throughput screening: fluorescence intensity distribution analysis. J Biomol Screen. Feb. 2003;8(1):19-33.*
Aguilar et al. "Comparisons of the three-dimensional structures, specificities and glycosylation of renins, yeast proteinase A and cathepsin D." Adv Exp Med Biol. 1995;362:155-66.
Almeida, R. et al. "Complementary DNA sequence of human neutrophil azurocidin, an antibiotic with extensive homology to serine proteases." Biochem Biophys Res Commun. Jun. 14, 1991;177(2):688-95.
Altamirano et al. "Directed evolution of new catalytic activity using the α/β-barrel scaffold." Nature. Feb. 10, 2000;403(6770):617-22.
Altschul et al. "Basic local alignment search tool." J Mol Biol. Oct. 5, 1990;215(3):403-10.
Arcoleo, J. & Greer, J.; "Hemoglobin binding site and its relationship to the serine protease-like active site of haptoglobin." J Biol Chem. Sep. 10, 1982;257(17):10063-8.
Ballinger, M et al. "Furilisin: a variant of subtilisin BPN' engineered for cleaving tribasic substrates." Biochemistry. Oct. 22, 1996;35(42):13579-85.
Bedford & Schulze, "Exogensous enzymes for pigs and poultry" Nutrition Research Reviews 1998:91-114.
Bergeron, F. et al. << Subtilase-like pro-protein convertases: from molecular specificity to therapeutic applications. J Mol Endocrinol. Feb. 2000;24(1):1-22.
Berman et al. "The Protein Data Bank." Nucleic Acids Res. Jan. 1, 2000;28(1):235-42.

(Continued)

Primary Examiner—Sheridan Swope
(74) Attorney, Agent, or Firm—Needle & Rosenberg P.C.

(57) ABSTRACT

The present invention provides engineered enzymes generated from protein scaffolds combined with Specificity Determining Regions, the production thereof and the use of said engineered enzymes for research, nutritional care, personal care and industrial purposes.

29 Claims, 18 Drawing Sheets

OTHER PUBLICATIONS

Cadwell and Joyce, "Randomization of genes by PCR mutagenesis." PCR Methods Appl. Aug. 1992;2(1):28-33.

Chitpinityol & Crabbe, "Chymosin and aspartic proteinases"(1998), *Food Chemistry*, 61(4), 395-418.

Coombs et al. "Distinct mechanisms contribute to stringent substrate specificity of tissue-type plasminogen activator." J Biol Chem. Feb. 23, 1996;271(8):4461-7.

Corey and Corey, "On the failure of de novo-designed peptides as biocatalysts." Proc Natl Acad Sci U S A. Oct. 15, 1996;93(21):11428-34.

Ding, L et al. "Origins of the specificity of tissue-type plasminogen activator." Proc Natl Acad Sci U S A. Aug. 15, 1995;92(17):7627-31.

Fersh, "Dissection of the structure and activity of the tyrosoyl-tRNA synthetase by site-directed mutagenesis," Biochemistry Dec. 15, 1987; 26(25):8031-6.

Fischer and Pleiss, "The lipase engineering database: a navigation and anlysis tool for protein families," Nucleic Acid Research 2003:31(1)319-321.

Fisher, "The molecular design of reteplase," *Drugs of today*, 33(9), 641-648 (1997)).

Forlani F. et al. Evidence that elongation of the catalytic loop of the Azotobacter vinelandii rhodanese changed selectivity from sulfur- to phosphate-containing substrates. Protein Eng. Jul. 2003;16(7):515-9.

Gibrat et al "Surprising similarities in structure comparison." Curr Opin Struct Biol. Jun. 1996;6(3):377-85.

Gregoret and Sauer, "Additivity of mutant effects assessed by binomial mutagenesis." Proc Natl Acad Sci U S A. May 1, 1993;90(9):4246-50.

Grüninger-Leitch, et al. "Substrate and inhibitor profile of BACE (beta-secretase) and comparison with other mammalian aspartic proteases." J Biol Chem. Feb. 15, 2002;277(7):4687-93. Epub Dec. 7, 2001.

Guex and Peitsch, "SWISS-MODEL and the Swiss-PdbViewer: an environment for comparative protein modeling." Electrophoresis. Dec. 1997;18(15):2714-23.

Hamilton et al. "Tumour necrosis factor-alpha blockade: a new era for effective management of rheumatoid arthritis." Expert Opin Pharmacother. Jul. 2000;1(5):1041-52.

Hedstrom et al. "Converting trypsin to chymotrypsin: the role of surface loops." Science. Mar. 6, 1992;255(5049):1249-53.

Heuer and Blumenberg "[Recombinant factor VIIa (NovoSeven). A review of current and possible future indications]" Anaesthesist. May 2002;51(5):388-99. Review. German.

Holm and Sander "Touring protein fold space with Dali/FSSP." Nucleic Acids Res. Jan. 1, 1998;26(1):316-9.

Horrevoets et al. "Thrombin-variable region 1 (VR1). Evidence for the dominant contribution of VR1 of serine proteases to their interaction with plasminogen activator inhibitor 1." J Biol Chem. Jan. 15, 1993;268(2):779-82.

Kageyama, T. "Pepsinogens, progastricsins, and prochymosins: structure, function, evolution, and development." Cell Mol Life Sci. Feb. 2002;59(2):288-306. Review.

Kurth, T. et al. "Engineering the S1' subsite of trypsin: design of a protease which cleaves between dibasic residues." Biochemistry. Aug. 18, 1998;37(33):11434-40.

Lesley et al. "Preparation and use of *E. coli* S-30 extracts." Methods Mol Biol. 1995;37:265-78. No abstract available.

Murakami et al. "Random insertion and deletion of arbitrary number of bases for codon-based random mutation of DNAs." Nat Biotechnol. Jan. 2002;20(1):76-81.

Murphy et al. "Effect of a range of new xylanases on in vitro viscosity and on performance of broiler diets." British Poultry Science 44, S16-S18 (2003.

Murzin A. G. et al. << SCOP: a structural classification of proteins database for the investigation of sequences and structures. J Mol Biol. Apr. 7, 1995;247(4):536-40.

Orengo et al. "CATH—a hierarchic classification of protein domain structures." Structure. Aug. 15, 1997;5(8):1093-1108.

Ostermeier, M. et al. "A combinatorial approach to hybrid enzymes independent of DNA homology." Nat Biotechnol. Dec. 1999;17(12):1205-9.

Ottesen,M. & Svendsen,A. "The substilisins" (1998) *Methods Enzymol.* 1970, 199-215.

Perona & Craik, "Structural basis of substrate specificity in the serine proteases." Protein Sci. Mar. 1995;4(3):337-60. Review.

Perona, & Craik, "Evolutionary divergence of substrate specificity within the chymotrypsin-like serine protease fold." J Biol Chem. Nov. 28, 1997;272(48):29987-90.

Pettit, S. et al. << Analysis of retroviral protease cleavage sites reveals two types of cleavage sites and the structural requirements of the P1 amino acid. J Biol Chem. Aug. 5, 1991;266(22):14539-47.

Rawlings & Barrett, "Families of aspartic peptidases, and those of unknown catalytic mechanism." Methods Enzymol. 1995;248:105-20.

Rawlings & Barrett, "Classification of peptidases by comparisions of primary and secondary structures," In. Proteolysis in Cell Functions (eds Hopsu-Havu; Jarvinen; Kirschke) 1997, 13-27, IOS Press, Amsterdam.

Rawlings, & Barrett, "Families of cysteine peptidases." Methods Enzymol. 1994;244:461-86.

Rawlings, & Barrett, "Families of serine peptidases." Methods Enzymol. 1994;244:19-61.

Schechter & Berger, "On the size of the active site in proteases. I. Papain." Biochem Biophys Res Commun. Apr. 20, 1967;27(2):157-62.

Seidah & Chretien,. "Eukaryotic protein processing: endoproteolysis of precursor proteins." Curr Opin Biotechnol. Oct. 1997;8(5):602-7.

Sices, & Kristie, "A genetic screen for the isolation and characterization of site-specific proteases." Proc Natl Acad Sci U S A. Mar. 17, 1998;95(6):2828-33.

Turner, et al. "Structural elements that govern the substrate specificity of the clot-dissolving enzyme plasmin." J Biol Chem. Sep. 6, 2002;277(36):33068-74. Epub Jun. 21, 2002.

Verstraete, et al. "Thrombolytic agents in development." Drugs. Jul. 1995;50(1):29-42. Review.

Wang, & Liang, "Substrate specificity of porcine renin: P1', P1, and P3 residues of renin substrates are crucial for activity." Biochemistry. Dec. 6, 1994;33(48):14636-41.

Weiss et al., "Rapid mapping of protein functional epitopes by combinatorial alanine scanning." Proc Natl Acad Sci U S A. Aug. 1, 2000;97(16):8950-4.

Wu, et al. "Structural basis for specificity of retroviral proteases." Biochemistry. Mar. 31, 1998;37(13):4518-26.

Wyss, et al. "Biochemical characterization of fungal phytases (myo-inositol hexakisphosphate phosphohydrolases): Catalytic properties." Applied & Environmental Microbiology 65, 367-373 (1999.

Handel et al. "Inhibition of Transcription Factors by Anti-inflammatory and Anti-rheumatic Drugs: Can Variability in Response Be Overcome." Clinical and Experimental Pharmacology and Physiology (2000) 27 139-144.

Kollias et al. "Role of TNF/TNFR in autoimmunity: specific TNF receptor blockade may be advantageous to anti-TNF treatments." Cytokine & Growth Factor Reviews 13 (2002) 315-321.

Armisen et al. "Selective adsorption of poly-His tagged glutaryl acylase on tailor-made metal chelate supports." Journal of Chromatography A. 848 (1999) 61-70.

Dale et al. "Co-medication with hydrolytic enzymes in radiation therapy of uterine cervix: evidence of the reduction of acute side effects." Cancer Chemotherapy Pharmacoal (2001) 47 (Suppl): S29-S34.

Pandy et al. "Proteases and Protease Inhibitors: Implications in Antitumorigenesis and Drug Development", Int. J. Hum Genet, 7(1): 67-82 (2007).

Whisstock et al. "Prediction of protein function from protein sequence and structure." Quarterly Review of Biophysics 36. (2003) pp. 307-340.

U.S. Appl. No. 10/872,198, filed Jun. 18, 2004, pending.

U.S. Appl. No. 11/021,951, filed Dec. 22, 2004, pending.

* cited by examiner

```
Trypsin         IVGGYNCEENSVPYQVSL---NSGYHF-CGGSLINEQWVVSAGHCY----
a-Thrombin      IVEGSDAEIGMSPWQVMLFRKSPQELL-CGASLISDRWVLTAAHCLLYPP
Enteropeptidase IVGGSNAKEGAWPWVVGL---YYGGRLLCGASLVSSDWLVSAAHCVYGRN
                 ** *          * *           ** **     *   * **  ----

Trypsin         ------KSRIQVRLGEH---NIEVLEGN-EQFINAAKIIRHPQYD-RKTL
a-Thrombin      WDKNFTENDLLVRIGKH---SRTRYERNIEKISMLEKIYIHPRYNWRENL
Enteropeptidase LE----PSKWTAILGLHMKSNLTSPQTV-PRLID--EIVINPHYN-RRRK
                -1----              * *                  *  ** *

Trypsin         NNDIMLIKLSSRAVINARVSTISLPTA----PPAT-----GTKCLISGWG
a-Thrombin      DRDIALMKLKKPVAFSDYIHPVCLPDR----ETAASLLQAGYKGRVTGWG
Enteropeptidase DNDIAMMHLEFKVNYTDYIQPICLPEENQVFPP-------GRNCSIAGWG
                 ** *              **  *     ------2------*    ***

Trypsin         N-----TASSGADYPDELQCLDAPVLSQAKCEASYPG-KITSNMFCVGFL
a-Thrombin      NLKETWTANVGKGQPSVLQVVNLPIVERPVCKDSTRI-RITDNMFCAGYK
Enteropeptidase T-----VVYQGTT-ANILQEADVPLLSNERCQQQMPEYNITENMICAGYE
                 --3--        *      **  *    *         ** ** * *

Trypsin         -EGGK--DSCQGDSGGPVVCNGQ----LQ------GVVSWGDGCAQKNKP
a-Thrombin      PDEGKRGDACEGDSGGPFVMKSP----FNNRWYQMGIVSWGEGCDRDGKY
Enteropeptidase -EGGI--DSCQGDSGGPLMCQENNRWFLA------GVTSFGYKCALPNRP
                 *   *  * * ******            ------4------*  *  * *

Trypsin         GVYTKVYNYVKWIKNTIAANS-
a-Thrombin      GFYTHVFRLKKWIQKVIDQFGE
Enteropeptidase GVYARVSRFTEWIQSFLH----
                 * *    *    **
```

Fig. 2

```
sub     IAHEYAQSV--PY---------------GISQ--IKAPALHSQGY---------------
furin   VAKRRAKRD--VYQEPTDPKFPQQWYLSGVTQRDLNVKEAWAQGF---------------
PC_SK1  EKERSKRSALRDS--------------ALNL--FNDPMWNQQWYLQDTRMTAALPKLDL
PC_SK5  NTHPCQ---------------------SD--MNIEGAWKRGY-----------------
                   ------------1---------------   ---------------2-- sub     ----------TGSNVKVAVIDSGIDSSHPDL--NVRGGAS--FVPSETN-------P---
furin   ----------TGHGIVVSILDDGIEKNHPDLAGNYDPGAS--FDVNDQD-------PDPQ
PC_SK1  HVIPVWQKGITGKGVVITVLDDGLEWNHTDIYANYDPEASYDFNDNDHD-------P---
PC_SK5  ----------TGKNIVVTILDDGIERTHPDL---MQNYDA--LASCDVNGNDLDPMP---
        --------------   *  *    * *------3------   --------------- sub     ----YQ-----DGSS---HGTHVAGTIA--AL-NNSIGVLGVSPSASLYAVKVLDS----
furin   PRYTQM-----NDNR---HGTRCAGEVA--AVANNGVCGVGVAYNARIGGVRMLD-----
PC_SK1  ----FPRYDPTNENK---HGTRCAGEIAMQAN-NHKCGV-GVAYNSKVGGIRMLDG----
PC_SK5  ----RY-----DASNENKHGTRCAGEVA--AAAANNSHCTVGIAFNAKIGGVRMLDGDVTD
        ------4-----------      *    *   *         *   ------- sub     -TGSGQYSWIINGIE-WAISNNMDVINMSLG---------GPT--GSTA------LKT--
furin   ----GEVTDAVEARS-LGLNPNHIHIYSASW---------GPEDDGKTVDGPARLAEE--
PC_SK1  -IVTDAIEASSIGFN----PGHVDIYSASWGPNDDGKTVEGP---GRLA------QKAFE
PC_SK5  MVEAKSVSFNPQHVHIYSASWGPDDDGKTVD---------GPA--PLT--------RQ--
        -5-------       -----6----    ----------7---------  ---------8- sub     --VVDKAVSSG-----IVVAAAAGNEGSS-------GSTSTVGYPAKYPSTIAVGAV---
furin   --AFFRGVSQGRGGLGSIFVWASGNGGREHDSCNCDGYTNSI-YTLSISSATQFGNV---
PC_SK1  YGVKQGRQGKG-----SIFVWASGNGGRQ-------GDNCDCD---GYTDSIYTISI---
PC_SK5  --AFENGVRMGRRGLGSVFVWASGNGGRSKDHCSCDGYTNSI-YTISISSTAESGKKPWY
        --------8----------  *----------9--------                ---- sub     --N------SSNQR--------------ASFSSAG-SELDVMAPGVSIQSTLPGGTYGAY
furin   --PWYSEACSSTLA--------------TTYSSGNQNEKQIVTTDLRQKCT------ESH
PC_SK1  --S------SASQQGLSPWYAEKCSSTLATSYSSG-DYTDQRITSADLHNDCT----ETH
PC_SK5  LEE------CSSTL--------------ATTYSSG-ESYDKKI----ITTDLRQRCTDNH
        ----------10-------------------*         --------------11--- sub     NGTSMATPHVAGAAALIL--SKHP--TWTNAQVRDRLESTATY--LG-NSFYYGKGLINV
furin   TGTSASAPLAAGIIALTLEANKNL--TWRDMQHLVVQTSKPAH--LN-ADDWATNGVGRK
PC_SK1  TGTSASAPLAAGIFALAL--EANP--NLTWRDMQHLVVWTSEYDPLA-NNPGWKKNGAGL
PC_SK5  TGTSASAPMAAGIIALAL--EANPFLTWRDVQHVIVRTSRAGH--LNANDWKTNAAGFKV
        ---*   *  **  ** *                                   *
```

Fig. 4

```
Peps.  TLVDEQP----LENYLDMEYFGTIGIGTPAQDFTVVFDTGSSNLWVPSVYCSSL--ACTN
Secr.  EMVDN------LRGKSGQGYYVEMTVGSPPQTLNILVDTGSSNFAVGAAPHPFL------
Cath.  PAVTEGPIPEVLKNYMDAQYYGEIGIGTPPQCFTVVFDTGSSNLWVPSIHCKLLDIACWI
       *    -----1-----   *      *  *  *     ******  *        -----2--

Peps.  HNRFNPEDSSTYQSTSETVSITYGTGSMTGILGYDTVQV-----------G---GISDTN
Secr.  HRYYQRQLSSTYRDLRKGVYVPYTQGKWEGELGTDLVSI-----------PHGPNVTVRA
Cath.  HHKYNSDKSSTYVKNGTSFDIHYGSGSLSGYLSQDTVSVPCQSASSASALG---GVKVER
       -     ****       -----3----*  *     *    ---------4----------

Peps.  QIFGLSETEPGSFLYYAPFDGILGLAYPSIS--SSGATPVFDNIWNQGLVSQDLFSVYLS
Secr.  NIAAITESDK-FFINGSNWEGILGLAYAEIARPDDSLEPFFDSLVKQTHVP-NLFSLQLC
Cath.  QVFGEATKQPGITFIAAKFDGILGMAYPRIS--VNNVLPVFDNLMQQKLVDQNIFSFYLS
           ----5----****  ------6-------  **    *  *    **   *

Peps.  ADD----------KS--GSVVIFGGIDSSYYTGSLNWVPVTVEGYWQITVDSITMNGETI
Secr.  GAGFPLNQSEVLASV--GGSMIIGGIDHSLYTGSLWYTPIRREWYYEVIIVRVEINGQDL
Cath.  RDP----------DAQPGGELMLGGTDSKYYKGSLSYLNVTRKAYWQVHLDQVEVASGLT
       --------7---------    **  *   * ***  -----8-----

Peps.  A--CAEGC--QAIVDTGTSLLTGPTSPIANIQSDIGASENSD--------GDMVVSCSAI
Secr.  KMDCKEYNYDKSIVDSGTTNLRLPKKVFEAAVKSIKAASSTEKFPDGFWLGEQLV-CWQA
Cath.  L--CKEGC--EAIVDTGTSLMVGPVDEVRELQKAIGAVPLIQ--------GEYMIPCEKV
        * *    *** **     *           *  *     -------9------ *

Peps.  SSLPDIVFTI-----------NGVQYPVPPSAYILQSEGS----CISGFQGMNVP-TESG
Secr.  GTTPWNIFPVISLYLMGEVTNQSFRITILPQQYLRPVEDV----ATSQDDCYKFAISQSS
Cath.  STLPAITLKL-----------GGKGYKLSPEDYTLKVSQAGKTLCLSGFMGMDIP-PPSG
       *     -------10-------    *  *  ---------------11----------

Peps.  ELWILGDVFIRQYFTVFDRANNQVGLAPVA
Secr.  TGTVMGAVIMEGFYVVFDRARKRIGFAVSA
Cath.  PLWILGDVFIGRYYTVFDRDNNRVGFAEAA
       --   * *    ****    *  *   *
```

Fig. 6

```
01   MLEADDQGCI  EEQGVEDSAN  EDSVDAKPDR  SSFVPSLFSK  KKKNVTMRSI  KTTRDRVPTY

61   QYNMNFEKLG  KCIIINNKNF  DKVTGMGVRN  GTDKDAEALF  KCFRSLGFDV  IVYNDCSCAK
                             ------1---------

121  MQDLLKKASE  EDHTNAACFA  CILLSHGEEN  VIYGKDGVTP  IKDLTAHFRG  DRSKTLLEKP
                                         ---------2---------

181  KLFFIQACRG  TELDDGIQAD  SGPINDTDAN  PRYKIPVEAD  FLFAYSTVPG  YYSWRSPGRG
             -----3--------                                     -----------4----

241  SWFVQALCSI  LEEHGKDLEI  MQILTRVNDR  VARHFESQSD  DPHFHEKKQI  PCVVSMLTKE
     ---                                            ----------5-------------

301  LYFSQ
```

Fig. 8

Protein scaffold
Protease A
Protease B 1   2   3   Candidate SDR insertion sites 1   2   3

Insertion of
random SDRs
into protein scaffold

Selection for increased
specificity

NBE with intended specificity

SDR1    SDR2  SDR3

Fig. 9

ENGINEERED ENZYMES AND USES THEREOF

This application claims the priority benefit of European Application No. 03013819, filed Jun. 18, 2003; European Application No. 03025851, filed Nov. 10, 2003; European Application No. 03025871, filed Nov. 11, 2003; and U.S. Provisional Application No. 60/524,960, filed Nov. 25, 2003, which applications are incorporated herein fully by this reference.

The present invention provides engineered enzymes comprised of a protein scaffold and Specificity Determining Regions, the production of such enzymes and the use thereof for therapeutic, research, diagnostic, nutritional care, personal care and industrial purposes.

BACKGROUND

Academic and industrial research continuously searches for functional proteins to be used as therapeutic, research, diagnostic, nutritional, personal care or industrial agents. Today, such functional proteins can be classified mainly into two categories: natural proteins and engineered proteins. Natural proteins, on the one hand, are discovered from nature, e.g. by screening natural isolates or by sequencing genomes from diverse species. Engineered proteins, on the other hand, are typically based on known proteins and are altered in order to acquire modified functionalities. The present invention discloses engineered proteins with novel functions as compared to the starting components. Such proteins are called NBEs (New Biologic Entities). The NBEs disclosed in the present invention are engineered enzymes with novel substrate specificities or fusion proteins of such engineered enzymes with other functional components.

Specificity is an essential element of enzyme function. A cell consists of thousands of different, highly reactive catalysts. Yet the cell is able to maintain a coordinated metabolism and a highly organized three-dimensional structure. This is due in part to the specificity of enzymes, i.e. the selective conversion of their respective substrates. Specificity is a qualitative and a quantitative property: the specificity of a particular enzyme can vary widely, ranging from just one particular type of target molecules to all molecular types with certain chemical substructures. In nature, the specificity of an organism's enzymes has been evolved to the particular needs of the organism. Arbitrary specificities with high value for therapeutic, research, diagnostic, nutritional or industrial applications are unlikely to be found in any organism's enzymatic repertoire due to the large space of possible specificities. The only realistic way of obtaining such specificities is their generation de novo.

When comparing enzymes with binders, a paradigm of specificity is given by antibodies recognizing individual epitopes as small distinct structures within large molecules. The naturally occurring vast range of antibody specificities is attributed to the diversity generated by the immune system combined with natural selection. Several mechanisms contribute to the vast repertoire of antibody specificity and occur at different stages of immune response generation and antibody maturation (Janeway, C et al. (1999) Immunobiology, Elsevier Science Ltd., Garland Publishing, New York). Specifically, antibodies contain complementarity determining regions (CDRs) which interact with the antigen in a highly specific manner and allow discrimination even between very similar epitopes. The light as well as the heavy chain of the antibody each contribute three CDRs to the binding domain. Nature uses recombination of various gene segments combined with further mutagenesis in the generation of CDRs. As a result, the sequences of the six CDR loops are highly variable in composition and length and this forms the basis for the diversity of binding specificities in antibodies. A similar principle for the generation of a diversity of catalytic specificities is not known from nature.

Catalysis, i.e. the increase of the rate of a specific chemical reaction, is besides binding the most important protein function. Catalytic proteins, i.e. enzymes, are classified according to the chemical reaction they catalyze.

Transferases are enzymes transferring a group, for example, the methyl group or a glycosyl group, from one compound (generally regarded as donor) to another compound (generally regarded as acceptor). For example, glycosyltransferases (EC 2.4) transfer glycosyl residues from a donor to an acceptor molecule. Some of the glycosyltransferases also catalyze hydrolysis, which can be regarded as transfer of a glycosyl group from the donor to water. The subclass is further subdivided into hexosyltransferases (EC 2.4.1), pentosyltransferases (EC 2.4.2) and those transferring other glycosyl groups (EC 2.4.99, Nomenclature Committee of the International Union of Biochemistry and Molecular Biology (NC-IUBMB)).

Oxidoreductases catalyze oxido-reductions. The substrate that is oxidized is regarded as hydrogen or electron donor. Oxidoreductases are classified as dehydrogenases, oxidases, mono- and dioxygenases. Dehydrogenases transfer hydrogen from a hydrogen donor to a hydrogen acceptor molecule. Oxidases react with molecular oxygen as hydrogen acceptor and produce oxidized products as well as either hydrogen peroxide or water. Monooxygenases transfer one oxygen atom from molecular oxygen to the substrate and one is reduced to water. In contrast, dioxygenases catalyze the insert of both oxygen atoms from molecular oxygen into the substrate.

Lyases catalyze elimination reactions and thereby generate double bonds or, in the reverse direction, catalyze the additions at double bonds. Isomerases catalyze intramolecular rearrangements. Ligases catalyze the formation of chemical bonds at the expense of ATP consumption.

Finally, hydrolases are enzymes that catalyze the hydrolysis of chemical bonds like C—O or C—N. The E.C. classification for these enzymes generally classifies them by the nature of the bond hydrolysed and by the nature of the substrate. Hydrolases such as lipases and proteases play an important role in nature as well in technical applications of biocatalysts. Proteases hydrolyse a peptide bond within the context of an oligo- or polypeptide. Depending on the catalytic mechanism proteases are grouped into aspartic, serin, cysteine, metallo- and threonine proteases (Handbook of proteolytic enzymes. (1998) Eds: Barret, A; Rawling, N.; Woessner, J.; Academic Press, London). This classification is based on the amino acid side chains that are responsible for catalysis and which are typically presented in the active site in very similar orientation to each other. The scissile bond of the substrate is brought into register with the catalytic residues due to specific interactions between the amino acid side chains of the substrate and complementary regions of the protease (Perona, J. & Craik, C (1995) *Protein Science*, 4, 337-360). The residues on the N- and C-terminal side of the scissile bond are usually called $P_1$, $P_2$, $P_3$ etc and $P_1'$, $P_2'$, $P_3'$ and the binding pockets complementary to the substrate $S_1$, $S_2$, $S_3$ and $S_1'$, $S_2'$, $S_3'$, respectively (nomenclature according to Schlechter & Berger, Biochem. Biophys. Res. Commun. 27 (1967) 157-162). The selectivity of proteases can vary widely from being virtually nonselective—e.g. the Subtilisins—over a strict preference at the $P_1$ position—e.g. Trypsin selectively cutting on the C-terminal side of arginine or lysine residues—to highly specific proteases—e.g. human tissue-type plasminogen activator (t-PA) cleaving at the C-terminal side of the arginine in the sequence CPGRVVG (Ding, L et al. (1995) Proc. Natl. Acad. Sci. USA 92, 7627-7631; Coombs, G et al. (1996) *J. Biol. Chem.* 271, 4461-4467).

The specificity of proteases, i.e. their ability to recognize and hydrolyze preferentially certain peptide substrates, can be expressed qualitatively and quantitatively. Qualitative specificity refers to the kind of amino acid residues that are accepted by a protease at certain positions of the peptide substrate. For example, trypsin and t-PA are related with respect to their qualitative specificity, since both of them require at the $P_1$ position an arginine or a similar residue. On the other hand, quantitative specificity refers to the relative number of peptide substrates that are accepted as substrates by the protease, or more precisely, to the relative $k_{cat}/k_M$ ratios of the protease for the different peptides that are accepted by the protease. Proteases that accept only a small portion of all possible peptides have a high specificity, whereas the specificity of proteases that, as an extreme, cleave any peptide substrate would theoretically be zero.

Comparison of the primary, secondary as well as the tertiary structure of proteases (Fersht, A., Enzyme Structure and Mechanism, W. H. Freeman and Company, New York, 1995) allows identification of classes showing a high degree of conservation (Rawlings, N. D. & Barrett, A. J. (1997) In: *Proteolysis in Cell Functions* Eds. Hopsu-Havu, V. K.; Järvinen, M.; Kirschke, H, pp. 13-21, IOS Press, Amsterdam). A widely accepted scheme for protease classification has been proposed by Rawlings & Barrett (Handbook of proteolytic enzymes. (1998) Eds: Barret, A; Rawling, N.; Woessner, J.; Academic Press, London). For example, the serine proteases family can be subdivided into structural classes with chymotrypsin (class S1), subtilisin (class S8) and carboxypeptidase (class SC) folds, each of which includes nonspecific as well as specific proteases (Rawlings, N. D. & Barrett, A. J. (1994) *Methods Enzymol.* 244, 19-61). This applies to other protease families analogously. An additional distinction can be made according to the relative location of the cleaved bond in the substrate. Carboxy- and aminopeptidases cleave amino acids from the C- and N-terminus, respectively, while endopeptidases cut anywhere along the oligopeptide.

Many applications would be conceivable if enzymes with a basically unlimited spectrum of specificities were available. However, the use of such enzymes with high, low or any defined specificity is currently limited to those which can be isolated from natural sources. The field of application for these enzymes varies from therapeutic, research, diagnostic, nutritional to personal care and industrial purposes.

Enzyme additives in detergents have come to constitute nearly a third of the whole industrial enzyme market. Detergent enzymes include proteinases for removing organic stains, lipases for removing greasy stains, amylases for removing residues of starchy foods and cellulases for restoring of smooth surface of the fiber. The best known detergent enzyme is probably the nonspecific proteinase subtilisin, isolated from various *Bacillus* species.

Starch enzymes, such as amylases, occupy the majority of those used in food processing. While starch enzymes include products that are important for textile desizing, alcohol fermentation, paper and pulp processing, and laundry detergent additives, the largest application is for the production of high fructose corn syrup. The production of corn syrup from starch by means of industrial enzymes was a successful alternative to acid hydrolysis.

Apart from starch processing, enzymes are used for an increasing range of applications in food. Enzymes in food can improve texture, appearance and nutritional value or may generate desirable flavours and aromas. Currently used food enzymes in bakery are amylase, amyloglycosidases, pentosanases for breakdown of pentosan and reduced gluten production or glucose oxidases to increase the stability of dough. Common enzymes for dairy are rennet (protease) as coagulant in cheese production, lactase for hydrolysis of lactose, protease for hydrolysis of whey proteins or catalase for the removel of hydrogen peroxides. Enzymes used in brewing process are the above named amylases, but also cellulases or proteases to clarify the beer from suspended proteins. In wines and fruit juices, cloudiness is more commenly caused by starch and pectins so that amylases and pectinases increase yield and clarification. Papain and other proteinases are used for meat tenderizing.

Enzymes have also been developed to aid animals in the digestion of feed. In the western hemisphere, corn is a major source of food for cattle, swine, and poultry. In order to improve the bioavailability of phosphate from corn, phytase is commonly added (Wyss, M. et al. Biochemical characterization of fungal phytases (myo-inositol hexakisphosphate phosphohydrolases): Catalytic properties. Applied & Environmental Microbiology 65, 367-373 (1999)). Moreover, phytate hydrolysis has been shown to bring about improvements in digestibility of protein and absorption of minerals such as calcium (Bedford, M. R. & Schulze, H. EXOGENOUS ENZYMES FOR PIGS AND POULTRY [Review]. Nutrition Research Reviews 11, 91-114 (1998)). Another major feed enzyme is xylanase. This enzyme is particularly useful as a supplement for feeding stuff comprising more than about 10% of wheat barley or rye, because of their relatively high soluble fiber content. Xylanases cause two important actions: reduction of viscosity of the intestinal contents by hydrolyzing the gel-like high molecular weight arabinoxylans in feed (Murphy, T., C., Bedford, M. R. & McCracken, K. J. Effect of a range of new xylanases on in vitro viscosity and on performance of broiler diets. British Poultry Science 44, S16-S18 (2003)) and break down of polymers in cell walls which improve the bioavailability of protein and starch.

Biotech research and development laboratories routinely use special enzymes in small quantities along with many other reagents. These enzymes create a significant market for various enzymes. Enzymes like alkaline phosphatase, horseradish peroxidase and luciferase are only some examples. Thermostable DNA polymerases like Taq polymerase or restriction endonucleases revolutionized laboratory work. Therapeutic enzymes are a particular class of drugs, categorized by the FDA as biologicals, with a lot of advantages compared to other, especially non-biological pharmaceuticals. Examples for successful therapeutic enzymes are human clotting factors like factor VIII and factor IX for human treatment. In addition, digestive enzymes are used for various deficiencies in human digestive processes. Other examples are t-PA and streptokinase for the treatment of cardiovascular disease, beta-glucocerebrosidase for the treatment of Type I Gaucher disease, L-asparaginase for the the treatment of acute lymphoblastic leukemia and DNAse for the treatment of cystic fibrosis. An important issue in the application of proteins as therapeutics is their potential immunogenicity. To reduce this risk, one would prefer enzymes of human origin, which narrows down the set of available enzymes. The provision of designed enzymes, preferably of human origin, with novel, tailor-made specificities would allow the specific modification of target substrates at will, while minimizing the risk of immunogenicity. A further advantage of highly specific enzymes as therapeutics would be their lower risk of side effects. Due to the limited possibility of specific interactions between a small molecule and a protein, binding to non-target proteins and therefore side effects are quite common and often cause termination of an otherwise promising lead compound. Specific enzymes, on the other hand, provide many more contact sites and mechanisms for substrate discrimination and therefore enable a higher specificity and thereby less side activities.

Proteases represent an important class of therapeutic agents (*Drugs of today*, 33, 641-648 (1997)). However, currently the therapeutic protease is usually a substitute for insufficient acitivity of the body's own proteases. For example, factor VII can be administered in certain cases of coagulation deficiencies of bleeders or during surgery (Heuer L.; Blumenberg D. (2002) *Anaesthesist* 51:388). Tissue-type plasminogen activator (t-PA) is applied in acute cardiac infarction, initializing the dissolution of fibrin clots through specific cleavage and activation of plasminogen (Verstraete, M. et al. (1995) *Drugs*, 50, 29-41). So far a protease with taylor-made specificity is generated to provide a therapeutic agent that specifically activates or inactivates a disease related target protein.

Monoclonal antibodies represent another important biological class of substances with therapeutic capabilities. One of the main antibody targets are tumor necrosis factors (TNFs) which belong to the family of cytokines. TNFs play a major role in the inflammation process. As homotrimers they could bind to receptors of nearly every cell. They activate a multiplicity of cellular genes, multiple signal transduction mechanisms, kinases and transcription factors. The most important TNFs are TNF-alpha and TNF-beta. TNF-alpha is produced by macrophages, monocytes and other cells. TNF-alpha is an inflammation mediator. Therefore, research of the last decade has been focused on TNF-alpha inhibitors like monoclonal antibodies as possible therapeutics for different therapeutic indications like Rheumatoid Arthritis, Crohn's disease or Psoriasis (Hamilton et al. (2000) Expert Opin Pharmacother, 1 (5): 1041-1052). One of the major disadvantages of monoclonal antibodies are their high costs, so that new biological alternatives are of great importance.

There are a lot of examples for engineered enzymes in literature. Fulani et al. (Fulani F. et al. (2003) *Protein Engineering* 16, 515-519) describe a rhodanase (thiosulfat: cyanide sulfurtransferase) from *Azotobacter vinelandii* which has a catalytic domain structurally related to catalytic subunit of Cdc25 phosphatase enzymes. The difference in catalytic mechanism depends on the different size of the active site. Both rhodanase and phosphatase are highly specific on different substrates (sulfate vs. phosphate). The catalytic mechanism of the rhodanase could be shifted towards serine/threonine phosphatase by single-residue insertion. Therefore, Fulani et al. give a single example for the change of a catalytic mechanism by structural comparison and sequence alignment of naturally known enzymes from different enzyme classes but lack an indication of how to generate a user-definable substrate specificity while keeping the same catalytic mechanism.

The thioredoxin reductase described by Briggs et al. (WO 02/090300 A2) has an altered cofactor specificity which preferably binds NADPH compared to NADH. Thus, both enzymes, the starting point as well as the resulting engineered enzyme are highly specific towards different substrates. The methods to achieve such an altered substrate specificity are either computational processing methods or sequence alignments of related proteins to define variable and conserved residues. They all have in common that they are based on the comparison of structures and sequences of proteins with known specificities followed by the transfer of the same to another backbone.

There are other examples of specificity-engineered enzymes and, in particular, of proteases which have been published in the literature. None of these examples, however, provides a means for generating novel specificites compared to the specificity of the starting material used within the described methods. The methods range from structure-directed single point mutations (Kurth, T. et al. (1998) *Biochemistry* 37, 11434-11440; Ballinger, M et al. (1996) *Biochemistry*, 35:13579-13585), exchange of surface loops between two specific proteases (Horrevoets et al. (1993) *J. Biol. Chem.* 268, 779-782), to random mutagenesis either regio-selectively or across the whole gene combined with in-vitro or in-vivo selection (Sices, H. & Kristie, T. (1998) *Proc. Natl. Acad. Sci. USA*, 95, 2828-2833).

The rational design of protease specificity is limited to very few examples. This approach is severely limited by the insufficient understanding of the complexities that govern folding and dynamics as well as structure-function relationships in proteins (Corey, M. J. & Corey, E. (1996) *Proc. Natl. Acad. Sci. USA*, 93:11428-11434). It is therefore difficult to alter the primary amino acid sequence of a protease in order to change its activity or specificity in a predictive way. In a successful example, Kurth et al. engineered trypsin to show a preference for a dibasic motive (Kurth, T. et al. (1998) *Biochemistry*, 37:11434-11440). In another example, Hedstrom et al. converted the $S_1$ substrate specificity of trypsin to that of chymotrypsin (Hedstrom, L. et al. (1992) Science, 255:1249-1253). This is an example where a known property was transferred from one backbone to another.

Ballinger et al. (WO 96/27671) describe subtilisin variants with combination mutations (N62D/G166D, and optionally Y104D) having a shift of substrate specificity towards peptide or polypeptide substrates with basic amino acids at the P1, P2 and P4 positions of the substrate. Suitable substrates of the variant subtilisin were revealed by sorting a library of phage particles (substrate phage) containing five contiguous randomized residues. These subtilisin variants are useful for cleaving fusion proteins with basic substrate linkers and processing hormones or other proteins (in vitro or in vivo) that contain basic cleavage sites.

The problems associated with rational redesign of enzymes can partially be overcome by directed evolution (as disclosed in PCT/EP03/04864). These studies can be classified by their expression and selection systems. Genetic selection means to produce inside an organism an enzyme, e.g. a protease, which is able to cleave a precursor protein which in turn results in an alteration of the growth behavior of the producing organism. From a population of organisms with different proteases those can be selected which have an altered growth behavior. This principle was for example reported by Davis et al. (U.S. Pat. No. 5,258,289, WO 96/21009). The production of a phage system is dependent on the cleavage of a phage protein which only can be activated in the presence of a proteolytic enzyme which is able to cleave the phage protein. Other approaches use a reporter system which allows a selection by screening instead of a genetic selection, but also cannot overcome the intrinsic insufficiency of the intracellular characterization of enzymes.

Systems to generate enzymes with altered sequence specificities with self-secreting enzymes are also reported. Duff et al. (WO 98/11237) describe an expression system for a self-secreting protease. An essential element of the experimental design is that the catalytic reaction acts on the protease itself by an autoproteolytic processing of the membrane-bound precursor molecule to release the matured protease from the cellular membrane into the extracellular environment. Therefore, a fusion protein must be constructed where the target peptide sequence replaces the natural cleavage site for autoproteolysis. Limitations of such a system are that positively identified proteases will have the ability to cleave a certain amino acid sequence but they also may cleave many other peptide sequences. Therefore, high substrate specificity can not be achieved. Additionally, such a system is not able to control that selected proteases cleave at a specific position in a defined amino acid sequence and it does not allow a precise characterization of the kinetic constants of the selected proteases ($k_{cat}$, $K_M$).

A method has been described that aims at the generation of new catalytic activities and specificities within the α/β-barrel proteins (WO 01/42432; Fersht et al, Methods of producing novel enzymes; Altamirano et al. (2000) *Nature* 403, 617-622). The α/β-barrel proteins comprise a large superfamily of proteins accounting for a large fraction of all known enzymes. The structure of the proteins is made from a/β-barrel surrounded by α-helices. The loops connecting β-strands and helices comprise the so-called lid-structure including the acitve site residues. The method is based on the classification of α/β-barrel proteins into two classes based on the catalytic lid structure. An extensive comparison of α/β-barrel protein structures led the authors to the conclusion that the substrate binding and specificity is primarily defined by the barrel structure while the specificity of the chemical reaction resides within the loops. It is suggested that barrels and lid structures from different enzymes can be combined to generate new enzymatic activities and to provide a starting point to fine tune the properties by targeted or randomized mutagenesis and selection. The method does not provide for the generation of user-defined specificity.

In summary, it is clear that there are many possible applications in the fields of therapeutics, research and diagnostics, industrial enzymes, food and feed processing, cosmetics and other areas that would become possible by the availability of enzymes with a novel substrate specificity. However, only a limited number of specific enzymes has been identified from natural sources so far. Methods of rational design to modify, alter, convert or transfer sequence specificity as well as random approaches described above did not enable the generation of a novel and user-definable specificity that was not present in the employed starting material.

Therefore, none of the currently available methods can provide enzymes with a novel and user-defined sequence specificity. In contrast, the current invention provides such enzymes as well as methods for generating them.

SUMMARY OF THE INVENTION

The objective of the present invention is to provide engineered proteins with novel functions that do not exist in the components used for the engineering of such proteins. In particular, the invention provides enzymes with user-definable specificities. User-definable specificity means that enzymes are provided with specificities that do not exist in the components used for the engineering of such enzymes. The specificities can be chosen by the user so that one or more intended target substrates are preferentially recognised and converted by the enzymes. Furthermore, the invention provides enzymes that possess essentially identical sequences to human proteins but have different specificities. In a particular embodiment, the invention provides proteases with user-definable specificities.

Furthermore, the present invention is directed to engineered enzymes which are fused to one or more further functional components. These further components can be proteinacious components which preferably have binding properties and are of the group consisting of substrate binding domains, antibodies, receptors or fragments thereof. Furthermore, these further components can be further functional components, preferably being selected from the group consisting of polyethylenglycols, carbohydrates, lipids, fatty acids, nucleic acids, metals, metal chelates, and fragments or derivatives thereof. The resulting fusion proteins are understood as enzymes with user-definable specificities within the present invention.

Besides, the invention is directed to the application of such enzymes with novel, user-definable specificities for therapeutic, research, diagnostic, nutritional, personal care or industrial purposes. Moreover, the invention is directed to a method for generating engineered enzymes with user-definable specificities. In particular, the invention is directed to generate enzymes that possess essentially identical sequences to human enzymes but have different specificities.

This problem has been solved by the embodiments of the invention specified in the description below and in the claims. The present invention is thus directed to (1) an engineered enzyme with defined specificity characterized by the combination of the following components:
  (a) a protein scaffold which catalyzes at least one chemical reaction on at least one substrate, and
  (b) one or more specificity determining regions (SDRs) located at sites in the protein scaffold that enable the resulting engineered protein to discriminate between at least one target substrate and one or more different substrates, and wherein the SDRs are essentially synthetic peptide sequences;

(2) the use of an engineered enzyme as defined in (1) above for therapeutic, research, diagnostic, nutritional, personal care or industrial purposes;

(3) a method for generating engineered enzymes as defined in (1) above having specificities towards target substrates, such specificities not being present in the individual starting components, comprising at least the following steps:
  (a) providing a protein scaffold which catalyzes at least one chemical reaction on at least one substrate,
  (b) generating a library of engineered enzymes by combining the protein scaffold from step (a) with fully or partially random peptide sequences at sites in the protein scaffold that enable the resulting engineered enzyme to discriminate between at least one target substrate and one or more different substrates, and
  (c) selecting out of the library of engineered enzymes generated in step (b) one or more enzymes that have specificities towards at least one target substrate;

(4) a fusion protein which is comprised of at least one engineered enzyme as defined in (1) above and at least one further component, preferably the at least one further component having binding properties and more preferably being selected from the group consisting of antiboides, binding domains, receptors, and fragments thereof;

(5) a composition or pharmaceutical composition comprising one or more engineered enzymes as defined in (1) above or a fusion protein as defined in (4) above, said pharmaceutical composition may optionally comprise an acceptable carrier, excipient and/or auxiliary agent;

(6) a DNA encoding the engineered enzyme as defined in (1) above;

(7) a vector comprising the DNA as defined in (6) above;

(8) a host cell or transgenic organism being transformed/transfected with a vector as defined in (7) above and/or containing the DNA as defined in (6) above; and (9) a method for producing the engineered enzyme comprising culturing a cell or organism as defined in (8) above and isolating the enzyme from the culture broth.

BRIEF DESCRIPTION OF THE FIGURES

The following figures are provided in order to explain further the present invention in supplement to the detailed description:

FIG. 2 shows the alignment of the primary amino acid sequence of three members of the serine protease class S1 family: human trypsin I, human alpha-thrombin and human enteropeptidase (see also SEQ ID NOs: 1, 5 and 6).

FIG. 4 shows the alignment of the primary amino acid sequences of four members of the serine protease class S8 family: subtilisin E, furin, PC1 and PC5 (see also SEQ ID NOs: 7-10).

FIG. 6 shows the alignment of the primary amino acid sequences of three members of the A1 aspartic acid protease family: pepsin, β-secretase and cathepsin D (see also SEQ ID NOs: 11-13).

FIG. 8: shows the primary amino acid sequence of caspase 7 as a member of the cysteine protease class C14 family (see also SEQ ID NO: 14).

FIG. 9 depicts schematically the third aspect of the invention.

DEFINITIONS

Figure 1:
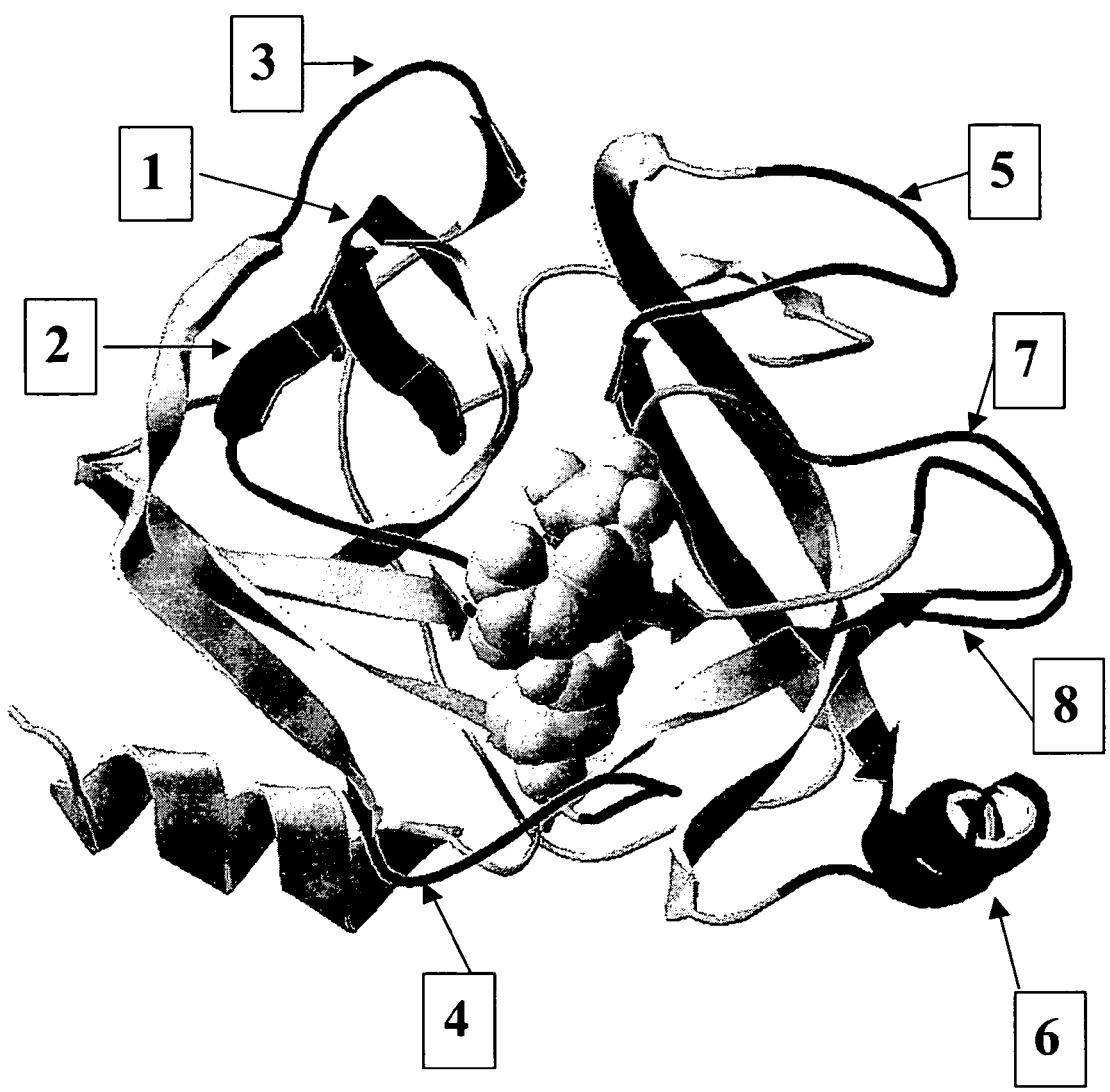
FIG. 1 illustrates the three-dimensional structure of human trypsin I with the active site residues shown in "ball-and-stick" representation and with the marked regions indicating potential SDR insertion sites.

In the framework of the present invention the following terms and definitions are used.

The term "protease" means any protein molecule that is capable of hydrolysing peptide bonds. This includes naturally-occurring or artificial proteolytic enzymes, as well as variants thereof obtained by site-directed or random mutagenesis or any other protein engineering method, any active fragment of a proteolytic enzyme, or any molecular complex or fusion protein comprising one of the aforementioned proteins. A "chimera of proteases" means a fusion protein of two or more fragments derived from different parent proteases.

The term "substrate" means any molecule that can be converted catalytically by an enzyme. The term "peptide substrate" means any peptide, oligopeptide, or protein molecule of any amino acid composition, sequence or length, that contains a peptide bond that can be hydrolyzed catalytically by a protease. The peptide bond that is hydrolyzed is referred to as the "cleavage site". Numbering of positions in the substrate is done according to the system introduced by Schlechter & Berger (Biochem. Biophys. Res. Commun. 27 (1967) 157-162). Amino acid residues adjacent N-terminal to the cleavage site are numbered $P_1$, $P_2$, $P_3$, etc., whereas residues adjacent C-terminal to the cleavage site are numbered $P_1'$, $P_2'$, $P_3'$, etc.

The term "target substrate" describes a user-defined substrate which is specifically recognized and converted by an enzyme according to the invention. The term "target peptide substrate" describes a user-defined peptide substrate. The term "target specificity" describes the qualitative and quantitative specificity of an enzyme that is capable of recognizing and converting a target substrate.

Catalytic properties of enzymes are expressed using the kinetic parameters "$K_M$" or "Michaelis Menten constant", "$k_{cat}$" or "catalytic rate constant", and "$k_{cat}/K_M$" or "catalytic efficiency", according to the definitions of Michaelis and Menten (Fersht, A., Enzyme Structure and Mechanism, W. H. Freeman and Company, New York, 1995). The term "catalytic activity" describes quantitatively the conversion of a given substrate under defined reaction conditions.

The term "specificity" means the ability of an enzyme to recognize and convert preferentially certain substrates. Specificity can be expressed qualitatively and quantitatively. "Qualitative specificity" refers to the chemical nature of the substrate residues that are recognized by an enzyme. "Quantitative specificity" refers to the number of substrates that are accepted as substrates. Quantitative specificity can be expressed by the term s, which is defined as the negative logarithm of the number of all accepted substrates divided by the number of all possible substrates. Proteases, for example, that accept preferentially a small portion of all possible peptide substrates have a "high specificity". Proteases that accept almost any peptide substrate have a "low specificity". Definitions are made in accordance to WO 03/095670 which is therefore incorporated by reference. Proteases with very low specificity are also referred to as "unspecific proteases". The term "defined specificity" refers to a certain type of specificity, i.e. to a certain target subtrate or a set of certain target substrates that are preferentially converted versus other substrates.

The term "engineered" in combination with the term "enzyme" describes an enzyme that is comprised of different components and that has features not being conferred by the individual components alone.

The term "protein scaffold" or "scaffold protein" refers to a variety of primary, secondary and tertiary polypeptide structures.

The term "peptide sequence" indicates any peptide sequence used for insertion or substitution into or combination with a protein scaffold. Peptide sequences are usually obtained by expression from DNA sequences which can be synthesized according to well-established techniques or can be obtained from natural sources. Insertion, substitution or combination of peptide sequences with the protein scaffold are generated by insertion, substitution or combination of oligonucleotides into or with a polynucleotide encoding the protein scaffold. The term "synthetic" in combination with the term "peptide sequence" refers to peptide sequences that are not present in the protein scaffold in which the peptide sequences are inserted or substituted or with which they are combined.

The term "components" in combination with the term "engineered enzyme" refers to peptide or polypeptide sequences that are combined in the engineering of such enzymes. Such components may among others comprise one or more protein scaffolds and one or more synthetic peptide sequences. The term "library of engineered enzymes" describes a mixture of engineered enzymes, whereby every single engineered enzyme is encoded by a different polynucleotide sequence. The term "gene library" indicates a library of polynucleotides that encodes the library of engineered enzymes. The term "SDR" or "Specificity determining region" refers to a synthetic peptide sequence that provides the defined specificity when combined with the protein scaffold at sites that enable the resulting enzymes to discriminate between the target substrate and one or more other substrates. Such sites are termed "SDR sites".

The terms "tertiary structure similar to the structure of" and "similar tertiary structure" in combination with the terms "enzyme" or "protein" refer to proteins in which the type, sequence, connectivity and relative orientation of the typical secondary structural elements of a protein, e.g. alpha-helices, beta-sheets, beta-turns and loops, are similar and the proteins are therefore grouped into the same structural or topological class or fold. This includes proteins that have altered, additional or deleted structural elements of any type but otherwise unchanged topology. Examples of such structural classes are the TNF superfamily, the S1 fold or the S8 fold within the serine proteases, the GPCRs, or the α/β-barrel fold.

The term "positions that correspond structurally" indicates amino acids in proteins of similar tertiary structure that correspond structurally to each other, i.e. they are usually located within the same structural or topological element of the structure. Within the structural element they possess the same relative positions with respect to beginning and end of the structural element. If, e.g. the topological comparison of two proteins reveals two structurally corresponding sequences of different length, then amino acids within, e.g. 20% and 40% of the respective region lengths, correspond to each other structurally.

The term "library of engineered enzymes" of the present invention refers to a multiplicity of enzymes or enzyme variants, which may exist as a mixture or in isolated form.

Amino acids residues are abbreviated according to the following Table 1 either in one- or in three-letter code.

TABLE 1

Amino acid abbreviations

| Abbreviations | | Amino acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophane |
| Y | Tyr | Tyrosine |

DETAILED DESCRIPTION OF THE INVENTION

The present invention provides engineered proteins with novel functions. In particular, the invention provides enzymes with user-definable specificities. In a particular embodiment, the invention provides proteases with user-definable specificities. Besides, the invention provides applications of such enzymes with novel, user-definable specificities for therapeutic, research, diagnostic, nutritional, personal care or industrial purposes. Moreover, the invention provides a method for generating enzymes with specificities that are not present in the components used for the engineering of such enzymes. In particular, the invention is directed to the generation of enzymes that have sequences that are essentially identical to mammalian, especially human enzymes but have different specificities. Moreover, the invention provides libraries of specific engineered enzymes with corresponding specificities encoded genetically, a method for the generation of libraries of specific engineered enzymes with corresponding specificities encoded genetically, and the application of such libraries for technical, diagnostic, nutritional, personal care or research purposes.

A first aspect of the invention discloses engineered enzymes with defined specificities. These engineered enzymes are characterized by the following components:

(a) a protein scaffold capable of catalyzing at least one chemical reaction on a substrate, and (b) one or more specificity determining regions (SDRs) located at sites in the protein scaffold that enable the resulting engineered protein to discriminate between ar least one target substrate and one or more different substrates, wherein the SDRs are essentially synthetic peptide sequences.

Preferably, such defined specificity of the engineered enzymes is not conferred by the protein scaffold.

In principle, the protein scaffold can have a variety of primary, secondary and tertiary structures. The primary structure, i.e. the amino acid sequence, can be an engineered sequence or can be derived from any viral, prokaryotic or eukaryotic origin. For human therapeutic use, however, the protein scaffold is preferably of mammalian origin, and more preferably, of human origin. Furthermore, the protein scaffold is capable to catalyze one or more chemical reactions and has preferably only a low specificity.

Preferably, derivatives of the protein scaffold are used that have modified amino acid sequences that confer improved characteristics for the applicability as protein scaffolds. Such improved characteristics comprise, but are not limited to, stability; expression or secretion yield; folding, in particular after combination of the protein scaffold with SDRs; increased or decreased sensitivity to regulators such as activators or inhibitors; immunogenicity; catalytic rate; kM or substrate affinity.

The engineered enzymes reveal their quantitative specificity from the synthetic peptide sequences that are combined with the protein scaffold. Therefore, the engineered peptide sequences are acting as Specificity Determining Regions or SDRs. The number, the length and the positions of such SDRs can vary over a wide range. The number of SDRs within the scaffold is at least one, preferably more than one, more preferably between two and eleven, most preferably between two and six. The SDRs have a length between one and 50 amino acid residues, preferably a length between one and 15 amino acid residues, more preferably a length between one and six amino acid residues. Alternatively, the SDRs have a length between two and 20 amino acid residues, preferably a length between two and ten amino acid residues, more preferably a length between three and eight amino acid residues.

The inventive engineered enzymes can further be desribed as antibody-like protein molecules comprising constant and variable regions, but having a non-immunoglogulin backbone and having an active site (catalytic activity) in the constant region, whereby the substrate specificity of the active site is modulated by the variable region. Preferably, as in the immunoglobulin structure, the variable regions are loops of variable length and composition that interact with a target molecule.

In a particular variant of the invention, the engineered enzymes have hydrolase activity. In a preferred variant, the engineered enzymes have proteolytic activity. Particularly preferred protein scaffolds for this variant are unspecific proteases or are parts from unspecific proteases or are otherwise derived from unspecific proteases. The expressions "derived from" or "a derivative thereof" in this respect and in the following variants and embodiments refer to derivatives of proteins that are mutated at one or more amino acid positions and/or have a homology of at least 70%, preferably 90%, more preferably 95% and most preferably 99% to the original protein, and/or that are proteolytically processed, and/or that have an altered glycosylation pattern, and/or that are covalently linked to non-protein substances, and/or that are fused with further protein domains, and/or that have C-terminal and/or N-terminal truncations, and/or that have specific insertions, substitutions and/or deletions. Alternatively, "derived from" may refer to derivatives that are combinations or chimeras of two or more fragments from two or more proteins, each of which optionally comprises any or all of the aforementioned modifications. The tertiary structure of the protein scaffold can be of any type. Preferably, however, the tertiary structure belongs to one of the following structural classes: class S1 (chymotrypsin fold of the serine proteases family), class S8 (subtilisin fold of the serine proteases family), class SC (carboxypeptidase fold of the serine proteases family), class A1 (pepsin A fold of the aspartic proteases), or class C14 (caspase-1 fold of the cysteine proteases). Examples of proteases that can serve as the protein scaffold of engineered proteolytic enzymes for the use as human therapeutics are or are derived from human trypsin, human thrombin, human chymotrypsin, human pepsin, human endothiapepsin, human caspases 1 to 14, and/or human furin.

The defined specificity of the engineered proteolytic enzymes is a measure of their ability to discriminate between at least one target peptide or protein substrates and one or more further peptide or protein substrates. Preferably, the defined specificity refers to the ability to discriminate peptide or protein substrates that differ in other positions than the P1 site, more preferably, the defined specificity refers to the ability to discriminate peptide or protein substrates that differ in other positions than the P1 site and the P1' site. Most preferably, the engineered proteolytic enzymes distinguish target peptid or protein substrates at as many sites as is necessary to preferentially hydrolyse the target substrate versus other proteins. As an example, a therapeutically useful engineered proteolytic enzyme applied intravenously in the human body should be sufficiently specific to discriminate between the target substrate and any other protein in the human serum. Preferably, such an engineered proteolytic enzyme recognizes and discriminates peptide substrates at three or more amino acid positions, more preferably at four or more positions, and even more preferably at five or more amino acid positions. These positions may either be adjacent or non-adjacent.

In a first embodiment, the protein scaffold has a tertiary structure or fold equal or similar to the tertiary structure or fold of the S1 structural subclass of serine proteases, i.e. the chymotrypsin fold, and/or has at least 70% identity on the amino acid level to a protein of the S1 structural subclass of serine proteases. It is preferred that SDRs are inserted into the protein scaffold at one or more positions from the group of positions that correspond structurally or by amino acid sequence homology to the regions 18-25, 38-48, 54-63, 73-86, 122-130, 148-156, 165-171 and 194-204 in human trypsin I, and more preferably at one or more positions from the group of positions that correspond structurally or by amino acid sequence homology to the regions 20-23, 41-45, 57-60, 76-83, 125-128, 150-153, 167-169 and 197-201 (numbering of amino acids according to SEQ ID NO:1). The number of SDRs to be combined with this type of protein scaffold is preferably between 1 and 10, and more preferably between 2 and 4. Preferably, the protein scaffold is equal to or is a derivative or homologue of one or more of the following proteins: chymotrypsin, granzyme, kallikrein, trypsin, mesotrypsin, neutrophil elastase, pancreatic elastase, enteropeptidase, cathepsin, thrombin, ancrod, coagulation factor IXa, coagulation factor VIIa, coagulation factor Xa, activated protein C, urokinase, tissue-type plasminogen activator, plasmin, Desmodus-type plasminogen activator. More preferably, the protein scaffold is trypsin or thrombin or is a derivative or homologue from trypsin or thrombin. For the use as a human therapeutic, the trypsin or thrombin scaffold is most preferably of human origin in order to minimize the risk of an immune response or an allergenic reaction.

Preferably, derivatives with improved characteristics derived from human trypsin I or from proteins with similar tertiary structure are used. Preferred examples of such derivatives are derived from human trypsin I (SEQ ID NO:1) and comprise one or more of the following amino acid substitutions E56G; R78W; Y131F; A146T; C183R. It is preferred that at least one of two SDRs are inserted into human trypsin I, or a derivative thereof, between residues 42 and 43 (SDR 1) and between 123 and 124 (SDR 2), respectively (numbering of amino acids according to SEQ ID NO:1). In addition the SDR 1 has a preferred length of 6 and the SDR 2 has a preferred length of 5 amino acids, respectively. In a preferred variant of this embodiment, the SDR 1 and SDR 2 sequences comprise one of the amino acid sequences listed in table 2. Such engineered proteolytic enzymes have specificity for the target substrate B as exemplified in example IV.

In a further embodiment the protein scaffold belongs to the S8 structural subclass of serine proteases and/or has a tertiary structure similar to subtilisin E from *Bacillus subtilis* and/or has at least 70% identity on the amino acid level to a protein of the S8 structural subclass of serine proteases. Preferably, the scaffold belongs to the subtilisin family or the human pro-protein convertases. It is preferred that SDRs are inserted into the protein scaffold at one or more positions from the group of positions that correspond structurally or by amino acid sequence homology to the regions 6-17, 25-29, 47-55, 59-69, 101-111, 117-125, 129-137, 139-154, 158-169, 185-195 and 204-225 in subtilisin E from *Bacillus subtilis*, and more preferably at one or more positions from the group of positions that correspond structurally or by amino acid sequence homology to the regions 59-69, 101-111, 129-137, 158-169 and 204-225 (numbering of amino acids according to SEQ ID NO:7). It is preferred that the protein scaffold is equal to or is a derivative or homologue of one or more of the following proteins: subtilisin Carlsberg; *B. subtilis* subtilisin E; subtilisin BPN'; *B. licheniformis* subtilisin; *B. lentus* subtilisin; *Bacillus alcalophilus* alkaline protease; proteinase K; kexin; human pro-protein convertase; human furin. In a preferred variant, subtilisin BPN' or one of the proteins SPC 1 to 7 is used as the protein scaffold.

In a further embodiment the protein scaffold belongs to the family of aspartic proteases and/or has a tertiary structure similar to human pepsin. Preferably, the scaffold belongs to the A1 class of proteases and/or has at least 70% identity on the amino acid level to a protein of the A1 class of proteases. It is preferred that SDRs are inserted into the protein scaffold at one or more positions from the group of positions that correspond structurally or by amino acid sequence homology to the regions 6-18, 49-55, 74-83, 91-97, 112-120, 126-137, 159-164, 184-194, 242-247, 262-267 and 277-300 in human pepsin, and more preferably at one or more positions from the group of positions that correspond structurally or by amino acid sequence homology to the regions 10-15, 75-80, 114-118, 130-134, 186-191 and 280-296 (numbering of amino acids according to SEQ ID NO:11). It is preferred that the protein scaffold is equal to or is a derivative or homologue of one or more of the following proteins: pepsin, chymosin, renin, cathepsin, yapsin. Preferably, pepsin or endothiopepsin or a derivative or homologue thereof is used as the protein scaffold.

In a further embodiment the protein scaffold belongs to the cysteine protease family and/or has a tertiary structure similar to human caspase 7. Preferably the scaffold belongs to the C14 class of cysteine proteases or has at least 70% identity on the amino acid level to a protein of the C14 class of cysteine proteases. It is preferred that SDRs are inserted into the protein scaffold at one or more positions from the group of positions that correspond structurally or by amino acid sequence homology to the regions 78-91, 144-160, 186-198, 226-243 and 271-291 in human caspase 7, and more preferably at one or more positions from the group of positions that correspond structurally or by amino acid sequence homology to the regions 80-86, 149-157, 190-194 and 233-238 (numbering of amino acids according to SEQ ID NO:14). It is preferred that the protein scaffold is equal to or is a derivative or homologue of one of the caspases 1 to 9.

In a further embodiment the protein scaffold belongs to the S11 class of serine proteases or has at least 70% identity on the amino acid level to a protein of the S11 class of serine proteases and/or has a tertiary structure similar to D-alanyl-D-alanine transpeptidase from *Streptomyces* species K15. It is preferred that SDRs are inserted into the protein scaffold at one or more positions from the group of positions that correspond structurally or by amino acid sequence homology to the regions 67-79, 137-150, 191-206, 212-222 and 241-251 in D-alanyl-D-alanine transpeptidase from *Streptomyces* species K15, and more preferably at one or more positions from the group of positions that correspond structurally or by amino acid sequence homology to the regions 70-75, 141-147, 195-202 and 216-220 (numbering of amino acids according to SEQ ID NO:15). It is preferred that the D-alanyl-D-alanine transpeptidase from *Streptomyces* species K15 or a derivative or homologue thereof is used as the scaffold.

In a further embodiment the protein scaffold belongs to the S21 class of serine proteases or has at least 70% identity on the amino acid level to a protein of the S21 class of serine proteases and/or has a tertiary structure similar to assemblin from human cytomegalovirus. It is preferred that SDRs are inserted into the protein scaffold at one or more positions from the group of positions that correspond structurally or by amino acid sequence homology to the regions 25-33, 64-69, 134-155, 162-169 and 217-244 in assemblin from human cytomegalovirus, and more preferably at one or more positions from the group of positions that correspond structurally or by amino acid sequence homology to the regions 27-31, 164-168 and 222-239 (numbering of amino acids according to SEQ ID NO:16). It is preferred that the assemblin from human cytomegalovirus or a derivative or homologue thereof is used as the scaffold.

In a further embodiment the protein scaffold belongs to the S26 class of serine proteases or has at least 70% identity on the amino acid level to a protein of the S26 class of serine proteases and/or has a tertiary structure similar to the signal peptidase from *Escherichia coli*. It is preferred that SDRs are inserted into the protein scaffold at one or more positions from the group of positions that correspond structurally or by amino acid sequence homology to the regions 8-14, 57-68, 125-134, 239-254, 200-211 and 228-239 in signal peptidase from *Escherichia coli*, and more preferably at one or more positions from the group of positions that correspond structurally or by amino acid sequence homology to the regions 9-13, 60-67, 127-132 and 203-209 (numbering of amino acids according to SEQ ID NO:17). It is preferred that the signal peptidase from *Escherichia coli* or a derivative or homologue thereof is used as the scaffold.

In a further embodiment the protein scaffold belongs to the S33 class of serine proteases or has at least 70% identity on the amino acid level to a protein of the S33 class of serine proteases and/or has a tertiary structure similar to the prolyl aminopeptidase from *Serratia marcescens*. It is preferred that SDRs are inserted into the protein scaffold at one or more positions from the group of positions that correspond structurally or by amino acid sequence homology to the regions 47-54, 152-160, 203-212 and 297-302 in prolyl aminopeptidase from *Serratia marcescens*, and more preferably at one or more positions from the group of positions that correspond structurally or by amino acid sequence homology to the regions 50-53, 154-158 and 206-210 (numbering of amino acids according to SEQ ID NO:18). It is preferred that the prolyl aminopeptidase from *Serratia marcescens* or a derivative or homologue thereof is used as the scaffold.

In a further embodiment the protein scaffold belongs to the S51 class of serine proteases or has at least 70% identity on the amino acid level to a protein of the S51 class of serine proteases and/or has a tertiary structure similar to aspartyl dipeptidase from *Escherichia coli*. It is preferred that SDRs are inserted into the protein scaffold at one or more positions from the group of positions that correspond structurally or by amino acid sequence homology to the regions 8-16, 38-46, 85-92, 132-140, 159-170 and 205-211 in aspartyl dipeptidase from *Escherichia coli*, and more preferably at one or more positions from the group of positions that correspond structurally or by amino acid sequence homology to the regions 10-14, 87-90, 134-138 and 160-165 (numbering of amino acids according to SEQ ID NO:19). It is preferred that the aspartyl dipeptidase from *Escherichia coli* or a derivative or homologue thereof is used as the scaffold.

In a further embodiment the protein scaffold belongs to the A2 class of aspartic proteases or has at least 70% identity on the amino acid level to a protein of the A2 class of aspartic proteases and/or has a tertiary structure similar to the protease from human immunodeficiency virus. It is preferred that SDRs are inserted into the protein scaffold at one or more positions from the group of positions that correspond structurally or by amino acid sequence homology to the regions 5-12, 17-23, 27-30, 33-38 and 77-83 in protease from human immunodeficiency virus, and more preferably at one or more positions from the group of positions that correspond structurally or by amino acid sequence homology to the regions 7-10, 18-21, 34-37 and 79-82 (numbering of amino acids according to SEQ ID NO:20). It is preferred that the protease from human immunodeficiency virus, preferably HIV-1 protease, or a derivative or homologue thereof is used as the scaffold.

In a further embodiment the protein scaffold belongs to the A26 class of aspartic proteases or has at least 70% identity on the amino acid level to a protein of the A26 class of aspartic proteases and/or has a tertiary structure similar to the omptin from *Escherichia coli*. It is preferred that SDRs are inserted into the protein scaffold at one or more positions from the group of positions that correspond structurally or by amino acid sequence homology to the regions 28-40, 86-98, 150-168, 213-219 and 267-278 in omptin from *Escherichia coli*, and more preferably at one or more positions from the group of positions that correspond structurally or by amino acid sequence homology to the regions 33-38, 161-168 and 273-277 (numbering of amino acids according to SEQ ID NO:21). It is preferred that the omptin from *Escherichia coli* or a derivative or homologue thereof is used as the scaffold.

In a further embodiment the protein scaffold belongs to the C1 class of cysteine proteases or has at least 70% identity on the amino acid level to a protein of the C1 class of cysteine proteases and/or has a tertiary structure similar to the papain from *Carica papaya*. It is preferred that SDRs are inserted into the protein scaffold at one or more positions from the group of positions that correspond structurally or by amino acid sequence homology to the regions 17-24, 61-68, 88-95, 135-142, 153-158 and 176-184 in papain from *Carica papaya*, and more preferably at one or more positions from the group of positions that correspond structurally or by amino acid sequence homology to the regions 63-66, 136-139 and 177-181 (numbering of amino acids according to SEQ ID NO:22). It is preferred that the papain from *Carica papaya* or a derivative or homologue thereof is used as the scaffold.

In a further embodiment the protein scaffold belongs to the C2 class of cysteine proteases or has at least 70% identity on the amino acid level to a protein of the C2 class of cysteine proteases and/or has a tertiary structure similar to human calpain-2. It is preferred that SDRs are inserted into the protein scaffold at one or more positions from the group of positions that correspond structurally or by amino acid sequence homology to the regions 90-103, 160-172, 193-199, 243-260, 286-294 and 316-322 in human calpain-2, and more preferably at one or more positions from the group of positions that correspond structurally or by amino acid sequence homology to the regions 92-101, 245-250 and 287-291 (numbering of amino acids according to SEQ ID NO:23). It is preferred that the human calpain-2 or a derivative or homologue thereof is used as the scaffold.

In a further embodiment the protein scaffold belongs to the C4 class of cysteine proteases or has at least 70% identity on the amino acid level to a protein of the C4 class of cysteine proteases and/or has a tertiary structure similar to NIa protease from tobacco etch virus. It is preferred that SDRs are inserted into the protein scaffold at one or more positions from the group of positions that correspond structurally or by amino acid sequence homology to the regions 23-31, 112-120, 144-150, 168-176 and 205-218 in NIa protease from tobacco etch virus, and more preferably at one or more positions from the group of positions that correspond structurally or by amino acid sequence homology to the regions 145-149, 169-174 and 212-218 (numbering of amino acids according to SEQ ID NO:24). It is preferred that the NIa protease from tobacco etch virus (TEV protease) or a derivative or homologue thereof is used as the scaffold.

In a further embodiment the protein scaffold belongs to the C10 class of cysteine proteases or has at least 70% identity on the amino acid level to a protein of the C10 class of cysteine proteases and/or has a tertiary structure similar to the streptopain from *Streptococcus pyogenes*. It is preferred that SDRs are inserted into the protein scaffold at one or more positions from the group of positions that correspond structurally or by amino acid sequence homology to the regions 81-90, 133-140, 150-164, 191-199, 219-229, 246-256, 306-312 and 330-337 in streptopain from *Streptococcus pyogenes*, and more preferably at one or more positions from the group of positions that correspond structurally or by amino acid sequence homology to the regions 82-87, 134-138, 250-254 and 331-335 (numbering of amino acids according to SEQ ID NO:25). It is preferred that the streptopain from *Streptococcus pyogenes* or a derivative or homologue thereof is used as the scaffold.

In a further embodiment the protein scaffold belongs to the C19 class of cysteine proteases or has at least 70% identity on the amino acid level to a protein of the C19 class of cysteine proteases and/or has a tertiary structure similar to human ubiquitin specific protease 7. It is preferred that SDRs are inserted into the protein scaffold at one or more positions from the group of positions that correspond structurally or by amino acid sequence homology to the regions 3-15, 63-70, 80-86, 248-256, 272-283 and 292-304 in human ubiquitin specific protease 7, and more preferably at one or more positions from the group of positions that correspond structurally or by amino acid sequence homology to the regions 10-15, 251-255, 277-281 and 298-304 (numbering of amino acids according to SEQ ID NO:26). It is preferred that the human ubiquitin specific protease 7 or a derivative or homologue thereof is used as the scaffold.

In a further embodiment the protein scaffold belongs to the C47 class of cysteine proteases or has at least 70% identity on the amino acid level to a protein of the C47 class of cysteine proteases and/or has a tertiary structure similar to the staphopain from *Staphylococcus aureus*. It is preferred that SDRs are inserted into the protein scaffold at one or more positions from the group of positions that correspond structurally or by amino acid sequence homology to the regions 15-23, 57-66, 108-119, 142-149 and 157-164 in staphopain from *Staphylococcus aureus*, and more preferably at one or more positions from the group of positions that correspond structurally or by amino acid sequence homology to the regions 17-22, 111-117, 143-147 and 159-163 (numbering of amino acids according to SEQ ID NO:27). It is preferred that the staphopain from *Staphylococcus aureus* or a derivative or homologue thereof is used as the scaffold.

In a further embodiment the protein scaffold belongs to the C48 class of cysteine proteases or has at least 70% identity on the amino acid level to a protein of the C48 class of cysteine proteases and/or has a tertiary structure similar to the Ulp1 endopeptidase from *Saccharomyces cerevisiae*. It is preferred that SDRs are inserted into the protein scaffold at one or more positions from the group of positions that correspond structurally or by amino acid sequence homology to the regions 40-51, 108-115, 132-141, 173-179 and 597-605 in Ulp1 endopeptidase from *Saccharomyces cerevisiae*, and more preferably at one or more positions that correspond structurally or by amino acid sequence homology to the regions 43-49, 110-113, 133-137 and 175-178 (numbering of amino acids according to SEQ ID NO:28). It is preferred that the Ulp1 endopeptidase from *Saccharomyces cerevisiae* or a derivative or homologue thereof is used as the scaffold.

In a further embodiment the protein scaffold belongs to the C56 class of cysteine proteases or has at least 70% identity on the amino acid level to a protein of the C56 class of cysteine proteases and/or has a tertiary structure similar to the Pfp1 endopeptidase from *Pyrococcus horikoshii*. It is preferred that SDRs are inserted into the protein scaffold at one or more positions from the group of positions that correspond structurally or by amino acid sequence homology to the regions 8-16, 40-47, 66-73, 118-125 and 147-153 in Pfp1 endopeptidase from *Pyrococcus horikoshii*, and more preferably at one or more positions from the group of positions that correspond structurally or by amino acid sequence homology to the regions 9-14, 68-71, 120-123 and 148-151 (numbering of amino acids according to SEQ ID NO:29). It is preferred that the Pfp1 endopeptidase from *Pyrococcus horikoshii* or a derivative or homologue thereof is used as the scaffold.

In a further embodiment the protein scaffold belongs to the M4 class of metallo proteases or has at least 70% identity on the amino acid level to a protein of the M4 class of metallo proteases and/or has a tertiary structure similar to thermolysin from *Bacillus thermoproteolyticus*. It is preferred that SDRs are inserted into the protein scaffold at one or more positions from the group of positions that correspond structurally or by amino acid sequence homology to the regions 106-118, 125-130, 152-160, 197-204, 210-213 and 221-229 in thermolysin from *Bacillus thermoproteolyticus*, and more preferably at one or more positions from the group of positions that correspond structurally or by amino acid sequence homology to the regions 108-115, 126-129, 199-203 and 223-227 (numbering of amino acids according to SEQ ID NO:30). It is preferred that the thermolysin from *Bacillus thermoproteolyticus* or a derivative or homologue thereof is used as the scaffold.

In a further embodiment the protein scaffold belongs to the M10 class of metallo proteases or has at least 70% identity on the amino acid level to a protein of the M10 class of metallo proteases and/or has a tertiary structure similar to human collagenase. It is preferred that SDRs are inserted into the protein scaffold at one or more positions from the group of positions that correspond structurally or by amino acid sequence homology to the regions 2-7, 68-79, 85-90, 107-111 and 135-141 in human collagenase, and more preferably at one or more positions from the group of positions that correspond structurally or by amino acid sequence homology to the regions 3-6, 71-78 and 136-140 (numbering of amino acids according to SEQ ID NO:31). It is preferred that human collagenase or a derivative or homologue thereof is used as the scaffold.

It is further preferred that the engineered enzymes have glycosidase activity. A particularly suited protein scaffold for this variant is a glycosylase or is derived from a glycosylase. Preferably, the tertiary structure belongs to one of the following structural classes: class GH13, GH7, GH12, GH11, GH10, GH28, GH26, and GH18 (beta/alpha)8 barrel.

In a first embodiment the protein scaffold belongs to the GH13 class of glycosylases or has at least 70% identity on the amino acid level to a protein of the GH13 class of glycosylases and/or has a tertiary structure similar to human pancreatic alpha-amylase. It is preferred that SDRs are inserted into the protein scaffold at one or more positions from the group of positions that correspond structurally or by amino acid sequence homology to the regions 50-60, 100-110, 148-167, 235-244, 302-310 and 346-359 in human pancreatic alpha-amylase, and more preferably at one or more positions from the group of positions that correspond structurally or by amino acid sequence homology to the regions 51-58, 148-155 and 303-309 (numbering of amino acids according to SEQ ID NO:32). It is preferred that human pancreatic alpha-amylase or a derivative or homologue thereof is used as the scaffold.

In a further embodiment the protein scaffold belongs to the GH7 class of glycosylases or has at least 70% identity on the amino acid level to a protein of the GH7 class of glycosylases and/or has a tertiary structure similar to cellulase from *Trichoderma reesei*. It is preferred that SDRs are inserted into the protein scaffold at one or more positions from the group of positions that correspond structurally or by amino acid sequence homology to the regions 47-56, 93-104, 173-182, 215-223, 229-236 and 322-334 in cellulase from *Trichoderma reesei*, and more preferably at one or more positions from the group of positions that correspond structurally or by amino acid sequence homology to the regions 175-180, 218-222 and 324-332 (numbering of amino acids according to SEQ ID NO:33). It is preferred that cellulase from *Trichoderma reesei* or a derivative or homologue thereof is used as the scaffold.

In a further embodiment the protein scaffold belongs to the GH12 class of glycosylases or has at least 70% identity on the amino acid level to a protein of the GH12 class of glycosylases and/or has a tertiary structure similar to cellulase from *Aspergillus niger*. It is preferred that SDRs are inserted into the protein scaffold at one or more positions from the group of positions that correspond structurally or by amino acid sequence homology to the regions 18-28, 55-60, 106-113, 126-132 and 149-159 in cellulase from *Aspergillus niger*, and more preferably at one or more positions from the group of positions that correspond structurally or by amino acid sequence homology to the regions 20-26, 56-59, 108-112 and 151-156 (numbering of amino acids according to SEQ ID NO:34). It is preferred that cellulase from *Aspergillus niger* or a derivative or homologue thereof is used as the scaffold.

In a further embodiment the protein scaffold belongs to the GH11 class of glycosylases or has at least 70% identity on the amino acid level to a protein of the GH11 class of glycosylases and/or has a tertiary structure similar to xylanase from *Aspergillus niger*. It is preferred that SDRs are inserted into the protein scaffold at one or more positions from the group of positions that correspond structurally or by amino acid sequence homology to the regions 7-14, 33-39, 88-97, 114-126 and 158-167 in xylanase from *Aspergillus niger*, and more preferably at one or more positions from the group of positions that correspond structurally or by amino acid sequence homology to the regions 20-26, 56-59, 108-112 and 151-156 (numbering of amino acids according to SEQ ID NO:35). It is preferred that xylanase from *Aspergillus niger* or a derivative or homologue thereof is used as the scaffold.

In a further embodiment the protein scaffold belongs to the GH10 class of glycosylases or has at least 70% identity on the amino acid level to a protein of the GH10 class of glycosylases and/or has a tertiary structure similar to xylanase from *Streptomyces lividans*. It is preferred that SDRs are inserted into the protein scaffold at one or more positions from the group of positions that correspond structurally or by amino acid sequence homology to the regions 21-29, 42-50, 84-92, 130-136, 206-217 and 269-278 in xylanase from *Streptomyces lividans*, and more preferably at one or more positions from the group of positions that correspond structurally or by amino acid sequence homology to the regions 43-49, 86-90, 208-213 and 271-276 (numbering of amino acids according to SEQ ID NO:36). It is preferred that xylanase from *Streptomyces lividans* or a derivative or homologue thereof is used as the scaffold.

In a further embodiment the protein scaffold belongs to the GH28 class of glycosylases or has at least 70% identity on the amino acid level to a protein of the GH28 class of glycosylases and/or has a tertiary structure similar to pectinase from *Aspergillus niger*. It is preferred that SDRs are inserted into the protein scaffold at one or more positions from the group of positions that correspond structurally or by amino acid sequence homology to the regions 82-88, 118-126, 171-178, 228-236, 256-264 and 289-299 in pectinase from *Aspergillus niger*, and more preferably at one or more positions from the group of positions that correspond structurally or by amino acid sequence homology to the regions 116-124, 174-178 and 291-296 (numbering of amino acids according to SEQ ID NO:37). It is preferred that pectinase from *Aspergillus niger* or a derivative or homologue thereof is used as the scaffold.

In a further embodiment the protein scaffold belongs to the GH26 class of glycosylases or has at least 70% identity on the amino acid level to a protein of the GH26 class of glycosylases and/or has a tertiary structure similar to mannanase from *Pseudomonas cellulosa*. It is preferred that SDRs are inserted into the protein scaffold at one or more positions from the group of positions that correspond structurally or by amino acid sequence homology to the regions 75-83, 113-125, 174-182, 217-224, 247-254, 324-332 and 325-340 in mannanase from *Pseudomonas cellulosa*, and more preferably at one or more positions from the group of positions that correspond structurally or by amino acid sequence homology to the regions 115-123, 176-180, 286-291 and 328-337 (numbering of amino acids according to SEQ ID NO:38). It is preferred that mannanase from *Pseudomonas cellulosa* or a derivative or homologue thereof is used as the scaffold.

In an further embodiment the protein scaffold belongs to the GH18 (beta/alpha)8 barrel class of glycosylases or has at least 70% identity on the amino acid level to a protein of the GH18 class of glycosylases and/or has a tertiary structure similar to chitinase from *Bacillus circulans*. It is preferred that SDRs are inserted into the protein scaffold at one or more positions from the group of positions that correspond structurally or by amino acid sequence homology to the regions 21-29, 57-65, 130-136, 176-183, 221-229, 249-257 and 327-337 in chitinase from *Bacillus circulans*, and more preferably at one or more positions from the group of positions that correspond structurally or by amino acid sequence homology to the regions 59-63, 178-181, 250-254 and 330-336 (numbering of amino acids according to SEQ ID NO:39). It is preferred that chitinase from *Bacillus circulans* or a derivative or homologue thereof is used as the scaffold.

It is further preferred that the engineered enzymes have esterhydrolase activity. Preferably, the protein scaffold for this variant have lipase, phosphatase, phytase, or phosphodiesterase activity.

In a first embodiment the protein scaffold belongs to the GX class of esterases or has at least 70% identity on the amino acid level to a protein of the GX class of esterases and/or has a tertiary structure similar to the structure of the lipase B from *Candida antarctica*. Preferably, the scaffold has lipase activity. It is preferred that SDRs are inserted into the protein scaffold at one or more positions from the group of positions that correspond structurally or by amino acid sequence homology to the regions 139-148, 188-195, 216-

224, 256-266, 272-287 in lipase B from *Candida antarctica*, and more preferably at one or more positions from the group of positions that correspond structurally or by amino acid sequence homology to the regions 141-146, 218-222, 259-263 and 275-283 (numbering of amino acids according to SEQ ID NO:40). It is preferred that lipase B from *Candida antarctica* or a derivative or homologue thereof is used as the scaffold.

In a further embodiment the protein scaffold belongs to the GX class of esterases or has at least 70% identity on the amino acid level to a protein of the GX class of esterases and/or has a tertiary structure similar to the pancreatic lipase from guinea pig. Preferably, the scaffold has lipase activity. It is preferred that SDRs are inserted into the protein scaffold at one or more positions from the group of positions that correspond structurally or by amino acid sequence homology to the regions 78-90, 91-100, 112-120, 179-186, 207-218, 238-247 and 248-260 in pancreatic lipase from guinea pig, and more preferably at one or more positions from the group of positions that correspond structurally or by amino acid sequence homology to the regions 80-87, 114-118, 209-215 and 239-246 (numbering of amino acids according to SEQ ID NO:41). It is preferred that pancreatic lipase from guinea pig or a derivative or homologue thereof is used as the scaffold.

In a further embodiment the protein scaffold has a tertiary structure similar to the structure of the alkaline phosphatase from *Escherichia coli* or has at least 70% identity on the amino acid level to a protein that has a tertiary structure similar to the structure of the alkaline phosphatase from *Escherichia coli*. Preferably, the scaffold has phosphatase activity. It is preferred that SDRs are inserted into the protein scaffold at one or more positions from the group of positions that correspond structurally or by amino acid sequence homology to the regions 110-122, 187-142, 170-175, 186-193, 280-287 and 425-435 in alkaline phosphatase from *Escherichia coli*, and more preferably at one or more positions from the group of positions that correspond structurally or by amino acid sequence homology to the regions 171-174, 187-191, 282-286 and 426-433 (numbering of amino acids according to SEQ ID NO:42). It is preferred that alkaline phosphatase from *Escherichia coli* or a derivative or homologue thereof is used as the scaffold.

In a further embodiment the protein scaffold has a tertiary structure similar to the structure of the bovine pancreatic desoxyribonuclease I or has at least 70% identity on the amino acid level to a protein that has a tertiary structure similar to the structure of the bovine pancreatic desoxyribonuclease I. Preferably, the scaffold has phosphodiesterase activity. More preferably, a nuclease, and most preferably, an unspecific endonuclease or a derivative thereof is used as the scaffold. It is preferred that SDRs are inserted into the protein scaffold at one or more positions from the group of positions that correspond structurally or by amino acid sequence homology to the regions 14-21, 41-47, 72-77, 97-111, 135-143, 171-178, 202-209 and 242-251 in bovine pancreatic desoxyribonuclease I, and more preferably at one or more positions from the group of positions that correspond structurally or by amino acid sequence homology to the regions 16-19, 42-46, 136-141 and 172-176 (numbering of amino acids according to SEQ ID NO:43). It is preferred that bovine pancreatic desoxyribonuclease I or human desoxyribonuclease I or a derivative or homologue thereof is used as the scaffold.

It is further preferred that the engineered enzyme has transferase activity. A particularly suited protein scaffold for this variant is a glycosyl-, a phospho- or a methyltransferase, or is a derivative thereof. Particularly preferred protein scaffolds for this variant are glycosyltransferases or are derived from glycosyltransferases. The tertiary structure of the protein scaffold can be of any type. Preferably, however, the tertiary structure belongs to one of the following structural classes: GH13 and GT1.

In a first embodiment the protein scaffold belongs to the GH13 class of transferases or has at least 70% identity on the amino acid level to a protein of the GH13 class of transferases and/or has a tertiary structure similar to the structure of the cyclomaltodextrin glucanotransferase from *Bacillus circulans*. Preferably, the scaffold has transferase activity, and more preferably a glycosyltransferase is used as the scaffold. It is preferred that SDRs are inserted into the protein scaffold at one or more positions from the group of positions that correspond structurally or by amino acid sequence homology to the regions 38-48, 85-94, 142-154, 178-186, 259-266, 331-340 and 367-377 in cyclomaltodextrin glucanotransferase from *Bacillus circulans*, and more preferably at one or more positions from the group of positions that correspond structurally or by amino acid sequence homology to the regions 87-92, 180-185, 261-264 and 269-275 (numbering of amino acids according to SEQ ID NO:44). It is preferred that cyclomaltodextrin glucanotransferase from *Bacillus circulans* or a derivative or homologue thereof is used as the scaffold.

In a further embodiment the protein scaffold belongs to the GT1 class of tranferases or has at least 70% identity on the amino acid level to a protein of the GT1 class of transferases and/or has a tertiary structure similar to the structure of the glycosyltransferase from *Amycolatopsis orientalis* A82846. Preferably the scaffold has transferase activity, and more preferably glycosyltransferase activity. It is preferred that SDRs are inserted into the protein scaffold at one or more positions from the group of positions that correspond structurally or by amino acid sequence homology to the regions 58-74, 130-138, 185-193, 228-236 and 314-323 in glycosyltransferase from *Amycolatopsis orientalis* A82846, and more preferably at one or more positions from the group of positions that correspond structurally or by amino acid sequence homology to the regions 61-71, 230-234 and 316-321 (numbering of amino acids according to SEQ ID NO:45). It is preferred that the glycosyltransferase from *Amycolatopsis orientalis* A82846 or a derivative or homologue thereof is used as the scaffold.

It is further preferred that the engineered enzymes have oxidoreductase activity. A particularly suited protein scaffold for this variant is a monooxygenase, a dioxygenase or a alcohol dehydrogenase, or a derivative thereof. The tertiary structure of the protein scaffold can be of any type.

In a first embodiment the protein scaffold has a tertiary structure similar to the structure of the 2,3-diphydroxybiphenyl dioxygenase from *Pseudomonas* sp. or has at least 70% identity on the amino acid level to a protein that has a tertiary structure similar to the structure of the 2,3-diphydroxybiphenyl dioxygenase from *Pseudomonas* sp. Preferably, the scaffold has dioxygenase activity. It is preferred that SDRs are inserted into the protein scaffold at one or more positions from the group of positions that correspond structurally or by amino acid sequence homology to the regions 172-185, 198-206, 231-237, 250-259 and 282-287 in 2,3-diphydroxybiphenyl dioxygenase from *Pseudomonas* sp., and more preferably at one or more positions from the group of positions that correspond structurally or by amino acid sequence homology to the regions 175-182, 200-204, 252-257 and 284-287 (numbering of amino acids according to SEQ ID NO:46). It is preferred that the 2,3-diphydroxybiphenyl dioxygenase from *Pseudomonas* sp or a derivative or homologue thereof is used as the scaffold.

In a further embodiment the protein scaffold has a tertiary structure similar to the structure of the catechol dioxygenase from *Acinetobacter* sp. or has at least 70% identity on the amino acid level to a protein that has a tertiary structure similar to the structure of the catechol dioxygenase from *Acinetobacter* sp. Preferably, the scaffold has dioxygenase activity, and more preferably catechol dioxygenase activity. It is preferred that SDRs are inserted into the protein scaffold at one or more positions from the group of positions that correspond structurally or by amino acid sequence homology to the regions 66-72, 105-112, 156-171 and 198-207 in catechol dioxygenase from *Acinetobacter* sp., and more preferably at one or more positions from the group of positions that correspond structurally or by amino acid sequence homology to the regions 107-110, 161-171 and 201-205 (numbering of amino acids according to SEQ ID NO:47). It is preferred that the catechol dioxygenase from *Acinetobacter* sp or a derivative or homologue thereof is used as the scaffold.

In a further embodiment the protein scaffold has a tertiary structure similar to the structure of the camphor-5-monooxygenase from *Pseudomonas putida* or has at least 70% identity on the amino acid level to a protein that has a tertiary structure similar to the structure of the camphor-5-monooxygenase from *Pseudomonas putida*. Preferably, the scaffold has monooxygenase activity, and more preferably camphor monooxygenase activity. It is preferred that SDRs are inserted into the protein scaffold at one or more positions from the group of positions that correspond structurally or by amino acid sequence homology to the regions 26-31, 57-63, 84-98, 182-191, 242-256, 292-299 and 392-399 in camphor-5-monooxygenase from *Pseudomonas putida*, and more preferably at one or more positions from the group of positions that correspond structurally or by amino acid sequence homology to the regions 85-96, 183-188, 244-253, 293-298 and 393-398 (numbering of amino acids according to SEQ ID NO:48). It is preferred that the camphor-5-monooxygenase from *Pseudomonas putida* or a derivative or homologue thereof is used as the scaffold.

In a further embodiment the protein scaffold has a tertiary structure similar to the structure of the alcohol dehydrogenase from *Equus callabus* or has at least 70% identity on the amino acid level to a protein that has a tertiary structure similar to the structure of the alcohol dehydrogenase from *Equus callabus*. Preferably, the scaffold has alcohol dehydrogenase activity. It is preferred that SDRs are inserted into the protein scaffold at one or more positions from the group of positions that correspond structurally or by amino acid sequence homology to the regions 49-63, 111-112, 294-301 and 361-369 in alcohol dehydrogenase from *Equus callabus*, and more preferably at one or more positions from the group of positions that correspond structurally or by amino acid sequence homology to the regions 51-61 and 295-299 (numbering of amino acids according to SEQ ID NO:49). It is preferred that the alcohol dehydrogeriase from *Equus callabus* or a derivative or homologue thereof is used as the scaffold.

It is further preferred that the engineered enzymes have lyase activity. A particularly suited protein scaffold for this variant is a oxoacid lyase or is a derivative thereof. Particularly preferred protein scaffolds for this variant are aldolases or synthases, or are derived thereof. The tertiary structure of the protein scaffold can be of any type, but a (beta/alpha)8 barrel structure is preferred.

In a first embodiment the protein scaffold has a tertiary structure similar to the structure of the N-acetyl-d-neuramic acid aldolase from *Escherichia coli* or has at least 70% identity on the amino acid level to a protein that has a tertiary structure similar to the structure of the N-acetyl-d-neuramic acid aldolase from *Escherichia coli*. Preferably, the scaffold has aldolase activity. It is preferred that SDRs are inserted into the protein scaffold at one or more positions from the group of positions that correspond structurally or by amino acid sequence homology to the regions 45-55, 78-87, 105-113, 137-146, 164-171, 187-193, 205-210, 244-255 and 269-276 in N-acetyl-d-neuramic acid aldolase from *Escherichia coli*, and more preferably at one or more positions from the group of positions that correspond structurally or by amino acid sequence homology to the regions 45-52, 138-144, 189-192, 247-253 and 271-275 (numbering of amino acids according to SEQ ID NO:50). It is preferred that the N-acetyl-d-neuramic acid aldolase from *Escherichia coli* or a derivative or homologue thereof is used as the scaffold.

In a further embodiment the protein scaffold has a tertiary structure similar to the structure of the tryptophan synthase from *Salmonella typhimurium* or has at least 70% identity on the amino acid level to a protein that has a tertiary structure similar to the structure of the tryptophan synthase from *Salmonella typhimurium*. Preferably, the scaffold has synthase activity. It is preferred that SDRs are inserted into the protein scaffold at one or more positions from the group of positions that correspond structurally or by amino acid sequence homology to the regions 56-63, 127-134, 154-161, 175-193, 209-216 and 230-240 in tryptophan synthase from *Salmonella typhimurium*, and more preferably at one or more positions from the group of positions that correspond structurally or by amino acid sequence homology to the regions 57-62, 155-160, 178-190 and 210-215 (numbering of amino acids according to SEQ ID NO:51). It is preferred that the tryptophan synthase from *Salmonella typhimurium* or a derivative or homologue thereof is used as the scaffold.

It is further preferred that the engineered enzymes have isomerase activity. A particularly suited protein scaffold for this variant is a converting aldose or a converting ketose, or is a derivative thereof.

In a first embodiment, the protein scaffold has a tertiary structure similar to the structure of the xylose isomerase from *Actinoplanes missouriensis* or has at least 70% identity on the amino acid level to a protein that has a tertiary structure similar to the structure of the xylose isomerase from *Actinoplanes missouriensis*. It is preferred that SDRs are inserted into the protein scaffold at one or more positions from the group of positions that correspond structurally or by amino acid sequence homology to the regions 18-31, 92-103, 136-147, 178-188 and 250-257 in xylose isomerase from *Actinoplanes missouriensis*, and more preferably at one or more positions from the group of positions that correspond structurally or by amino acid sequence homology to the regions 20-27, 92-99 and 180-186 (numbering of amino acids according to SEQ ID NO:52). It is preferred that the xylose isomerase from *Actinoplanes missouriensis* or a derivative or homologue thereof is used as the scaffold.

It is further preferred that the engineered enzymes have ligase activity. A particularly suited protein scaffold for this variant is a DNA ligase, or is a derivative thereof.

In a first embodiment, the protein scaffold has a tertiary structure similar to the structure of the DNA ligase from Bacteriophage T7 or has at least 70% identity on the amino acid level to a protein that has a tertiary structure similar to the structure of the DNA-ligase from Bacteriophage T7. It is preferred that SDRs are inserted into the protein scaffold at one or more positions from the group of positions that correspond structurally or by amino acid sequence homology to the regions 52-60, 94-108, 119-131, 241-248, 255-263 and 302-318 in DNA ligase from Bacteriophage T7, and more preferably at one or more positions from the group of positions that correspond structurally or by amino acid sequence homology to the regions 96-106, 121-129, 256-262 and 304-316 (numbering of amino acids according to SEQ ID NO:53). It is preferred that the DNA ligase from Bacteriophage T7 or a derivative or homologue thereof is used as the scaffold.

A second aspect of the invention is directed to the application of engineered enzymes with specificities for therapeutic, research, diagnostic, nutritional, personal care or industrial purposes. The application comprises at least the following steps:
- (a) identification of a target peptide substrate whose hydrolysis has a positive effect in connection with the intended purpose, such as curing a disease, diagnosing a disease, processing of ingredients for human or animal nutrition, or other technical processes;
- (b) provision of an engineered enzyme, the enzyme being specific for the target peptide identified in step (a); and
- (c) use of the enzyme as provided in step (b) for the intended purpose.

In a first variant of this aspect of the invention, the engineered enzyme is used as a therapeutic means to inactivate a disease-related target substrate. This application comprises at least the following steps:
- (a) identification of a target substrate whose function is connected to a disease and whose inactivation has a positive effect in connection with the disease, and determination of a target site within the target substrate characterized by the fact that modification at the target site leads to the inactivation of the target substrate;
- (b) provision of an engineered enzyme, the enzyme being specific for the target site identified in step (a); and
- (c) use of the enzyme for the inactivation of the target substrate inside or outside the human body.

In a preferred embodiment the scaffold of the engineered enzyme provided in step (c) is of human origin in order to avoid or reduce immunogenicity or allergenic effects associated with the application of the enzyme in the human body. In a more preferred embodiment of this variant, the scaffold is of a human protease and the modification is hydrolysis of a target site in a protein target. Preferably, the hydrolysis leads to the activation or inactivation of the peptide or protein target. Potential peptide or protein targets include: cytokines, growth factors, peptide hormones, interleukins, interferons, enzymes from the coagulation cascade, serpins, immunoglobulins, soluble or membrane-bound receptors, cellular or viral surface proteins, peptide drugs, protein drugs.

A particularly preferred embodiment is based on the finding that the engineered enzyme is capable for the cleavage of human tumor nekrose factor-alpha (TNF-α). The engineered enzymes or the fusion protein can thus be used for preparing medicaments for the treatment of inflammatory diseases (as well as other diseases connected with TNF-α). Preferably, said engineered enzyme or said fusion protein is capable of specifically inactivating human tumor nekrose factor-alpha (hTNF-α), more preferably said engineered enzyme or said fusion protein is capable of hydrolysing the peptide bond between positions 31/32, 32/33, 44/45, 87/88, 128/129 and/or 141/142 (most preferred between positions 31/32 and 32/33) in hTNF-α (SEQ ID NO:96).

In a further embodiment, the target substrate is a pro-drug which is activated by the engineered enzyme. In a particular embodiment of this variant, the engineered enzyme has proteolytic activity and the target substrate is a protein target which is proteolytically activated. Examples of such pro-drugs are pro-proteins such as the inactivated forms of coagulations factors. In another particular variant, the engineered enzyme is an oxidoreductase and the target substrate is a chemical that can be activated by oxidation.

In a second variant of this aspect of the invention, the engineered enzyme is used as a technical means in order to catalyze an industrially or nutritionally relevant reaction with defined specificity. In a particular embodiment of this variant the engineered enzyme has proteolytic activity, the catalyzed reaction is a proteolytic processing, and the engineered enzyme specifically hydrolyses one or more industrially or nutrionally relevant protein substrates. In a preferred embodiment of this variant the engineered enzyme hydrolyses one or more industrially or nutrionally relevant protein substrates at specific sites, thereby leading to industrially or nutrionally desired product properties such as texture, taste or precipitation characteristics. In a further particular embodiment of this variant, the engineered enzyme catalyzes the hydrolysis of glycosidic bonds (glycosidase or glycosylases activity). Then, preferably, the catalyzed reaction is a polysaccharide processing, and the engineered enzyme specifically hydrolyses one or more industrially, technically or nutrionally relevant polysaccharide substrates. In a further particular embodiment of this variant, the engineered enzyme catalyzes the hydrolysis of triglyceride esters or lipids (lipase activity). Then, preferably, the catalyzed reaction is a lipid processing step, and the engineered enzyme specifically hydrolyses one or more industrially, technically or nutrionally relevant lipid substrates. In a further particular variant of this embodiment, the engineered enzyme catalyzes the oxidation or reduction of substrates (oxidoreductase activity). Then, preferably, the engineered enzyme specifically oxidizes or reduces one or more industrially, technically or nutrionally relevant chemical substrates.

A third aspect of the invention is directed to a method for generating engineered enzymes with specificities that are qualitatively and/or quantitatively novel in combination with the protein scaffold. The inventive method comprises at least the following steps:
- (a) providing a protein scaffold capable to catalyze at least one chemical reaction on at least one target substrate,
- (b) generating a library of engineered enzymes or isolated engineered enzymes by combining the protein scaffold from step (a) with one or more fully or partially random peptide sequences at sites in the protein scaffold that enable the resulting engineered enzyme to discriminate between at least one target substrate and one or more different substrates and
- (c) selecting out of the library of engineered enzymes generated in step (b) one or more enzymes that have defined specificities towards at least one target substrate.

In a first variant of this aspect of the invention, the inventive method comprises at least the following steps:
- (a) providing a protein scaffold capable to catalyze at least one chemical reaction on at least one target substrate,
- (b) generating a library of engineered enzymes or isolated engineered enzymes by inserting into the protein scaffold from step (a) one or more fully or partially random peptide sequences at sites in the protein scaffold that enable the resulting engineered enzyme to discriminate between at least one target substrate and one or more different substrates and (c) selecting out of the library of engineered enzymes generated in step (b) one or more enzymes that have defined specificities towards at least one target substrate.

Preferably, the positions at which the one or more fully or partially random peptide sequences are combined with or inserted into the protein scaffold are identified prior to the combination or insertion.

The number of insertions or other combinations of fully or partially random peptide sequences as well as their length may vary over a wide range. The number is at least one, preferably more than one, more preferably between two and eleven, most preferably between two and six. The length of such fully or partially random peptide sequences is usually less than 50 amino acid residues. Preferably, the length is between one and 15 amino acid residues, more preferably between one and six amino acid residues. Alternatively, the length is between two and 20 amino acid residues, preferably between two and ten amino acid residues, more preferably between three and eight amino acid residues.

Preferably such insertions or other combinations are performed on the DNA level, using polynucleotides encoding such protein scaffolds and polynucleotides or oligonucleotides encoding such fully or partially random peptide sequences.

Optionally, steps (a) to (c) are repeated cyclically, whereby enzymes selected in step (c) serve as the protein scaffold in step (a) of a further cycle, and randomized peptide sequences are either inserted or, alternatively, substituted for peptide sequences that have been inserted in former cycles. Thereby, the number of inserted peptide sequences is either constant or increases over the cycles. The cycles are repeated until one or more enzymes with the intended specificities are generated.

Moreover, during or after one or more rounds of steps (a) to (c), the scaffold may be mutated at one or more positions in order to make the scaffold more acceptable for the combination with SDR sequences, and/or to increase catalytic activity at a specific pH and temperature, and/or to change the glycosylation pattern, and/or to decrease sensitivity towards enzyme inhibitors, and/or to change enzyme stability.

In a second variant of this aspect of the invention, the inventive method comprises at least the following steps:

(a) providing a first protein scaffold fragment,
(b) connecting said protein scaffold fragment via a peptide linkage with a first SDR, and optionally
(c) connecting the product of step (b) via a peptide linkage with a further SDR peptide or with a further protein scaffold fragment, and optionally
(d) repeating step (c) for as many cycles as necessary in order to generate a sufficiently specific enzyme, and
(e) selecting out of the population generated in steps (a)-(d) one or more enzymes that have the desired specificities toward the one or more target substrates.

Protein scaffold fragment means a part of the sequence of a protein scaffold. A protein scaffold is comprised of at least two protein scaffold fragments.

In a third variant of this aspect of the invention, the protein scaffold, the SDRs and the engineered enzyme are encoded by a DNA sequence and an expression system is used in order to produce the protein. In an alternative variant, the protein scaffold, the SDRs and/or the engineered enzyme are chemically synthesized from peptide building blocks.

In a fourth variant of this aspect of the invention, the inventive method comprises at least the following steps:

(a) providing a polynucleotide encoding a protein scaffold capable of catalyzing one or more chemical reactions on one or more target substrates;
(b) combining one or more fully or partially random oligonucleotide sequence with the polynucleotide encoding the protein scaffold, the fully or partially random oligonucleotide sequences being located at sites in the polynucleotide that enable the encoded engineered enzyme to discriminate between the one or more target substrates and one or more other substrates; and
(c) selecting out of the population generated in step (b) one or more polynucleotides that encode enzymes that have the defined specificities toward the one or more target substrates.

Any enzyme can serve as the protein scaffold in step (a). It can be a naturally occurring enzyme, a variant or a truncated derivate therefore, or an engineered enzyme. For human therapeutic use, the protein scaffold is preferably a mammalian enzyme, and more preferably a human enzyme. In that aspect, the invention is directed to a method for the generation of essentially mammalian, especially of essentially human enzymes with specificities that are different from specificities of any enzyme encoded in mammalian genomes or in the human genome, respectively.

According to the invention, the protein scaffold provided in step (a) of this aspect requires to be capable of catalyzing one or more chemical reactions on a target substrate. Therefore, a protein scaffold is selected from the group of potential protein scaffolds by its activity on the target substrate.

In a preferred variant of this aspect of the invention, a protein scaffold with hydrolase activity is used. Preferably, a protein scaffold with proteolytic activity is used, and more preferably, a protease with very low specificity having basic activity on the target substrate is used as the protein scaffold. Examples of proteases from different structural classes with low substrate specificity are Papain, Trypsin, Chymotrypsin, Subtilisin, SET (trypsin-like serine protease from *Streptomyces erythraeus*), Elastase, Cathepsin G or Chymase. Before being employed as the protein scaffold, the amino acid sequence of the protease may be modified in order to change protein properties other than specificity, e.g catalytic activity, stability, inhibitor sensitivity, or expression yield, essentially as described in WO 92/18645, or in order to change specificity, essentially as described in EP 02020576.3 and PCT/EP03/04864.

Another option for a feasible protein scaffold are lipases. Hepatic lipase, lipoprotein lipase and pancreatic lipase belong to the "lipoprotein lipase superfamily", which in turn is an example of the GX-class of lipases (M. Fischer, J. Pleiss (2003), Nucl. Acid. Res., 31, 319-321). The substrate specificity of lipases can be characterized by their relative activity towards triglycerol esters of fatty acids and phospholipids, bearing a charged head group. Alternatively, other hydrolases such as esterases, glycosylases, amidases, or nitrilases may be used as scaffolds.

Transferases are also feasible protein scaffolds. Glycoslytransferases are involved in many biological synthesis involving a variety of donors and acceptors. Alternatively, the protein scaffold may have ligase, lyase, oxidoreductase, or isomerase activity.

In a first embodiment, the one or more fully or partially random peptide sequences are inserted at specific sites in the protein scaffold. These insertion sites are characterized by the fact that the inserted peptide sequences can act as discriminators between different substrates, i.e. as Specificity Determining Regions or SDRs. Such insertion sites can be identified by several approaches. Preferably, insertion sites are identified by analysis of the three-dimensional structure of the protein scaffolds, by comparative analysis of the primary sequences of the protein scaffold with other enzymes having different quantitative specificities, or experimentally by techniques such as alanine scanning, random mutagenesis, or random deletion, or by any combination thereof.

A first approach to identify insertion sites for SDRs bases on the three-dimensional structure of the protein scaffold as it can be obtained by x-ray crystallography or by nuclear magnetic resonance studies. Structural alignment of the protein scaffold in comparison with other enzymes of the same structural class but having different quantitative specificities reveals regions of high structural similarity and regions with low structural similarity. Such an analysis can for example be done using public software such as Swiss PDB viewer (Guex, N. and Peitsch, M. C. (1997) *Electrophoresis* 18, 2714-2723). Regions of low structural similarity are preferred SDR insertion sites.

In a second approach to identify insertion sites for SDRs, three-dimensional structures of the scaffold protein in complex with competitive inhibitors or substrate analogs are analysed. It is assumed that the binding site of a competitive inhibitor significantly overlaps with the binding site of the substrate. In that case, atoms of the protein that are within a certain distance of atoms of the inhibitor are likely to be in a similar distance to the substrate as well. Choosing a short distance, e.g. <5 Å, will result in an ensemble of protein atoms that are in close contact with the substrate. These residues would constitute the first shell contacts and are therefore preferred insertion sites for SDRs. Once first shell contacts have been identified, second shell contacts can be found by repeating the distance analysis starting from first shell atoms. In yet another alternative of the invention the distance analysis described above is performed starting from the active site residues.

In third approach to identify insertion sites for SDRs, the primary sequence of the scaffold protein is aligned with other enzymes of the same structural class but having different quantitative specificities using an alignment algorithm. Examples of such alignment algorithms are published (Altschul, S. F., Gish, W., Miller, W., Myers, E. W. & Lipman, D. J. (1990) J. Mol. Biol. 215:403-410; "Statistical methods in Bioinformatics: an introduction" by Ewens, W. & Grant, G. R. 2001, Springer, New York). Such an alignment may reveal conserved and non-conserved regions with varying sequence homology, and, in particular, additional sequence elements in one or more enzymes compared to the scaffold protein. Conserved regions of are more likely to contribute to phenotypes shared among the different proteins, e.g. stabilizing the three-dimensional fold. Non-conserved regions and, in particular, additional sequences in enzymes with quantitatively higher specificity (Turner, R. et al. (2002) *J. Biol. Chem.*, 277, 33068-33074) are preferred insertion sites for SDRs.

For proteases currently five families are known, namely aspartic-, cysteine-, serine-, metallo- and threonine proteases. Each family includes groups of proteases that share a similar fold. Crystallographic structures of members of these groups have been solved and are accessible through public databases, e.g. the Brookhaven protein database (H. M. Berman et al. *Nucleic Acids Research*, 28 pp. 235-242 (2000)). Such databases also include structural homologs in other enzyme classes and nonenzymatically active proteins of each class. Several tools are available to search public databases for structural homologues: SCOP—a structural classification of proteins database for the investigation of sequences and structures. (Murzin A. G. et al. (1995) *J. Mol. Biol.* 247, 536-540); CATH—Class, Architecture, Topology and Homologous superfamily: a hierarchical classification of protein domain structures (Orengo et al. (1997) *Structure* 5(8) 1093-1108); FSSP—Fold classification based on structure-structure alignment of proteins (Hohm and Sander (1998) *Nucl. Acids Res.* 26 316-319); or VAST—Vector alignment search tool (Gibrat, Madej and Bryant (1996) *Current Opinion in Structural Biology* 6, 377-385).

In the above described approaches, members of structural classes are compared in order to identify insertion sites for SDRs.

In a preferred variant of these approaches serine proteases of the structural class S1 are compared with each other. Trypsin represents a member with low substrate specificity, as it requires only an arginine or lysine residue at the $P_1$ position. On the other hand, thrombin, tissue-type plasminogen activator or enterokinase all have a high specificity towards their substrate sequences, i.e. (L/I/V/F)XPR^NA (SEQ ID NO: 97), CPGR^VVGG (SEQ ID NO: 98) and DDDK^(SEQ ID NO: 99), respectively (Perona, J. & Craik, C. (1997) *J. Bid. Chem.*, 272, 29987-29990; Perona, J. & Craik, C (1995) *Protein Science*, 4, 337-360). An alignment of the amino acid sequences of these proteases is described in example 1 (FIG. 2) along with the identification of SDRs.

Figure 3:
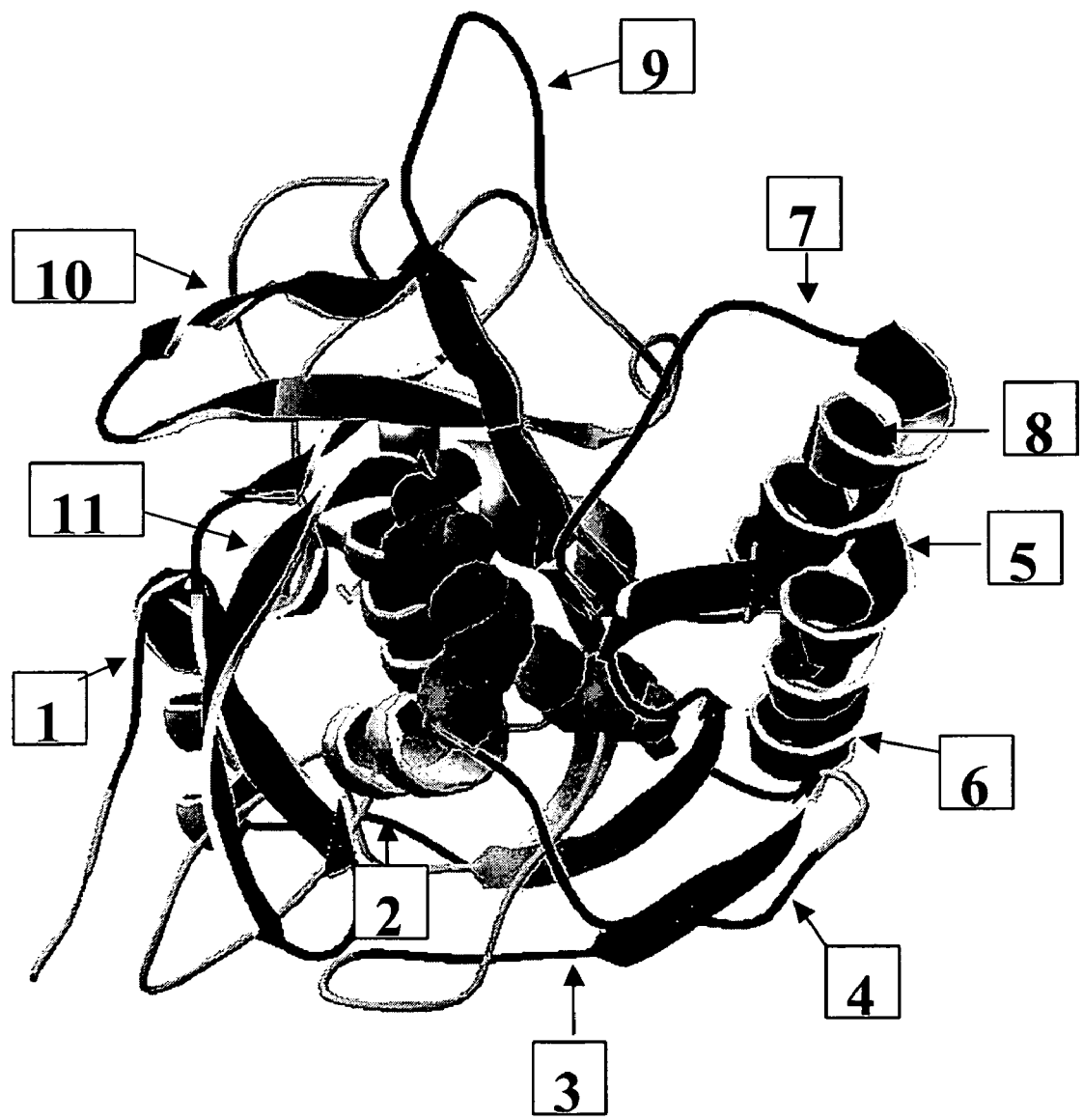
FIG. 3 illustrates the three-dimensional structure of subtilisin with the active site residues being shown in "ball-and-stick" representation and with the numbered regions indicating potential SDR insertion sites.

A further example within the family of serine proteases is given by members of the structural class S8 (subtilisin fold). Subtilisin is the type protease for this class and represents an unspecific protease (Ottesen, M. & Svendsen, A. (1998) *Methods Enzymol.* 19, 199-215). Furin, PC 1 and PC5 are proteases of the same structural class involved in the processing of propeptides and have a high substrate specificity (Seidah, N. & Chretien, M. (1997) Curr. Opin. Biotech., 8: 602-607; Bergeron, F. et al. (2000) *J. Mol. Endocrin.*, 24:1-22). In a preferred variant of the approach alignments of the primary amino acids sequences (FIG. 4) are used to identify eleven sequence stretches longer than three amino acids which specific proteases have in addition compared to subtilisin and are therefore potential specificity determining regions. In a further variant of the approach information from the three-dimensional structure of subtilisin can be used in order to further narrow down the selection (FIG. 3). Out of the eleven inserted sequence stretches, three are especially close to the active site residues, namely stretch number 7, 8 and 11 which are insertions in PC5, PC1 and all three specific proteases, respectively (FIG. 3). In a preferred variant, one or several amino acid stretches of variable length and composition can be inserted into the subtilisin sequence at one or several of the eleven positions. In a more preferred variant of the approach the insertion is performed at regions 7, 8 or 11 or any combination thereof. In another preferred variant of the approach protease scaffolds other than subtilisin from the structural class S8 are used.

In a further preferred variant of this approach, aspartic acid proteases of the structural class A1 are analyzed (Rawlings, N. D. & Barrett, A. J. (1995). *Methods Enzymol.* 248, 105-120; Chitpinityol, S. & Crabbe, M J. (1998), *Food Chemistry*, 61, 395-418). Examples for the A1 structural class of aspartic proteases are pepsin with a low as well as beta-secretase (Grüninger-Leitch, F., et al. (2002) *J. Biol. Chem.* 277, 4687-4693) and renin (Wang, W. & Liang, TC.

Figure 5:
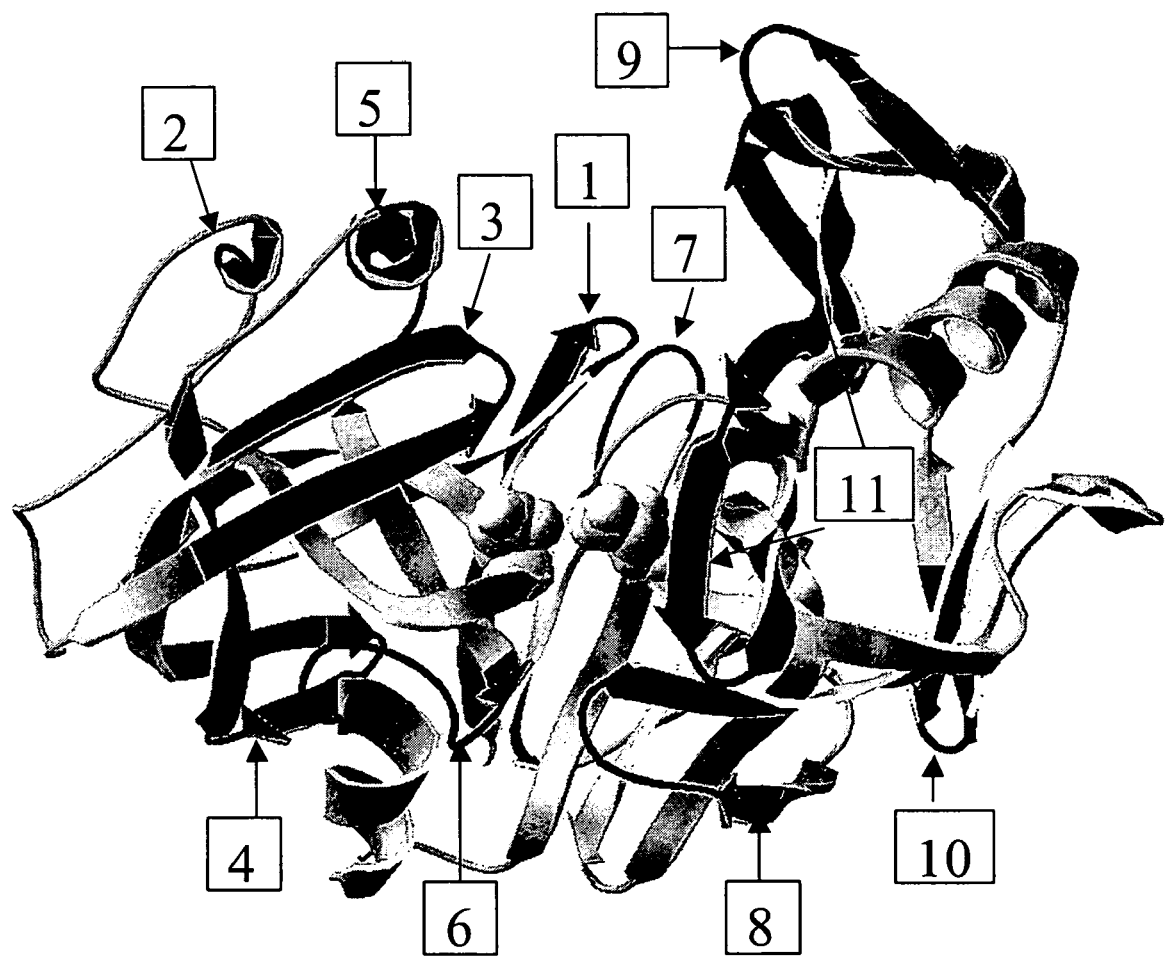
FIG. 5 illustrates the three-dimensional structure of pepsin with the active site residues being shown in "ball-and-stick" representation and with the numbered regions indicating potential SDR insertion sites.

(1994) *Biochemistry*, 33, 14636-14641) with relatively high substrate specificities. Retroviral proteases also belong to this class, although the active enzyme is a dimer of two identical subunits. The viral proteases are essential for the correct processing of the polyprotein precursor to generate functional proteins which requires a high substrate specificity in each case (Wu, J. et al. (1998) *Biochemistry*, 37, 4518-4526; Pettit, S. et al. (1991) J. Biol. Chem., 266, 14539-14547). Pepsin is the type protease for this class and represents an unspecific protease (Kageyama, T. (2002) *Cell. Mol. Life Sci.* 59, 288-306). B-secretase and Cathepsin D (Aguilar, C. F. et al. (1995) *Adv. Exp. Med. Biol.* 362, 155-166) are proteases of the same structural class and have a high substrate specificity. In a preferred variant of the approach alignments of the primary amino acids sequences (FIG. 6) are used to identify six sequence stretches longer than three amino acids which are inserted in the specific proteases compared to pepsin and are therefore potential specificity determining regions. In a further variant of the approach information from the three-dimensional structure of b-secretase can be used in order to further narrow down the selection. Out of the six inserted sequence stretches, three are especially close to the active site residues, namely stretch number 1, 3 and 4 which are insertions in cathepsin D and beta-secretase, respectively (FIG. 5). In a preferred variant of the approach, one or several amino acid stretches of variable length and composition can be inserted into the pepsin sequence at one or several of the six positions. In a more preferred embodiment of the invention the insertion is performed at the positions 1, 3 or 4 or any combination thereof. In another preferred embodiment of the invention protease scaffolds other than pepsin are used.

Figure 7:
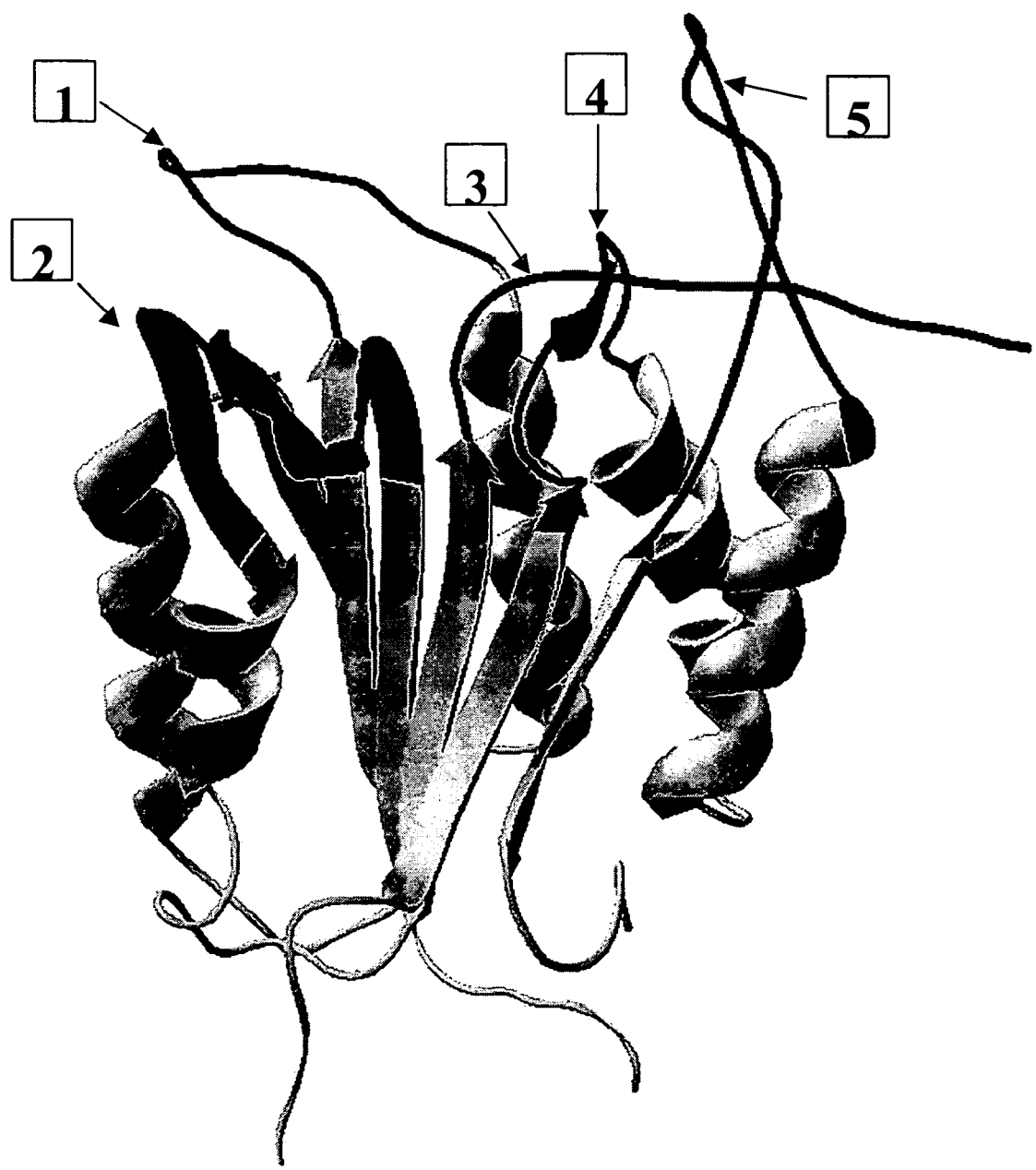
FIG. 7: illustrates the three-dimensional structure of caspase 7 with the active site residues being shown in "ball-and-stick" representation and with the numbered regions indicating potential SDR insertion sites.

There are cases where a certain structural class does not include known members of low and high specificity. This is exemplified by the C14 class of caspases which belong to the cysteine protease family (Rawlings, N. D. & Barrett, A. J. (1994) *Methods Enzymol.* 244, 461-486) and which all show high specificity for $P_4$ to $P_1$ positions. For example, caspase-1, caspase-3 and caspase-9 recognize the sequences YVAD^, DEVD^ or LEHD^, respectively. Identification of the regions that differ between the caspases will include the regions responsible for the differences in substrate specificity (FIGS. 7 and 8).

Finally, non-enzymatic proteins of the same fold as the enzyme scaffold may also contribute to the identification of insertion sites for SDRs. For example, haptoglobin (Arcoleo, J. & Greer, J.; (1982) *J. Biol. Chem.* 257, 10063-10068) and azurocidin (Almeida, R. et al. (1991) Biochem. Biophys. Res. Commun. 177, 688-695) share the same chymotrypsin-like fold with all S1 proteases. Due to substitutions in the active site residues these proteins do not posses any proteolytic function, yet they show high homology with active proteases. Differences between these proteins and specific proteases include regions that can serve as insertion sites for SDRs.

In a fourth approach, insertion sites for SDRs are identified experimentally by techniques such as alanine scanning, random mutagenesis, random insertion or random deletion. In contrast to the approach disclosed above, this approach does not require detailed knowledge about the three-dimensional structure of the scaffold protein. In one preferred variant of this approach, random mutagenesis of enzymes with relatively high specificity from the same structural class as the protein scaffold and screening for loss or change of specificity can be used to identify insertion sites for SDRs in the protein scaffold.

Random mutagenesis, alanine scanning, random insertion or random deletion are all done on the level of the polynucleotides encoding the enzymes. There are a variety of protocols known in the literature (e.g. Sambrook, J. F; Fritsch, E. F.; Maniatis, T.; Cold Spring Harbor Laboratory Press, Second Edition, 1989, New York). For example, random mutagenesis can be achieved by the use of a polymerase as described in patent WO 9218645. According to this patent, the one or more genes encoding the one or more proteases are amplified by use of a DNA polymerase with a high error rate or under conditions that increase the rate of misincorporations. For example the method of Cadwell and Joyce can be employed (Cadwell, R. C. and Joyce, G. F., PCR methods. Appl. 2 (1992) 28-33). Other methods of random mutagenesis such as, but not limited to, the use of mutator stains, chemical mutagens or UV-radiation can be employed as well.

Alternatively, oligonucleotides can be used for mutagenesis that substitute randomly distributed amino acid residues with an alanine. This method is generally referred to as alanine scanning mutagenesis (Fersht, A. R. Biochemistry (1989) 8031-8036). As a further alternative, modifications of the alanine scanning mutagenesis such as binominal mutagenesis (Gregoret, L. M. and Sauer, R. T. PNAS (1993) 4246-4250) or combinatorial alanine scanning (Weiss et al., PNAS (2000) 8950-8954) can be employed.

In order to express engineered enzymes, the DNA encoding such engineered proteins is ligated into a suitable expression vector by standard molecular cloning techniques (e.g. Sambrook, J. F; Fritsch, E. F.; Maniatis, T.; Cold Spring Harbor Laboratory Press, Second Edition, 1989, New York). The vector is introduced in a suitable expression host cell, which expresses the corresponding engineered enzyme variant. Particularly suitable expression hosts are bacterial expression hosts such as *Escherichia coli* or *Bacillus subtilis*, or yeast expression hosts such as *Saccharomyces cerevisae* or *Pichia pastoris*, or mammalian expression hosts such as Chinese Hamster Ovary (CHO) or Baby Hamster Kidney (BHK) cell lines, or viral expression systems such as bacteriophages like M13 or Lambda, or viruses such as the Baculovirus expression system. As a further alternative, systems for in vitro protein expression can be used. Typically, the DNA is ligated into an expression vector behind a suitable signal sequence that leads to secretion of the enzyme variants into the extracellular space, thereby allowing direct detection of protease activity in the cell supernatant. Particularly suitable signal sequences for *Escherichia coli* are HlyA, for *Bacillus subtilis* AprE, NprB, Mpr, AmyA, AmyE, Blac, SacB, and for *S. cerevisiae* Bar1, Suc2, Matα, Inu1A, Ggp1p. Alternatively, the enzyme variants are expressed intracellularly and the substrates are expressed also intracellularly. Preferably, this is done essentially as described in patent application WO 0212543, using a fusion peptide substrate comprising two auto-fluorescent proteins linked by the substrate amino-acid sequence.

As a further alternative, after intracellular expression of the enzyme variants, or secretion into the periplasmatic space using signal sequences such as DsbA, PhoA, PelB, OmpA, OmpT or gill for *Escherichia coli*, a permeabilisation or lysis step releases the enzyme variants into the supernatant. The destruction of the membrane barrier can be forced by the use of mechanical means such as ultrasonic, French press, or the use of membrane-digesting enzymes such as lysozyme. As another, further alternative, the genes encoding the enzyme variants are expressed cell-free by the use of a suitable cell-free expression system. For example, the S30 extract from *Escherichia coli* cells is used for this purpose as described by Lesly et al. (Methods in Molecular Biology 37 (1995) 265-278).

The ensemble of gene variants generated and expressed by any of the above methods are analyzed with respect to their affinity, substrate specificity or activity by appropriate assay and screening methods as described in detail for example in patent application PCT/EP03/04864. Genes from catalytically active variants having reduced specificity in comparison to the original enzyme are analyzed by sequencing. Sites at which mutations and/or insertions and/or deletions occurred are preferred insertion sites at which SDRs can be inserted site-specifically.

In a second embodiment, the one or more fully or partially random peptide sequences are inserted at random sites in the protein scaffold. This modification is usually done on the polynucleotide level, i.e. by inserting nucleotide sequences into the gene that encodes the protein scaffold. Several methods are available that enable the random insertion of nucleotide sequences. Systems that can be used for random insertion are for example ligation based systems (Murakami et al. Nature Biotechnology 20 (2002) 76-81), systems based on DNA polymerisation and transposon based systems (e.g. GPS-M™ mutagenesis system, NEB Biolabs; MGS™ mutation generation system, Finnzymes). The transposon-based methods employ a transposase-mediated insertion of a selectable marker gene that contains at its termini recognition sequences for the transposase as well as two sites for a rare cutting restriction endonuclease. Using the latter endonuclease one usually releases the selection marker and after religation obtains an insertion. Instead of performing the religation one can alternatively insert a fragment that has terminal recognition sequences for one or two outside cutting restriction endonuclease as well as a selectable marker. After ligation, one releases this fragment using the one or two outside cutting endonucleases. After creating blunt ends by standard methods one inserts blunt ended random fragments at random positions into the gene.

In a further preferred embodiment, methods for homologous in-vitro recombination are used to combine the mutations introduced by the above mentioned methods to generate enzyme populations. Examples of methods that can be applied are the Recombination Chain Reaction (RCR) according to patent application WO 0134835, the DNA-Shuffling method according to the patent application WO 9522625, the Staggered Extension method according to patent WO 9842728, or the Random Priming recombination according to patent application WO9842728. Furthermore, also methods for non-homologous recombination such as the Itchy method can be applied (Ostermeier, M. et al. Nature Biotechnology 17 (1999) 1205-1209).

Upon random insertion of a nucleotide sequence into the protein scaffold one obtains a library of different genes encoding enzyme variants. The polynucleotide library is subsequently transferred to an appropriate expression vector. Upon expression in a suitable host or by use of an in vitro expression system, a library of enzymes containing randomly inserted stretches of amino acids is obtained.

According to step (b) of this third aspect of the invention, one or more fully or partially random peptide sequences are inserted into the protein scaffold. The actual number of such inserted SDRs is determined by the intended quantitative specificity following the relation: the higher the intended specificity is, the more SDRs are inserted. Whereas a single SDR enables the generation of moderately specific enzymes, two SDRs enable already the generation of significantly specific enzymes. However, up to six and more SDRs can be inserted into a protein scaffold. A similar relation is valid for the length of the SDRs: the higher the intended specificity is, the longer are the SDRs that are to be inserted. SDRs can be as short as one to four amino acid residues. They can, however, also be as long as 50 amino acid residues. Significant specificity can already be generated by the use of SDRs of a length of four to six amino acid residues.

The peptide sequences that are inserted can be fully or partially random. In this context, fully random means that a set of sequences are inserted in parallel that includes sequences that differ from each other in each and every position. Partially random means that a set of sequences are inserted in parallel that includes sequences that differ from each other in at least one position. This difference can be either pair-wise or with respect to a single sequence. For example, when regarding an insertion of the length of four amino acids, partial random could be a set (i) that includes AGGG (SEQ ID NO: 100), GVGG (SEQ ID NO: 101), GGLG (SEQ ID NO: 102), GGGI (SEQ ID NO: 103), or (ii) that includes AGGG (SEQ ID NO: 104), VGGG (SEQ ID NO: 105), LGGG (SEQ ID NO: 106) and IGGG (SEQ ID NO: 107). Alternatively, random sequences also comprises sequences that differ from each other in length. Randomization of the peptide sequences is achieved by randomization of the nucleotide sequences that are inserted into the gene at the respective sites. Thereby, randomization can be achieved by employing mixtures of nucleobases as monomers during chemical synthesis of the oligonucleotides. A particularly preferred mixture of monomers for a fully random codon that in addition minimizes the probability of stop codons is NN(GTC). Alternatively, random oligonucleotides can be obtained by fragmentation of DNA into short fragments that are inserted into the gene at the respective sites. The source of the DNA to be fragmented may be a synthetic oligonucleotide but alternatively may originate from cloned genes, cDNAs, or genomic DNA. Preferably, the DNA is a gene encoding an enzyme. The fragmentation can, for example, be achieved by random endonucleolytic digestion of DNA. Preferably, an unspecific endonuclease such as DNAse I (e.g. from bovine pancreas) is employed for the endonucleolytic digestion.

If steps (a)-(c) of the inventive method are repeated cyclically, there are different alternatives for obtaining random peptide sequences that are inserted in consecutive rounds. Preferably, SDRs that were identified in one round as leading to increased specificity of enzyme are used as templates for the random peptide sequences that are inserted in the following round.

In a preferred alternative, the sequences selected in one round are analysed and randomized oligonucleotides are generated based on these sequences. This can, for example, be achieved by using in addition to the original nucleotide with a certain percentage mixtures of the other three nucleotides monomers at each position in the oligonucleotide synthesis. If, for example, in a first round an SDRs is identified that has the amino acid sequence ARLT (SEG ID NO: 108), e.g. encoded by the nucleotide sequence GCG CGC CTT ACC (SEO ID NO. 109), a random peptide sequence inserted in this SDR site could be encoded by an oligonucleotide with 70% G, 10% A, 10% T and 10% C at the first position, 70% C, 10% G, 10% T and 10% A at the second position, etc. This leads at each position approximately in 1 of 3 cases to the template amino acid and in 2 of 3 cases to another amino acid.

In another preferred alternative, the sequences selected in one round are analyzed and a consensus library is generated based on these sequences. This can, for example, be achieved by using defined mixtures of nucleotides at each position in the oligonucleotide synthesis in a way that leads to mixtures of the amino acid residues that were identified at each position of the SDR selected in the previous round. If, for example, in a first round two SDRs are identified that have the amino acid sequences ARLT (SEQ ID NO: 108) and VPGS (SEQ ID NO: 111), a consensus library inserted in this SDR site in the following round could be encoded by an oligonucleotide with the sequence G(C/T)G C(G/C)C (G/T)(G/T)G (A/T)CC (SEQ ID NO: 112). This would correspond to the random peptide sequence (A/V)(R/P)(L/G/V/W)(T/S) (SEQ ID NO: 113), thereby allowing all combinations of the amino acid residues identified in the first round, and, due to the degeneracy of the genetic code, allowing in addition to a lower degree alternative amino acid residues at some positions.

In another preferred alternative, the sequences selected in one round are, without previous analysis, recombined using methods for the in vitro recombination of polynucleotides, such as the methods described in WO 01/34835 (the following also provides details of the eighth and ninth aspect of the invention).

After insertion of the partially or fully random sequences into the gene encoding the scaffold protein, and eventually ligation of the resulting gene into a suitable expression vector using standard molecular cloning techniques (Sambrook, J. F; Fritsch, E. F.; Maniatis, T.; Cold Spring Harbor Laboratory Press, Second Edition, 1989, New York), the vector is introduced in a suitable expression host cell which expresses the corresponding enzyme variant. Particularly suitable expression hosts are bacterial expression hosts such as *Escherichia coli* or *Bacillus subtilis*, or yeast expression hosts such as *Saccharomyces cerevisae* or *Pichia pastoris*, or mammalian expression hosts such as Chinese Hamster Ovary (CHO) or Baby Hamster Kidney (BHK) cell lines, or viral expression systems such as bacteriophages like M13 T7 phage or Lambda, or viruses such as the Baculovirus expression system. As a further alternative, systems for in vitro protein expression can be used. Typically, the DNA is ligated into an expression vector behind a suitable signal sequence that leads to secretion of the enzyme variants into the extracellular space, thereby allowing direct detection of enzyme activity in the cell supernatant. Particularly suitable signal sequences for *Escherichia coli* are ompA, pelB, HlyA, for *Bacillus subtilis* AprE, NprB, Mpr, AmyA, AmyE, Blac, SacB, and for *S. cerevisiae* Bar1, Suc2, Matα, Inu1A, Ggp1p.

Alternatively, the enzyme variants are expressed intracellularly and the substrates are expressed also intracellularly. According to protease variants this is done essentially as described in patent application WO 0212543, using a fusion peptide substrate comprising two auto-fluorescent proteins linked by the substrate amino-acid sequence. As a further alternative, after intracellular expression of the enzyme variants, or secretion into the periplasmatic space using signal sequences such as DsbA, PhoA, PelB, OmpA, OmpT or gIII for *Escherichia coli*, a permeabilisation or lysis step releases the enzyme variants into the supernatant. The destruction of the membrane barrier can be forced by the use of mechanical means such as ultrasonic, French press, or the use of membrane-digesting enzymes such as lysozyme. As another, further alternative, the genes encoding the enzyme variants are expressed cell-free by the use of a suitable cell-free expression system. For example, the S30 extract from *Escherichia coli* cells is used for this purpose as described by Lesly et al. (Methods in Molecular Biology 37 (1995) 265-278).

After introduction of the vector into host cells, these cells are screened for the expression of enzymes with specificity for the intended target substrate. Such screening is typically done by separating the cells from each other, in order to enable the correlation of genotype and phenotype, and assaying the activity of each cell clone after a growth and expression period. Such separation can for example be done by distribution of the cells into the compartments of sample carriers, e.g. as described in WO 01/24933. Alternatively, the cells are separated by streaking on agar plates, by enclosing in a polymer such as agarose, by filling into capillaries, or by similar methods.

Identification of variants with the intended specificity can be done by different approaches. In the case of proteases, preferably assays using peptide substrates essentially as described in PCT/EP03/04864 are employed.

Regardless of the expression format, selection of enzyme variants is done under conditions that allow identification of enzymes that recognize and convert the target sequence preferably. As a first alternative, enzymes that recognize and convert the target sequence preferably are identified by screening for enzymes with a high affinity for the target substrate sequence. High affinity corresponds to a low $K_M$ which is selected by screening at target substrate concentrations substantially below the $K_M$ of the first enzyme. Preferably, the substrates that are used are linked to one or more fluorophores that enable the detection of the modification of the substrate at concentrations below 10 μM, preferably below 1 μM, more preferably below 100 nM, and most preferably below 10 nM.

As a second alternative, enzymes that recognize and convert the target substrate preferably are identified by employing two or more substrates in the assay and screening for activity on these two or more substrates in comparison. Preferably, the two or more substrates employed are linked to different marker molecules, thereby enabling the detection of the modification of the two or more substrates consecutively or in parallel. In the case of proteases, particularly preferably two peptide substrates are employed, one peptide substrate having an arbitrarily chosen or even partially or fully random amino-acid sequence thereby enabling to monitor the activity on an arbitrary substrate, and the other peptide substrate having an amino-acid sequence identical to or resembling the intended target substrate sequence thereby enabling to monitor the activity on the target substrate. Especially preferably, these two peptide substrates are linked to fluorescent marker molecules, and the fluorescent properties of the two peptide substrates are sufficiently different in order to distinguish both activities when measured consecutively or in parallel. For example, a fusion protein comprising a first autofluorescent protein, a peptide, and a second autofluorescent protein according to patent application WO 0212543 can be used for this purpose. Alternatively, fluorophores such as rhodamines are linked chemically to the peptide substrates.

As a third alternative, enzymes that recognize and convert the target substrate preferably are identified by employing one or more substrates resembling the target substrate together with competing substrates in high excess. Screening with respect to activity on the substrates resembling the target substrate is then done in the presence of the competing substrates. Enzymes having a specificity which corresponds qualitatively to the target specificity, but having only a low quantitative specificity are identified as negative samples in such a screen. Whereas enzymes having a specificity which corresponds qualitatively and quantitatively to the target specificity are identified positively. Preferably, the one or more substrates resembling the target substrate are linked to marker molecules, thereby enabling the detection of their modifications, whereas the competing substrates do not carry marker molecules. The competing substrates have arbitrarily chosen or random amino-acid sequences, thereby acting as competitive inhibitors for the hydrolysis of the marker-carrying substrates. For example, protein hydrolysates such as Trypton can serve as competing substrates for engineered proteolytic enzymes according to the invention.

As a fourth alternative, enzymes that recognize and convert the target substrate preferably are identified and selected by an amplification-coupled or growth-coupled selection step. Furthermore, the activity can be measured intracellularly and the selection can be done by a cell sorter, such as a fluorescence-activated cell sorter.

As a further alternative, enzymes that recognize and convert the target substrate ar e identified by first selecting enzymes that preferentially bind to the target substrate, and secondly selecting out of this subgroup of enzyme variants those enzymes that convert the target substrate. Selection for enzymes that preferentially bind the target substrate can be either done by selection of binders to the target substrate or by counter-selection of enzymes that bind to other substrates. Methods for the selection of binders or for the counter-selection of non-binders is known in the art. Such methods typically require phenotype-genotype coupling which can be solved by using surface display expression methods. Such methods include, for example, phage or viral display, cell surface display and in vitro display. Phage or viral display typically involves fusion of the protein of interest to a viral/phage protein. Cell surface display, i.e. either bacterial or eukaryotic cell display, typically involves fusion of the protein of interest to a peptide or protein that is located at the cell surface. In in-vitro display, the protein is typically made in vitro and linked directly or indirectly to the mRNA encoding the protein (DE 19646372).

The invention also provides for a composition or pharmaceutical composition comprising one or more engineered enzymes according to the first aspect of the invention as defined herein before. The composition may optionally comprise an acceptable carrier, excipient and/or auxiliary agent. Non-pharamceutical compositions as defined herein are research composition, nutritional composition, cleaning composition, desinfection composition, cosmetic composition or composition for personal care. Moreover, DNA sequences coding for the engineered enzyme as defined herein before and vectors containing said DNA sequences are also provided. Finally, transformed host cells (prokaryotic or eukaryotic) or transgenic organisms containing such DNA sequences and/or vectors, as well as a method utilizing such host cells or transgenic animals for producing the engineered enzyme of the first aspect of the invention are also contemplated.

DETAILED DESCRIPTION OF THE FIGURES

FIG. 1: Three-dimensional structure of human trypsin I with the active site residues shown in "ball-and-stick" representation and with the marked regions indicating potential SDR insertion sites.

FIG. 2: Alignment of the primary amino acid sequences of the human proteases trypsin I, alpha-thrombin and enteropeptidase all of which belong to the structural class S1 of the serine protease family. Trypsin represents an unspecific protease of this structural class, while alpha-thrombin and enteropeptidase are proteases with high substrate specificity. Compared to trypsin several regions of insertions of three or more amino acids into the primary sequence of a-thrombin and enterokinase are seen. The region marked with (-1-) and the region marked with (-3-) are preferred SDR insertion sites. In the tertiary structure of alpha-thrombin both regions are in the vicinity of the substrate binding site. These regions therefore fullfil two criteria to be selected as candidates for SDRs: firstly, they represent insertions in the specific proteases compared to the unspecific one and, secondly, they are close to the substrate binding site. A representation of the three-dimensional structure is given in FIG. 3.

FIG. 3: Three-dimensional structure of subtilisin with the active site residues being shown in "ball-and-stick" representation and with the numbered regions indicating potential SDR insertion sites.

FIG. 4: Alignment of the primary amino acid sequences of subtilisin E, furin, PC1 and PC5 all of which belong to the structural class S8 of the serine protease family. Subtilisin E represents an unspecific protease of this structural class, while furin, PC1 and PC5 are proteases with high substrate specificity. Compared to subtilisin several regions of insertions of three or more amino acids into the primary sequence of furin, PC1 and PC5 are seen. The regions marked with (-4-), (-5-), (-7-), (-9-) and (-11-) are preferred SDR insertion sites. These regions stretches fulfill two criteria to be selected as candidates for SDRs: firstly, they represent insertions in the specific proteases compared to the unspecific one and, secondly, they are close to the active site residues.

FIG. 5: Three-dimensional structure of beta-secretase with the active site residues being shown in "ball-and-stick" representation and with the numbered regions indicating potential SDR insertion sites.

FIG. 6: Alignment of the primary amino acid sequences of pepsin, b-secretase and cathepsin D, all of which belong to the structural class A1 of the aspartic protease family. Pepsin represents an unspecific protease of this structural class, while b-secretase and cathepsin D are proteases with high substrate specificity. Compared to pepsin several regions of insertions of three or more amino acids into the primary sequence of b-secretase and cathepsin D are seen. The regions marked with -1- to -11-correspond to possible SDR combining sites and are also marked in FIG. 5.

FIG. 7: illustrates the three-dimensional structure of caspase 7 with the active site residues being shown in "ball-and-stick" representation and with the numbered regions indicating potential SDR insertion sites.

FIG. 8: shows the primary amino acid sequence of caspase 7 as a member of the cysteine protease class C14 family (see also SEQ ID NO: 14).

FIG. 9: Schematic representation of method according to the third aspect of the invention.

Figure 10:
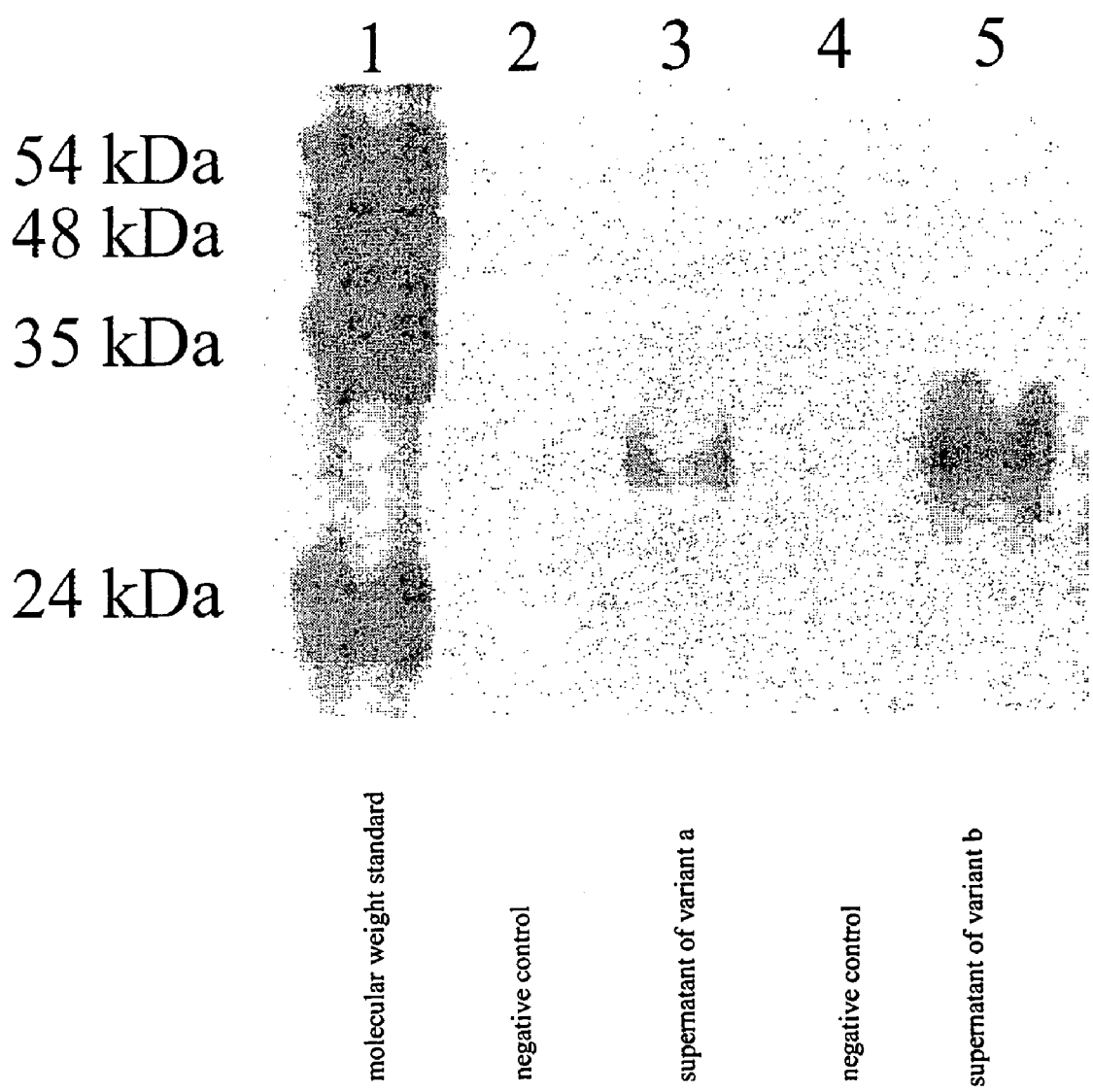
FIG. 10 shows a Western blot analysis of a culture supernatant of cells expressing variants of human trypsin I with SDR1 and SDR2, compared to negative controls.

FIG. 10: Western blot analysis of trypsin expression. Supernatant of cell cultures expressing variants of trypsin are compared to negative controls. Lane 1: molecular weight standard; lane 2: negative control; lane 3: supernatant of variant a; lane 4: negative control; lane 5: supernatant of variant b. A primary antibody specific to the expressed protein and a secondary antibody for generation of the signal were used.

Figure 11:
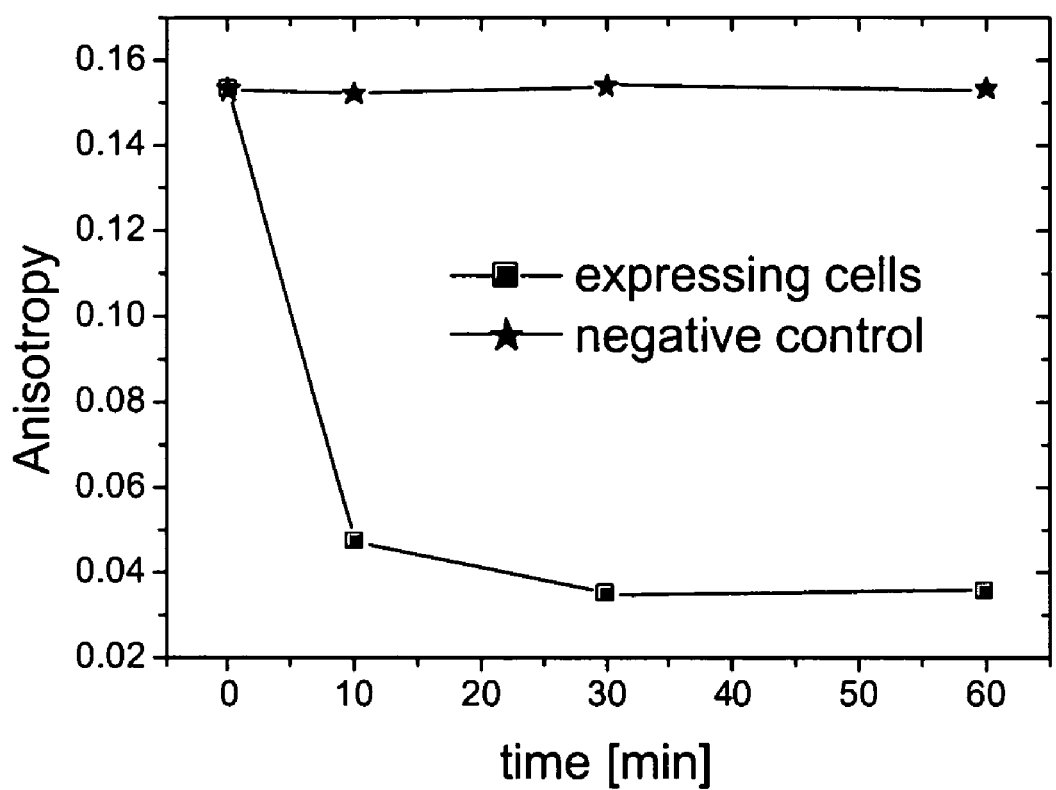
FIG. 11 shows the time course of the proteolytic cleavage of a target substrate by human trypsin I.

FIG. 11: Time course of the proteolytic cleavage of a target substrate. Supernatant of cells containing the vector with the gene for human trypsin and that of cells containing the vector without the gene was incubated with the peptide substrate described in the text. Cleavage of the peptide results in a decreased read out value. Proteolytic activity is confirmed for the positive clone.

Figure 12:
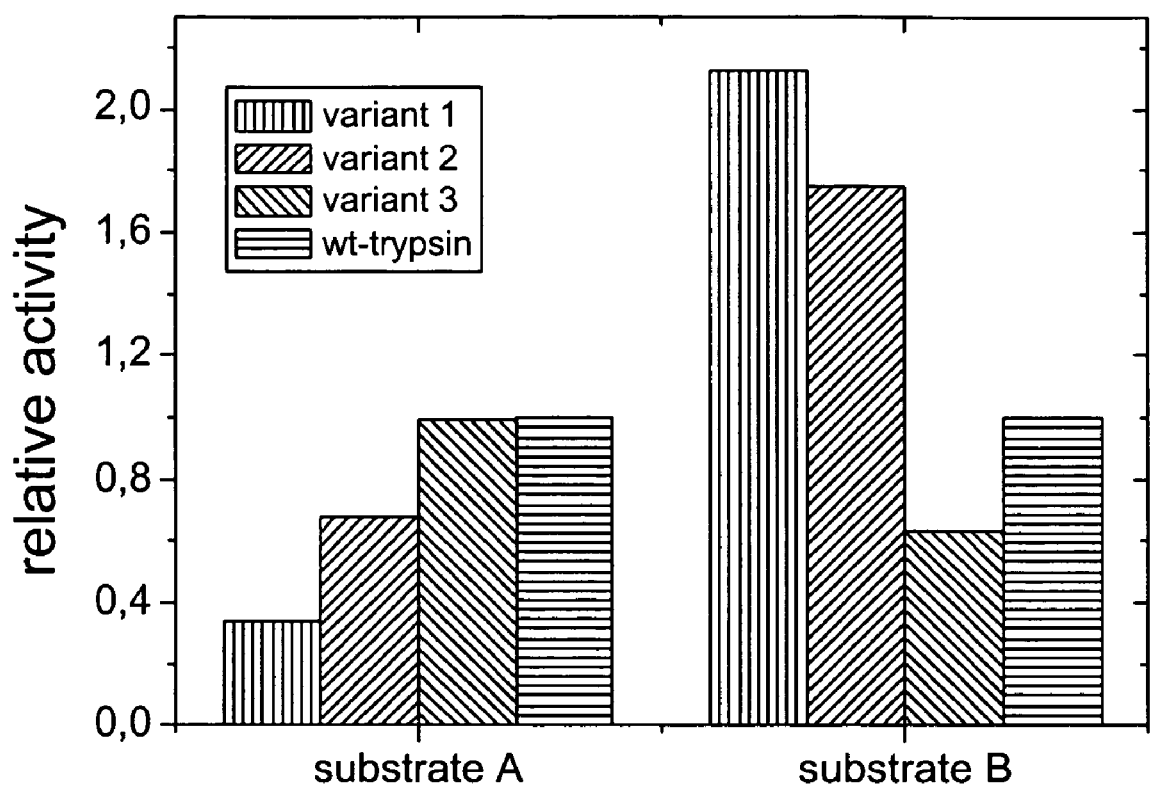
FIG. 12 shows the relative activities of three variants of inventive engineered proteolytic enzymes in comparison with human trypsin I on two different peptide substrates.

FIG. 12: Relative activity of three engineered proteolytic enzymes in comparison with human trypsin I on two different peptide substrates. A time course of the proteolytic digestion of the two substrates was performed and evaluated. Substrate B was used for screening and substrate A is a closely related sequence. Relative activity of the three variants was normalized to the activity of human trypsin I. Variant 1 and 2 clearly show increased specificity towards the target substrate. Variant 3, on the other hand, serves as a negative control with similar activities as the human trypsin I.

Figure 13:
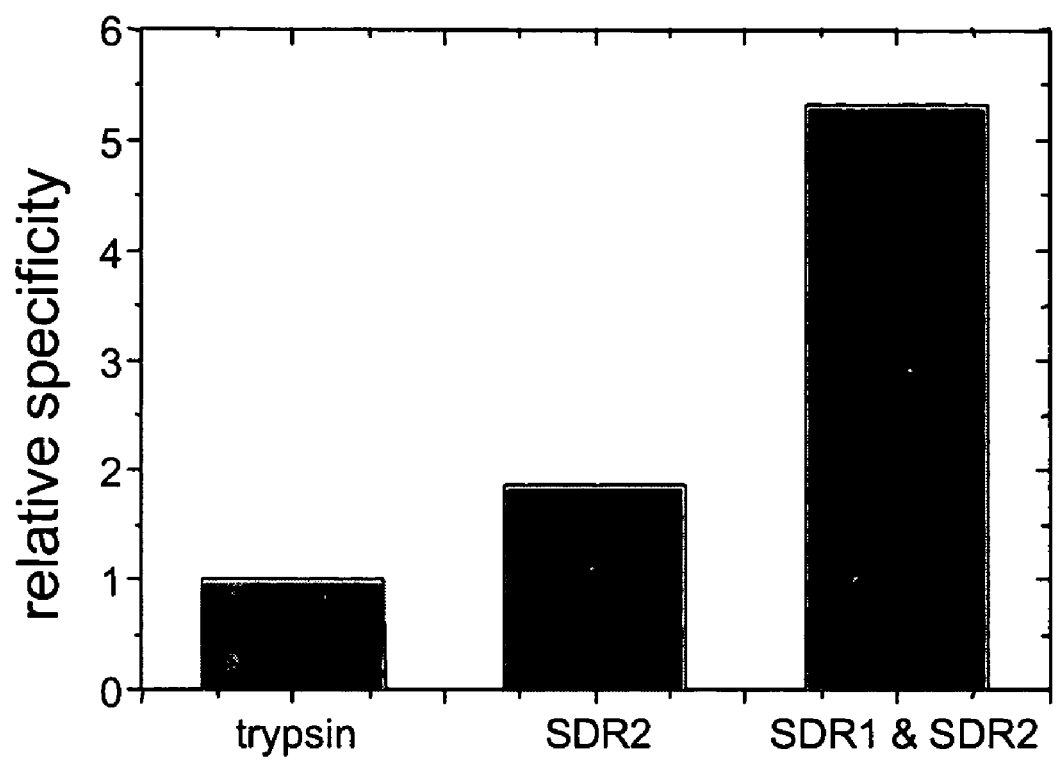
FIG. 13 shows the relative specificities of human trypsin I and variants of inventive engineered proteolytic enzymes with one or two SDRs, respectively. Activity of the proteases was determined in the presence and absence of competitor substrate i.e. peptone at a concentration of 10 mg/ml. Time courses for the proteolytic cleavage were recorded and the time constants k determined. The ratios between the time constants with and without competitor were formed and represent a quantitative measure for the specificity of the protease. The ratios were normalized to trypsin. The specificity of the variant containing two SDRs is 2.5 fold higher than that of the variant with SDR2 alone.

FIG. 13: Relative specificities of trypsin and variants of engineered proteolytic enzymes with one or two SDRs, respectively. Activity of the proteases was determined in the presence and absence of competitor substrate, i.e. peptone at a concentration of 10 mg/ml. Time courses for the proteolytic cleavage were recorded and the time constants k determined. The ratios between the time constants with and without competitor were formed and represent a quantitative measure for the specificity of the protease. The ratios were normalized to trypsin. The specificity of the variant containing two SDRs is 2.5 fold higher than that of the variant with SDR2 alone.

FIG. 14: Shows the relative specificities of protease variants in absence and presence of competitor substrate. The protease variants containig two inserts with different sequences and the non-modified scaffold human trypsin I were expressed in a suitable host. Activity of the protease variants was determined as the cleavage rate of a peptide with the desired target sequence of TNF-alpha in the absence and presence of competitor substrate. Specificity is expressed as the ratio of cleavage rates in the presence and absence of competitor.

FIG. 15: The figure shows the reduction of cytotoxicity induced by human TNF-alpha when incubating the human TNF-alpha with concentrated supernatant from cultures expressing the inventive engineered proteolytic enzymes being specific for human TNF-alpha. This indicates the efficacy of the inventive engineered proteolytic enzymes.

FIG. 16: The figure shows the reduction of cytotoxicity induced by human TNF-alpha when incubating the human TNF-alpha with different concentrations of purified inventive engineered proteolytic enzyme being specific for human TNF-alpha. Variant g comprises Seq ID No:72 as SDR1 and Seq ID No:73 as SDR2. This indicates the efficacy of the inventive engineered proteolytic enzymes.

FIG. 17: The figure compares the activity of inventive engineered proteolytic enzymes being specific for human TNF-alpha with the activity of human trypsin I on two protein substrates: (a) human TNF-alpha; (b) mixture of human serum proteins. This indicates the safety of the inventive engineered proteolytic enzymes. Variant x corresponds to Seq ID No: 75 comprising the SDRs according to Seq ID No. 89 (SDR1) and 95 (SDR2). Variants xi and xii correspond to derivatives thereof comprising the same SDR sequences.

FIG. 18: Specific hydrolysis of human VEGF by an engineered proteolytic enzyme derived from human trypsin.

EXAMPLES

In the following examples, materials and methods of the present invention are provided including the determination of catalytic properties of enzymes obtained by the method. It should be understood that these examples are for illustrative purpose only and are not to be construed as limiting this invention in any manner. All publications, patents, and patent applications cited herein are hereby incorporated by reference in their entirety for all purposes.

In the experimental examples described below, standard techniques of recombinant DNA technology were used that were described in various publications, e.g. Sambrook et al. (1989), Molecular Cloning: A Laboratory Manual, Cold Spring Harbor Laboratory, or Ausubel et al. (1987), Current Protocols in Molecular Biology 1987-1988, Wiley Interscience. Unless otherwise indicated, restriction enzymes, polymerases and other enzymes as well as DNA purification kits were used according to the manufacturers specifications.

Example I

Identification of SDR Sites in Human Trypsin

Insertion sites for SDRs have been identified in the serine protease human trypsin I (structural class S1) by comparison with members of the same structural class having a higher sequence specificity. Trypsin represents a member with low substrate specificity, as it requires only an arginine or lysine residue at the $P_1$ position. On the other hand, thrombin, tissue-type plasminogen activator or enterokinase all have a high specificity towards their substrate sequences, i.e. (L/I/V/F)XPR^NA (SEQ ID NO: 97), CPGR^VVGG (SEQ ID NO: 98) and DDDK^(SEQ ID NO: 99), respectively. The primary sequences and tertiary structures of these and further S1 serine proteases have been aligned in order to determine regions of low and high sequence and structure homology and especially regions that correspond to insertions in the sequences of the more specific proteases (FIG. 2). Several regions of insertions equal or longer than 3 amino acids representing potential SDR sites have been identified as indicated in FIG. 1. These regions were chosen as target sites for the insertion of SDRs in the examples below, e.g. SDR1 (region one in FIG. 2, after amino acid 42 according to SEQ ID NO:1) with a length of six and SDR2 (region three in FIG. 2, after amino acid 123 according to SEQ ID NO:1) with a length of five amino acids, respectively.

Example II

Molecular Cloning of the Human Trypsin I Gene to be Used as Scaffold Protein and Expression of the Mature Protease in *B. subtilis*

The gene encoding the unspecific protease human trypsinogen I was cloned into the vector pUC18. Cloning was done as follows: the coding sequence of the protein was amplified by PCR using primers that introduced a KpnI site at the 5' end and a BamHI site at the 3' end. This PCR fragment was cloned into the appropriate sites of the vector pUC18. Identity was confirmed by sequencing. After sequencing the coding sequence of the mature protein was amplified by PCR using primers that introduced different BglI sites at the 5' end and the 3' end.

This PCR fragment was cloned into the appropriate sites of an *E. coli-B. subtilis* shuttle vector. The vector contains a pMB1 origin for amplification in *E. coli*, a neomycin resistance marker for selection in *E. coli*, as well as a P43 promoter for the constitutive expression in *B. subtilis*. A 87 bp fragment that contains the leader sequence encoding the signal peptide from the sacB gene of *B. subtilis* was introduced behind the P43 promoter. Different BglI restriction sites serve as insertion sites for heterologous genes to be expressed.

Expression of human trypsin I was confirmed by measurement of the proteolytic aciticity in supernatant of cells containing the vector with the gene in comparison to a negative control. A peptide including an arginine cleavage site was chosen as a substrate. The peptide was N-terminally biotinylated and labeled with a fluorophore at the C-terminus. After incubation of the peptide with culture supernatant streptavidin was added. Uncleaved peptide associate with streptavidin and lead to a high read out value while cleavage results in low read out values. FIG. 11 shows the time course of a proteolytic digestion of *B. subtilis* cells containing the vector with the trypsin I gene in comparison to *B. subtilis* cells containing the vector without the trypsin I gene (negative control).

As a further confirmation of expression of the protease, supernatants of cells containing the vector with the gene and control cells were analyzed by polyacrylamid gel electrophoreses and subsequent western blot using an antibody specific to the target protease. The procedure was performed according to standard methods (Sambrook, J. F; Fritsch, E. F.; Maniatis, T.; Cold Spring Harbor Laboratory Press, Second Edition, 1989, New York). FIG. 8 confirms expression of the protein only in the cells harbouring the vector with the gene for trypsin.

Example III

Providing a Scaffold Protein

In this example, human trypsin I was used as the scaffold protein. The gene was either used in its natural form, or, alternatively, was modified to result in a scaffold protein with increased catalytic activity or further improved characteristics. The modification was done by random modification of the gene, followed by expression of the enzyme and subsequent selection for increased activity. First, the gene was PCR amplified under error-prone conditions, essentially as described by Cadwell, R. C and Joyce, G. F. (PCR Methods Appl. 2 (1992) 28-33). Error-prone PCR was done using 30 pmol of each primer, 20 mmol dGTP and dATP, 100 nmol dCTP and dTTP, 20 fmol template, and 5 U Taq DNA polymerase in 10 mM Tris HCl pH 7.6, 50 mM KCl, 7 mM MgCl2, 0.5 mM MnCl2, 0.01% gelatin for 20 cycles of 1 min at 94° C., 1 min at 65° C. and 1 min at 72° C. The resulting DNA library was purified using the Qiaquick PCR Purification Kit following the suppliers' instructions. The PCR product was digested with the restriction enzyme BglI and purified. Afterwards, the PCR product was ligated into the *E. coli-B. subtilis* shuttle vector described above which was digested with BglI and dephosphorylated. The ligation products were transformed into *E. coli*, amplified in LB, and the plasmids were purified using the Qiagen Plasmid Purification Kit following the suppliers' instructions. Resulting plasmids were transformed into *B. subtilis* cells.

Alternatively, or in addition to random mutagenesis, variants of the gene were statistically recombined at homologous positions by use of the Recombination Chain Reaction, essentially as described in WO 0134835. PCR products of the genes encoding the protease variants were purified using the QIAquick PCR Purification Kit following the suppliers' instructions, checked for correct size by agarose gel electrophoresis and mixed together in equimolar amounts. 80 µg of this PCR mix in 150 mM Tris HCl pH 7.6, 6.6 mM MgCl$_2$ were heated for 5 min at 94° C. and subsequently cooled down to 37° C. at 0.05° C./s in order to re-anneal strands and thereby produce heteroduplices in a stochastic manner. Then, 2.5 U Exonuclease III per µg DNA were added and incubated for 20, 40 or 60 min at 37° C. in order to digest different lengths from both 3' ends of the heteroduplices. The partly digested PCR products were refilled with 0.6 U Pfu polymerase per µg DNA by incubating for 15 min at 72° C. in 0.17 mM dNTPs and Pfu polymerase buffer according to the suppliers' instructions. After performing a single PCR cycle, the resulting DNA was purified using the QIAquick PCR Purification Kit following the suppliers' instructions, digested with BglI and ligated into the linearized vector. The ligation products were transformed into *E. coli*, amplified in LB containing ampicillin as marker, and the plasmids were purified using the Qiagen Plasmid Purification Kit following the suppliers' instructions. Resulting plasmids were transformed into *B. subtilis* cells.

Example IV

Insertion of SDRs into the Protein Scaffold of Human Trypsin I and Generation of an Engineered Proteolytic Enzyme with Specificity for a Peptide Substrate Having the Sequence KKWLGRVPGGPV In order to create insertion sites for SDRs in human trypsin I, two pairs of different restriction sites were introduced into the gene at sites that were identified as potential SDR sites (see Example I above) without changing the amino acid sequence. The insertion of the restriction sites was done by overlap extension PCR. Primers restr1 and restr2 were used for the introduction of SacII and BamHI restriction sites, restr3 and restr4 were used for the introduction of KpnI and NheI restriction sites. The sequences of the primers were as follows:

```
Binding site for restr1 and restr2 and the corresponding
amino acid sequence:
5'-GGTGGTATCAGCAGGCCACTGCTACAAGTCCCGCATCCAGGT-3'          (SEQ ID NO:54)
   V V S A G H C Y K S R I Q Forward primer restr1:
5'-GGTGGTATCCGCGGGCCACTGCTACAAGTCCCGGATCCAGGT-3'          (SEQ ID NO:56)

Reverse primer restr2:
5'-ACCTGGATCCGGGACTTGTAGCAGTGGCCCGCGGATACCACC-3'          (SEQ ID NO:57)

Binding site for restr3 and restr4 and the corresponding
amino acid sequence:
5'-CCACTGGCACGAAGTGCCTCATCTCTGGCTGGGGCAACACTGCGAGCTCT-3'  (SEQ ID NO:58)
   T G T K C L I S G W G N T A S S
```

```
Forward primer restr3:
5'-CCACTGGCACGAAGTGCCTCATCTCTGGCTGGGGCAACACTGCGAGCTCT-3'   (SEQ ID NO:60)

Reverse primer restr4:
5'-AGAGCTAGCAGTGTTGCCCCAGCCAGAGATGAGGCACTTGGTACCAGTGG-3'   (SEQ ID NO:61)
```

In a first overlap extension PCR, the SacII/BamHI sites were introduced, enabling to insert SDR1, and in a second overlap extension PCR the KpnI/NheI sites, enabling the insertion of SDR2. The product of the overlap extension PCR was amplified using primers pUC-forward and pUC-reverse. The sequences of pUC-forward and pUC-reverse are as follows:

```
pUC-forward:
5'-GGGGTACCCCACCACCATGAATCCACTCCT-3'  (SEQ ID NO:62)

pUC-reverse:
5'-CGGGATCCGGTATAGAGACTGAAGAGATAC-3'  (SEQ ID NO:63)
```

The restriction sites generated thereby were subsequently used to insert defined or random oligonucleotides into the SDR1 and SDR2 insertion sites by standard restriction and ligation methods. Typically, two complementary synthetic 5'-phosphorylated oligonucleotides were annealed and ligated into a vector carrying the modified human trypsin I gene that was cleaved with the respective restriction enzymes. Oligonucleotides encoding SDR1 were inserted via the SacII/BamHI sites whereas oligonucleotides encoding SDR2 were inserted via the KpnI/NheI sites. For each insertion an oligonucleotide pair according to the following general sequences was used ([P] indicating 5'-phosphorylation, N and X indicating any nucleotide or amino acid residue, respectively):

The codon NNB, or VNN in the reverse strand, allows all 20 amino acids to made, but reduces the probability of encoding a stop codon from 0.047 to 0.021.

As a further alternative, after identification of SDRs that lead to increased specificity, these SDRs were used as templates for further randomization. Thereby, random peptide sequences were inserted that were partially randomized at each position and partially identical at each position to the original sequence.

As an example, random peptide sequences that have in approximately 1 of 3 cases the template amino acid residue and in approximately 2 of 3 cases any other amino acid residue at each position were inserted into the two SDR insertion sites of the modified human trypsin I. For this purpose, primers that contain at each nucleotide position of the SDR approximately 70% of the template bases and 30% of a mixture of the three other bases were used.

With each primer pair a PCR was performed under standard conditions using the human trypsin I gene as template. The resulting DNA was purified using the QIAquick PCR Purification Kit following the suppliers' instructions and digested with SacII and NheI. After digestion the DNA was purified and ligated into the SacII and NheI digested and dephosphorylayted vector. The ligation products were transformed into E. coli, amplified in LB

```
oligox-SDR1f:
5'-[P]-GGGCCACTGCTACNNNNNNNNNNNNNNNNNNNAAGTCCCG-3'         (SEQ ID NO:64)

oligox-SDR1r:
3'-CGCCCGGTGACGATGNNNNNNNNNNNNNNNNNNNNTTCAGGGCCTAG-[P]-5' (SEQ ID NO:66)
     G H C Y X X X X X X X K S oligox-SDR2f:
5'-[P]-CAAGTGCCTCATCTCTGGCTGGGGCAACNNNNNNNNNNNNNNNNACTG-3' (SEQ ID NO:67)

oligox-SDR2r:
3'-CATGGTTCACGGAGTAGAGACCGACCCCGTTGNNNNNNNNNNNNNNNNTGACGATC-[P]-5'  (SEQ ID NO:69)
     K C L I S G W G N X X X X X T
```

As an alternative to the above method, a PCR based method was used for the integration of random-sequences into the SDR1 and SDR2 insertion sites in the modified human trypsin I. For each SDR, one primer was used where the SDR region is fully randomized. Sequences of the primers were as follows (N=A/C/G/T, B=C/G/T, V=A/C/G):

containing the respective marker, and the plasmids were purified using the Qiagen Plasmid Purification Kit following the suppliers' instructions. Resulting plasmids were transformed into B. subtilis cells. These cells were then separated to single cells, grown to clones, and after expression of the protease gene screened for proteolytic activity.

```
Primer SDR1-mutnnb-forward:
5'-TGGTATCCGCGGGCCACTGCTACNNBNNBNNBNNBNNBNNBAAGTCCCGGATCCAGGTG-3'  (SEQ ID NO:70)

Primer SDR2-mutnnb-reverse:
5'-GGCGCCAGAGCTAGCAGTVNNVNNVNNVNNVNNGTTGCCCCAGCCAGAGATG-3'  (SEQ ID NO:71)
```

The following substrates were employed for screening for proteolytic activity (SEQ ID.NOs:76 and 77):

| substrate A | L | L | W | L | G | R | V | V | G | P | V |
| substrate B | K | K | W | L | G | R | V | P | G | P | V |

Protease variants were screened on substrate B at complexities of $10^6$ variants by confocal fluorescence spectroscopy. The substrate was a peptide biotinylated at the N-terminus and fluorescently labeled at the C-terminus. After incubation of the peptide with supernatant of cells expressing different variants of the protease, streptavidin is added and the samples are analysed by confocal fluorimetry. The low concentration of the peptide (20 nM) leads to a preferential cleavage by proteases with a high $k_{cat}/K_M$ value, i.e. proteases with high specificity towards the target sequence.

Variants selected in the screening procedure were further evaluated for their specificity towards substrate B and closely related substrate A by measuring time courses of the proteolytic digestion and determining the rate constants which are proportional to the $k_{cat}/K_M$ values. Clearly, compared to the human trypsin that was used as scaffold protein, the specific activity of variants 1 and 2 is shifted (SEQ ID NOs: 2 and 3, respectively) towards substrate B. Variant 3 (SEQ ID NO:4), on the other hand, serves as a negative control with similar activities as the human trypsin I. Sequencing of the genes of the three variants revealed the following amino acid sequences in the SDRs.

TABLE 2

Sequences of the two SDRs in three different variants selected for specific hydrolysis of substrate B (SEQ ID NOs: 78-83).

|  | SDR 1 |  |  |  |  | SDR 2 |  |  |  |  |
| --- | --- | --- | --- | --- | --- | --- | --- | --- | --- | --- |
| Trypsin | — | — | — | — | — | — | — | — | — | — |
| Variant 1 | D | A | V | G | R | D | T | I | T | N | S |
| Variant 2 | N | G | R | D | L | E | V | R | G | T | W |
| Variant 3 | G | F | V | M | F | N | R | S | P | L | T |

In a further experiment a pool of variants containing different numbers of SDRs per gene were screened for increased specificity using a mixture of the defined substrate and pepton as a competing substrate. Variants containing one or two SDRs per gene have been analyzed further. As a measure for the specificity the activity in the peptide cleavage assay was compared with and without the presence of the competing substrate. The concentration of the competing substrate was 10 mg/ml. Under these conditions, unspecific proteases show, compared to specific proteases, a stronger decrease in activity with increasing competitor concentrations (range between 0 and 100 mg/ml). The ratio of proteolytic activity with and without substrate is a quantitative measure for the specificity of the proteases. FIG. 9 shows the relative activities with and without competing substrate. Human trypsin I that was used as the scaffold protein and two variants, one containing only SDR2, and one containing both SDRs, were compared. The specificity of the variant with both SDRs is by a factor of 2.5 higher than that of the variant with SDR2 only, confirming that there is a direct relation between the number of SDRs and the quantitative specificity of resulting engineered proteolytic enzymes.

Example V

Figure 14:
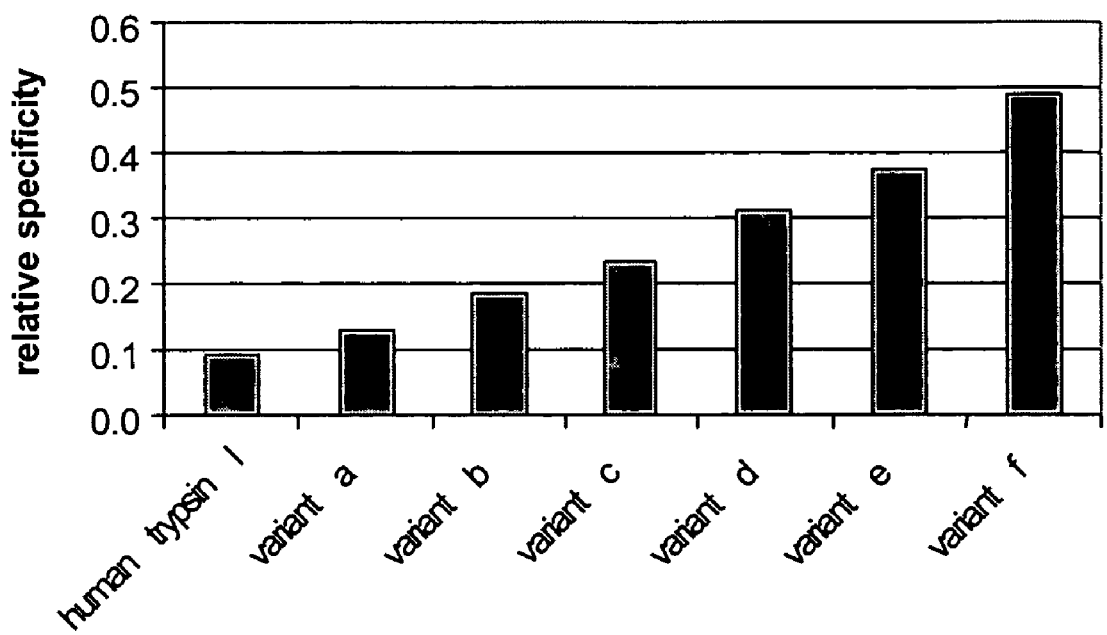
FIG. 14: shows the relative specificities of human trypsin I and of variants of inventive engineered proteolytic enzymes being specific for human TNF-alpha with this scaffold on peptides with a target sequence of human TNF-alpha. The protease variants containing two inserts with different sequences and the non-modified scaffold human trypsin I were expressed in a suitable host. Activity of the protease variants was determined as the cleavage rate of a peptide with the desired target seciuence of TNF-alpha in the absence and presence of competitor substrate. Specificity is expressed as the ratio of cleavage rates in the presence and absence of competitor.

Generation of an Engineered Proteolytic Enzyme that Specifically Inactivates Human TNF-Alpha Human trypsin alpha I or a derivative comprising one or more of the following amino acid substitutions E56G; R78W; Y131F; A146T; C183R was used as protein scaffold for the generation of an engineered proteolytic enzyme with high specificity towards human TNF-alpha. The identification of SDR sites in human trypsin I or derivatives thereof was done as described above. Two insertion sites within the scaffold were choosen for SDRs. The protease variants containing two inserts with different sequences and also the human trypsin I itself with no inserts were expressed in a *Bacillus subtilis* cells. The variant protease cells were separated to single cell clones and the protease expressing variants were screened for proteolytic activity on peptides with the desired target sequence of TNF-alpha. The activity of the protease variants was determined as the cleavage rate of a peptide with the desired target sequence of TNF-alpha in the absence and presence of competitor substrate. The specificity is expressed as the ratio of cleavage rates in the presence and absence of competitor (FIG. 14).

TABLE 3

Relative specificity of variants of engineered proteolytic enzymes with different SDR sequences in absence and presence of competitor substrate (SEQ ID NOs: 84-95).

|  | k with comp./ k without comp. | Seq. of SDR 1 | Seq. of SDR 2 |
| --- | --- | --- | --- |
| scaffold (no SDRs) | 0.092 | — | — |
| variant a | 0.130 | RPWDPS | VHPTS |
| variant b | 0.187 | GFVMFN | RSPLT |
| variant c | 0.235 | EIANRE | RGART |
| variant d | 0.310 | KAVVGT | RTPIS |
| variant e | 0.374 | VNIMAA | TTARK |
| variant f | 0.487 | AAFNGD | RKDFW |

Figure 15:
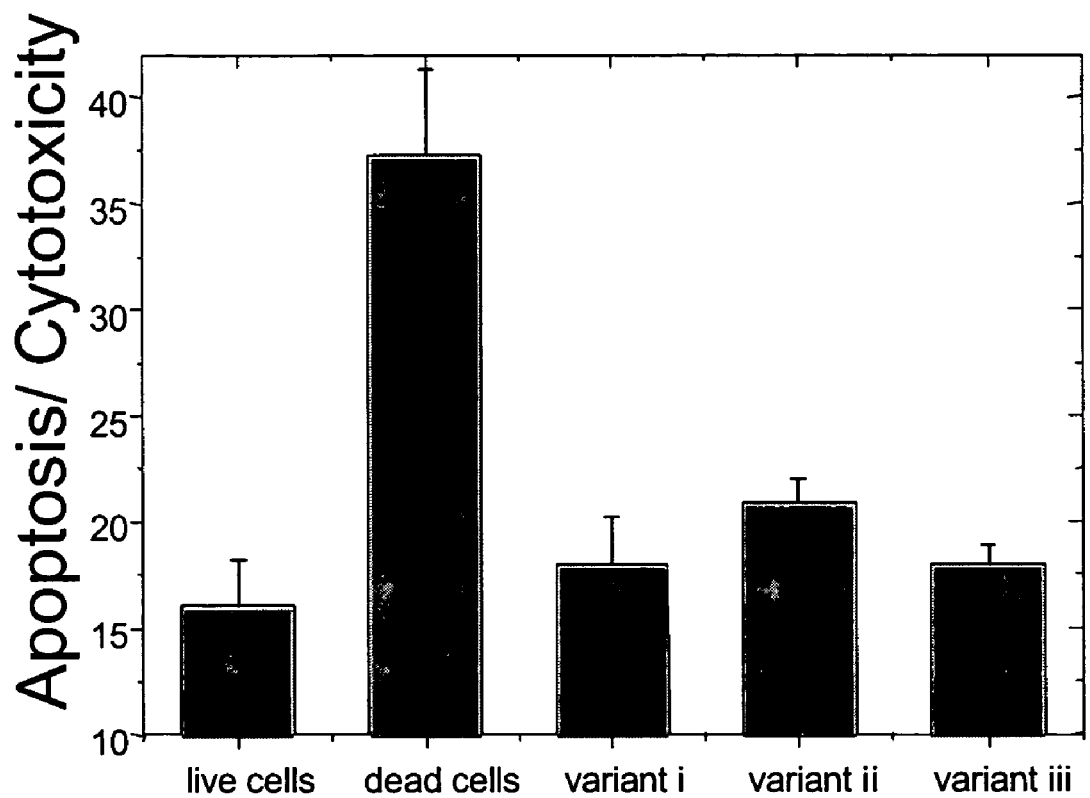
FIG. 15: shows the reduction of cytotoxicity induced by TNF-alpha when incubating the TNF-alpha with concentrated supernatant from cultures expressing the inventive engineered proteolytic enzymes being specific for human TNF-alpha.
Figure 16:
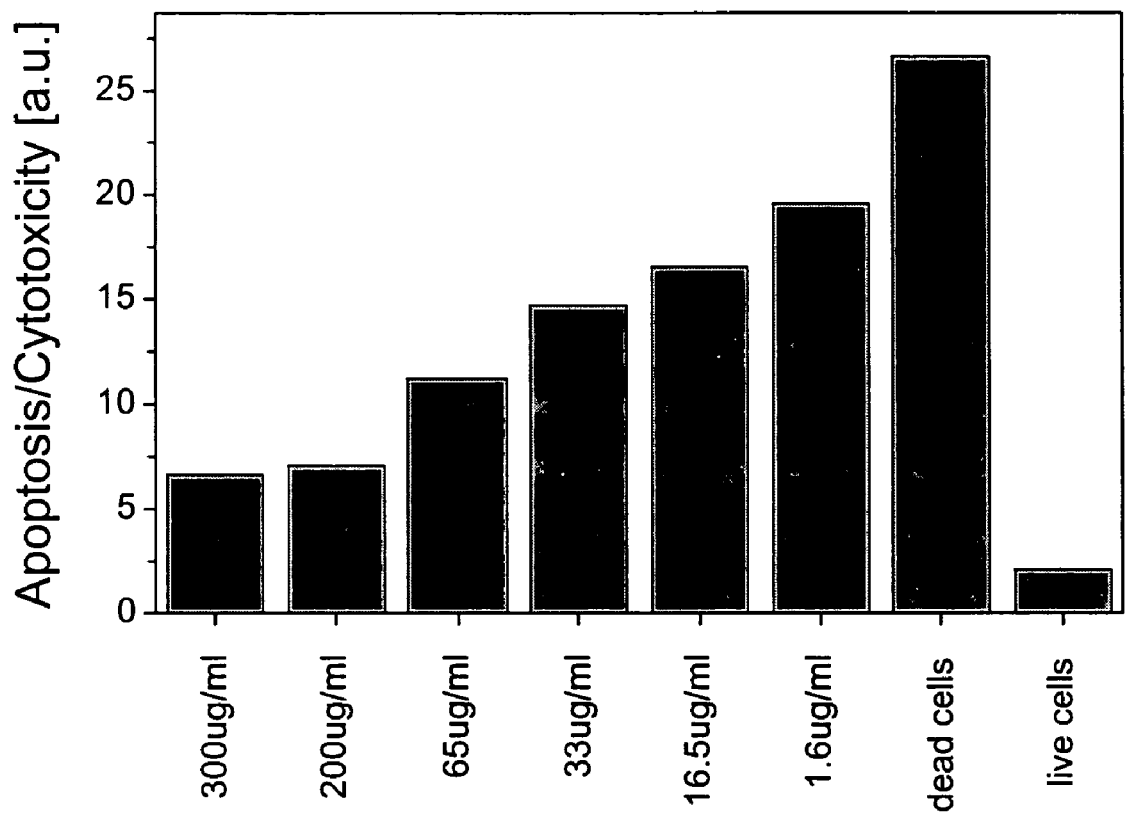
FIG. 16: shows the reduction of cytotoxicity induced by TNF-alpha when incubating the TNF-alpha with purified inventive engineered proteolytic enzyme being specific for human TNF-alpha.

The antagonistic effect of three inventive protease variants on human TNF-alpha is shown in FIG. 15. By the use of the variants, the induction of apoptosis is almost completely eliminated indicating the anti-inflammatory efficacy of the inventive proteases to initiate TNF-alpha break down. TNF-alpha has been incubated with concentrated supernatant from cultures expressing the variants i to iii for 2 hours. The resulting TNF-alpha has been incubated with non-modified cells for 4 hours. The effect of the remaining TNF-alpha activity was determined as the extent of apoptosis induction by detection of activated caspase-3 as marker for apoptotic cells. For the controls either no protease was added with the human TNF-alpha (dead cells) or buffer instead of human TNF-alpha (live cells) was used, respectively. An analogous experiment is shown in FIG. 16 using purified variant xiii. TNF-alpha was incubated with different concentrations of the purified inventive protease variant.

Figure 17A:
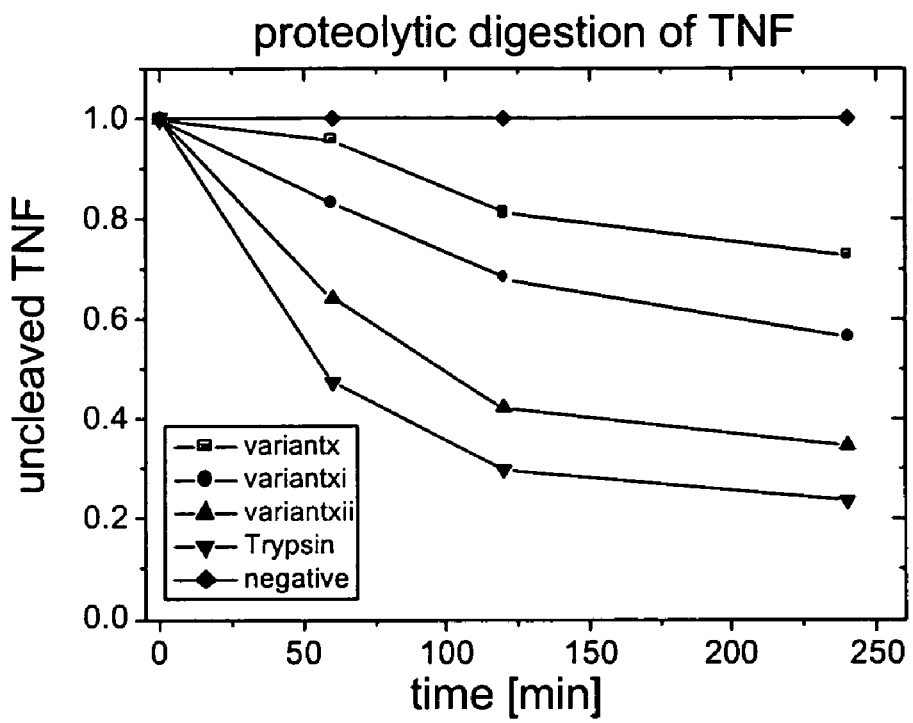
FIG. 17: compares the activity of inventive engineered proteolytic enzymes being specific for human TNF-alpha with the activity of human trypsin I on two protein substrates: (a) human TNF-alpha; (b) mixture of human serum proteins.
Figure 17B:
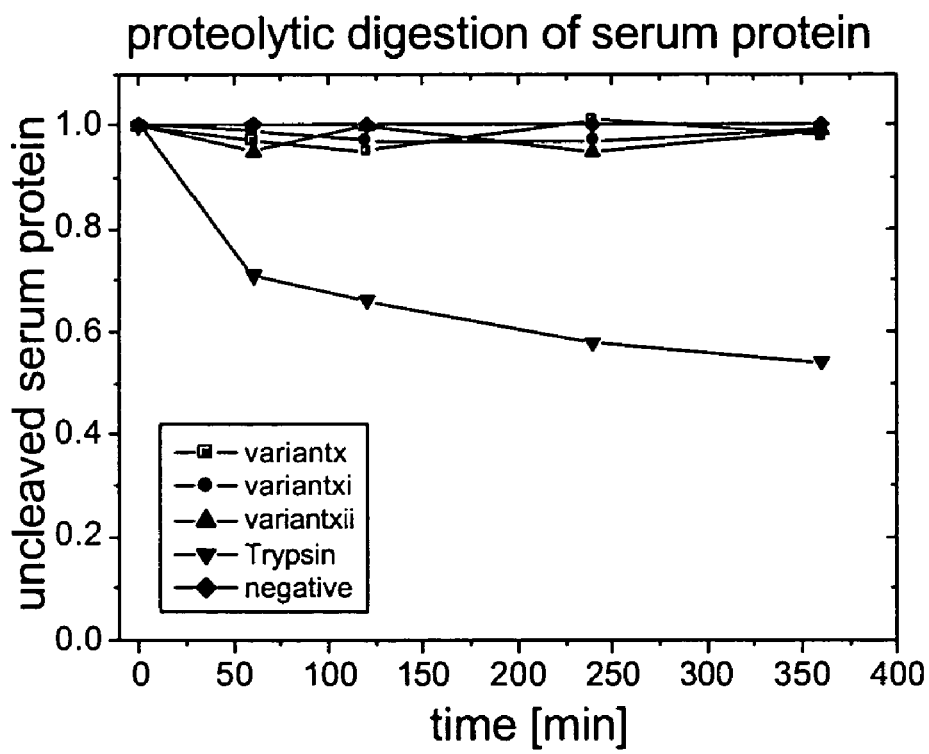
Figure 18:
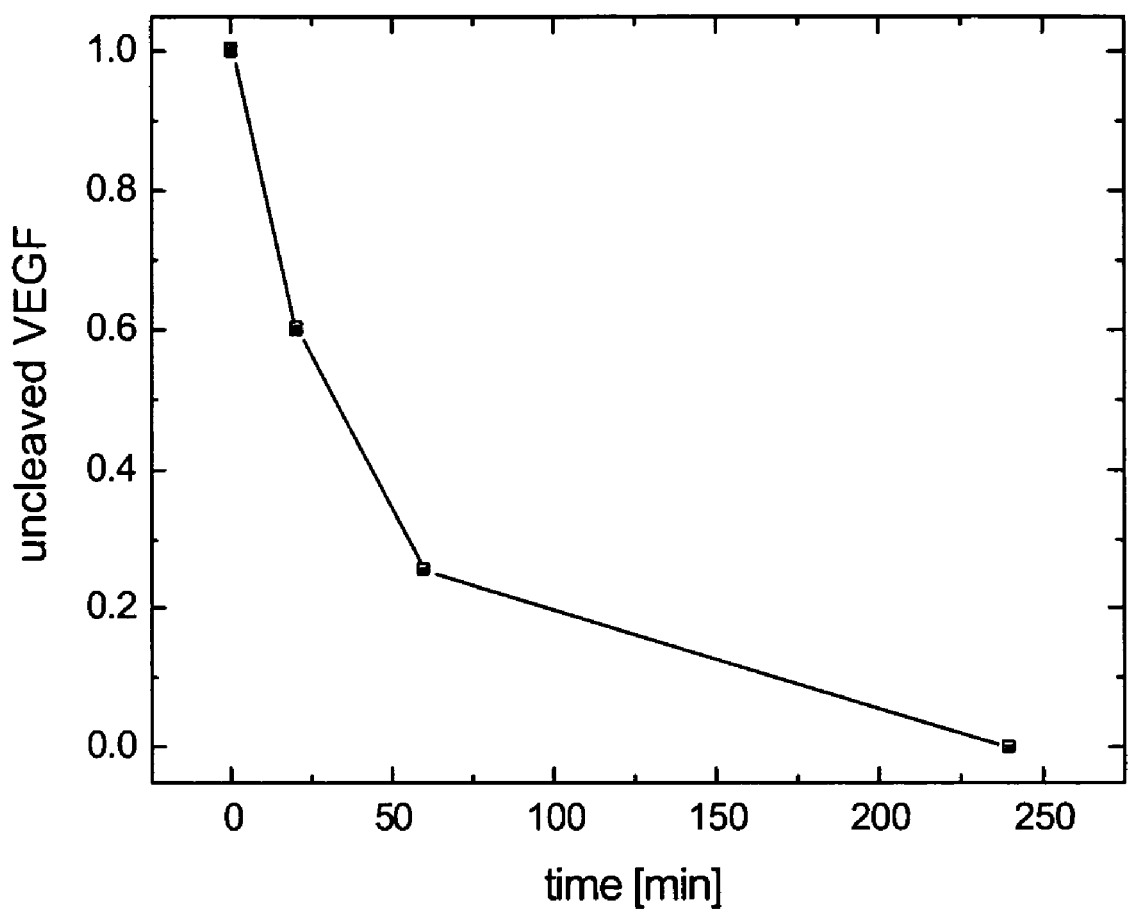
FIG. 18: showes the specific activity of an inventive engineered proteolytic enzyme with specificity for human VEGF.

To demonstrate the specificity of the inventive protease variants, proteins from human blood serum or purified human TNF-alpha have been incubated with human trypsin I or the inventive engineered proteolytic enzyme variants, respectively. Here, variant x corresponds to Seq ID No: 75 comprising the same SDRs as variant f, i.e. SDRs according to Seq ID No. 89 (SDR1) and 95 (SDR2). Variants xi and xii correspond to derivatives thereof comprising the same SDR sequences. Remaining intact protein was was determined as a function of time. While the variants as well as human trypsin I digest human TNF-alpha, only trypsin shows activity on serum protein (FIGS. 17a and b). This demonstrates the high TNF-alpha specificity of the inventive pro-

49 teolytic enzymes and indicates their safety and accordingly their low side effects for therapeutic use.

Example VI

Generation of an Engineered Proteolytic Enzyme that Specifically Hydrolysis Human VEGF Human trypsin I was used as protein scaffold for the generation of an engineered proteolytic enzyme with high specificity towards human VEGF. The identification of SDR sites in human trypsin I was done as described above. Two insertion sites within the scaffold were choosen for SDRs. The protease variants containing two inserts with different sequences were expressed in *Bacillus subtilis* cells. The variant protease cells were separated to single cell clones and the protease expressing variants were screened as described above. The activity of the protease variants was determined as the rate of VEGF cleavage. 4 μg of recombinant human VEGF165 was incubated with 0.18 μg of purified protease in PBS/pH 7.4 at room temperature. Aliquots were taken at the indicated time points and analysed on a polyacrylamide gel. The extend of cleavage was quantified by densitometric analysis of the bands. The activity is plotted over incubation time in FIG. 18. Specific cleavage was controlled by further SDS polyacrylamide gel analyses.

The invention claimed is:

1. A recombinant engineered enzyme with catalytic activity of defined specificity, characterized by a combination of the following components:
   (a) a protein scaffold capable of catalyzing at least one protein cleavage reaction on at least one target substrate and being a serine protease of the structural class S1, and
   (b) one or more specificity determining regions (SDRs), wherein the SDRs are peptide sequences inserted into the protein scaffold at one or more positions that correspond structurally or by amino acid sequence homology to the regions 38-48 and 122-130 in human trypsin I having the amino acid sequence shown in SEQ ID NO:1, wherein the inserted SDRs enable the resulting engineered protein to discriminate between at least one target substrate and one or more different substrates.

2. The recombinant engineered enzyme of claim 1, wherein the SDRs (b) have a length of less than 50 amino acid residues.

3. The recombinant engineered enzyme of claim 2, wherein the SDRs (b) have a length between two and 20 amino acid residues.

4. The recombinant engineered enzyme of claim 3, wherein the SDRs (b) have a length between two and ten amino acid residues.

5. The recombinant engineered enzyme of claim 4, wherein the SDRs (b) have a length between three and eight amino acid residues.

6. The recombinant engineered enzyme of claim 2, wherein the number of SDRs is at least one.

7. The recombinant engineered enzyme of claim 6, wherein the number of SDRs is more than one.

8. The recombinant engineered enzyme of claim 6, wherein the number of SDRs is between two and eleven.

9. The recombinant engineered enzyme of claim 6, wherein the number of SDRs is between two and six.

10. The recombinant engineered enzyme of claim 1, wherein the protein scaffold (a) is encoded by a gene of viral origin.

11. The recombinant engineered enzyme of claim 1, wherein the protein scaffold (a) is encoded by a gene of prokaryotic origin.

12. The recombinant engineered enzyme of claim 1, wherein the protein scaffold (a) is encoded by a gene of eukaryotic origin.

13. The recombinant engineered enzyme of claim 1, wherein the protein scaffold (a) is comprised of one or more polypeptides derived from the same or different native enzymes.

14. The recombinant engineered enzyme of claim 1, wherein the protein scaffold (a) is comprised of one or more polypeptides derived from the same or different native mammalian enzymes.

15. The recombinant engineered enzyme of claim 14, wherein the mammalian enzymes are human enzymes.

16. A fusion protein comprised of at least one recombinant engineered enzyme of claim 1 and at least one further proteinacious component.

17. The fusion protein of claim 16, wherein the further proteinacious component is selected from the group consisting of binding domains and fragments thereof.

18. A fusion protein comprised of at least one recombinant engineered enzyme of claim 1 and at least one further functional component.

19. The fusion protein of claim 18, wherein the functional component is selected from the group consisting of polyethylenglycols, and fragments or derivatives thereof.

20. A composition comprising one or more recombinant engineered enzymes of claim 1.

21. A composition comprising the fusion protein of claim 18.

22. A composition comprising the fusion protein of claim 19.

23. The composition of claim 20, which is a research composition.

24. The composition of claim 21, which is a research composition.

25. The composition of claim 22, which is a research composition.

26. The composition of claim 20, which further comprises a pharmceutically acceptable carrier(s).

27. The composition of claim 21, which further comprises a pharmaceutically acceptable carrier(s).

28. The composition of claim 22, which further comprises a pharmaceutically acceptable carrier(s).

29. The recombinant engineered enzyme of claim 1, wherein the SDRs are located at one or more positions selected from the group of positions that correspond structurally or by amino acid sequence homology to the regions 41-45 and 125-128 in human trypsin I having the amino acid sequence shown in SEQ ID NO:1.

* * * * *

SEQUENCE LISTING

```
<160> NUMBER OF SEQ ID NOS: 113

<210> SEQ ID NO 1
<211> LENGTH: 224
<212> TYPE: PRT
<213> ORGANISM: Homo sapiens

<400> SEQUENCE: 1

Ile Val Gly Gly Tyr Asn Cys Glu Glu Asn Ser Val Pro Tyr Gln Val
1               5                   10                  15

Ser Leu Asn Ser Gly Tyr His Phe Cys Gly Gly Ser Leu Ile Asn Glu
            20                  25                  30

Gln Trp Val Val Ser Ala Gly His Cys Tyr Lys Ser Arg Ile Gln Val
        35                  40                  45

Arg Leu Gly Glu His Asn Ile Glu Val Leu Glu Gly Asn Glu Gln Phe
    50                  55                  60

Ile Asn Ala Ala Lys Ile Ile Arg His Pro Gln Tyr Asp Arg Lys Thr
65                  70                  75                  80

Leu Asn Asn Asp Ile Met Leu Ile Lys Leu Ser Ser Arg Ala Val Ile
                85                  90                  95

Asn Ala Arg Val Ser Thr Ile Ser Leu Pro Thr Ala Pro Pro Ala Thr
            100                 105                 110

Gly Thr Lys Cys Leu Ile Ser Gly Trp Gly Asn Thr Ala Ser Ser Gly
        115                 120                 125

Ala Asp Tyr Pro Asp Glu Leu Gln Cys Leu Asp Ala Pro Val Leu Ser
    130                 135                 140

Gln Ala Lys Cys Glu Ala Ser Tyr Pro Gly Lys Ile Thr Ser Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Cys Asn Gly Gln Leu Gln Gly Val Val Ser
            180                 185                 190

Trp Gly Asp Gly Cys Ala Gln Lys Asn Lys Pro Gly Val Tyr Thr Lys
        195                 200                 205

Val Tyr Asn Tyr Val Lys Trp Ile Lys Asn Thr Ile Ala Ala Asn Ser
    210                 215                 220

<210> SEQ ID NO 2
<211> LENGTH: 235
<212> TYPE: PRT
<213> ORGANISM: artificial sequence
<220> FEATURE:
<223> OTHER INFORMATION: trypsin variant 1
```

```
<400> SEQUENCE: 2

Ile Val Gly Gly Tyr Asn Cys Glu Glu Asn Ser Val Pro Tyr Gln Val
1               5                   10                  15

Ser Leu Asn Ser Gly Tyr His Phe Cys Gly Gly Ser Leu Ile Asn Glu
                20                  25                  30

Gln Trp Val Val Ser Ala Gly His Cys Tyr Asp Ala Val Gly Arg Asp
            35                  40                  45

Lys Ser Arg Ile Gln Val Arg Leu Gly Glu His Asn Ile Glu Val Leu
        50                  55                  60

Glu Gly Asn Glu Gln Phe Ile Asn Ala Ala Lys Ile Ile Arg His Pro
65                  70                  75                  80

Gln Tyr Asp Arg Lys Thr Leu Asn Asn Asp Ile Met Leu Ile Lys Leu
                85                  90                  95

Ser Ser Arg Ala Val Ile Asn Ala Arg Val Ser Thr Ile Ser Leu Pro
                100                 105                 110

Thr Ala Pro Pro Ala Thr Gly Thr Lys Cys Leu Ile Ser Gly Trp Gly
            115                 120                 125

Asn Thr Ile Thr Asn Ser Thr Ala Ser Ser Gly Ala Asp Tyr Pro Asp
        130                 135                 140

Glu Leu Gln Cys Leu Asp Ala Pro Val Leu Ser Gln Ala Lys Cys Glu
145                 150                 155                 160

Ala Ser Tyr Pro Gly Lys Ile Thr Ser Asn Met Phe Cys Val Gly Phe
                165                 170                 175

Leu Glu Gly Gly Lys Asp Ser Cys Gln Gly Asp Ser Gly Gly Pro Val
            180                 185                 190

Val Cys Asn Gly Gln Leu Gln Gly Val Val Ser Trp Gly Asp Gly Cys
        195                 200                 205

Ala Gln Lys Asn Lys Pro Gly Val Tyr Thr Lys Val Tyr Asn Tyr Val
    210                 215                 220

Lys Trp Ile Lys Asn Thr Ile Ala Ala Asn Ser
225                 230                 235

<210> SEQ ID NO 3
<211> LENGTH: 235
<212> TYPE: PRT
<213> ORGANISM: artificial sequence
<220> FEATURE:
<223> OTHER INFORMATION: trypsin variant 2

<400> SEQUENCE: 3

Ile Val Gly Gly Tyr Asn Cys Glu Glu Asn Ser Val Pro Tyr Gln Val
1               5                   10                  15

Ser Leu Asn Ser Gly Tyr His Phe Cys Gly Gly Ser Leu Ile Asn Glu
                20                  25                  30

Gln Trp Val Val Ser Ala Gly His Cys Tyr Asn Gly Arg Asp Leu Glu
            35                  40                  45

Lys Ser Arg Ile Gln Val Arg Leu Gly Glu His Asn Ile Glu Val Leu
        50                  55                  60

Glu Gly Asn Glu Gln Phe Ile Asn Ala Ala Lys Ile Ile Arg His Pro
65                  70                  75                  80

Gln Tyr Asp Arg Lys Thr Leu Asn Asn Asp Ile Met Leu Ile Lys Leu
                85                  90                  95

Ser Ser Arg Ala Val Ile Asn Ala Arg Val Ser Thr Ile Ser Leu Pro
                100                 105                 110
```

```
Thr Ala Pro Pro Ala Thr Gly Thr Lys Cys Leu Ile Ser Gly Trp Gly
        115                 120                 125

Asn Val Arg Gly Thr Trp Thr Ala Ser Ser Gly Ala Asp Tyr Pro Asp
    130                 135                 140

Glu Leu Gln Cys Leu Asp Ala Pro Val Leu Ser Gln Ala Lys Cys Glu
145                 150                 155                 160

Ala Ser Tyr Pro Gly Lys Ile Thr Ser Asn Met Phe Cys Val Gly Phe
                165                 170                 175

Leu Glu Gly Gly Lys Asp Ser Cys Gln Gly Asp Ser Gly Gly Pro Val
            180                 185                 190

Val Cys Asn Gly Gln Leu Gln Gly Val Val Ser Trp Gly Asp Gly Cys
        195                 200                 205

Ala Gln Lys Asn Lys Pro Gly Val Tyr Thr Lys Val Tyr Asn Tyr Val
    210                 215                 220

Lys Trp Ile Lys Asn Thr Ile Ala Ala Asn Ser
225                 230                 235

<210> SEQ ID NO 4
<211> LENGTH: 235
<212> TYPE: PRT
<213> ORGANISM: artificial sequence
<220> FEATURE:
<223> OTHER INFORMATION: trypsin variant 3

<400> SEQUENCE: 4

Ile Val Gly Gly Tyr Asn Cys Glu Glu Asn Ser Val Pro Tyr Gln Val
1               5                   10                  15

Ser Leu Asn Ser Gly Tyr His Phe Cys Gly Gly Ser Leu Ile Asn Glu
                20                  25                  30

Gln Trp Val Val Ser Ala Gly His Cys Tyr Ala Ala Thr Asn Gly Asp
            35                  40                  45

Lys Ser Arg Ile Gln Val Arg Leu Gly Glu His Asn Ile Glu Val Leu
    50                  55                  60

Glu Gly Asn Glu Gln Phe Ile Asn Ala Ala Lys Ile Ile Arg His Pro
65                  70                  75                  80

Gln Tyr Asp Arg Lys Thr Leu Asn Asn Asp Ile Met Leu Ile Lys Leu
                85                  90                  95

Ser Ser Arg Ala Val Ile Asn Ala Arg Val Ser Thr Ile Ser Leu Pro
            100                 105                 110

Thr Ala Pro Pro Ala Thr Gly Thr Lys Cys Leu Ile Ser Gly Trp Gly
        115                 120                 125

Asn Arg Lys Asp Phe Trp Thr Ala Ser Ser Gly Ala Asp Tyr Pro Asp
    130                 135                 140

Glu Leu Gln Cys Leu Asp Ala Pro Val Leu Ser Gln Ala Lys Cys Glu
145                 150                 155                 160

Ala Ser Tyr Pro Gly Lys Ile Thr Ser Asn Met Phe Cys Val Gly Phe
                165                 170                 175

Leu Glu Gly Gly Lys Asp Ser Cys Gln Gly Asp Ser Gly Gly Pro Val
            180                 185                 190

Val Cys Asn Gly Gln Leu Gln Gly Val Val Ser Trp Gly Asp Gly Cys
        195                 200                 205

Ala Gln Lys Asn Lys Pro Gly Val Tyr Thr Lys Val Tyr Asn Tyr Val
    210                 215                 220

Lys Trp Ile Lys Asn Thr Ile Ala Ala Asn Ser
225                 230                 235
```

```
<210> SEQ ID NO 5
<211> LENGTH: 259
<212> TYPE: PRT
<213> ORGANISM: Homo sapiens

<400> SEQUENCE: 5

Ile Val Glu Gly Ser Asp Ala Glu Ile Gly Met Ser Pro Trp Gln Val
1               5                   10                  15

Met Leu Phe Arg Lys Ser Pro Gln Glu Leu Leu Cys Gly Ala Ser Leu
            20                  25                  30

Ile Ser Asp Arg Trp Val Leu Thr Ala Ala His Cys Leu Leu Tyr Pro
        35                  40                  45

Pro Trp Asp Lys Asn Phe Thr Glu Asn Asp Leu Leu Val Arg Ile Gly
    50                  55                  60

Lys His Ser Arg Thr Arg Tyr Glu Arg Asn Ile Glu Lys Ile Ser Met
65                  70                  75                  80

Leu Glu Lys Ile Tyr Ile His Pro Arg Tyr Asn Trp Arg Glu Asn Leu
                85                  90                  95

Asp Arg Asp Ile Ala Leu Met Lys Leu Lys Lys Pro Val Ala Phe Ser
            100                 105                 110

Asp Tyr Ile His Pro Val Cys Leu Pro Asp Arg Glu Thr Ala Ala Ser
        115                 120                 125

Leu Leu Gln Ala Gly Tyr Lys Gly Arg Val Thr Gly Trp Gly Asn Leu
    130                 135                 140

Lys Glu Thr Trp Thr Ala Asn Val Gly Lys Gly Gln Pro Ser Val Leu
145                 150                 155                 160

Gln Val Val Asn Leu Pro Ile Val Glu Arg Pro Val Cys Lys Asp Ser
                165                 170                 175

Thr Arg Ile Arg Ile Thr Asp Asn Met Phe Cys Ala Gly Tyr Lys Pro
            180                 185                 190

Asp Glu Gly Lys Arg Gly Asp Ala Cys Glu Gly Asp Ser Gly Gly Pro
        195                 200                 205

Phe Val Met Lys Ser Pro Phe Asn Asn Arg Trp Tyr Gln Met Gly Ile
    210                 215                 220

Val Ser Trp Gly Glu Gly Cys Asp Arg Asp Gly Lys Tyr Gly Phe Tyr
225                 230                 235                 240

Thr His Val Phe Arg Leu Lys Lys Trp Ile Gln Lys Val Ile Asp Gln
                245                 250                 255

Phe Gly Glu

<210> SEQ ID NO 6
<211> LENGTH: 235
<212> TYPE: PRT
<213> ORGANISM: Homo sapiens

<400> SEQUENCE: 6

Ile Val Gly Gly Ser Asn Ala Lys Glu Gly Ala Trp Pro Trp Val Val
1               5                   10                  15

Gly Leu Tyr Tyr Gly Gly Arg Leu Leu Cys Gly Ala Ser Leu Val Ser
            20                  25                  30

Ser Asp Trp Leu Val Ser Ala Ala His Cys Val Tyr Gly Arg Asn Leu
        35                  40                  45

Glu Pro Ser Lys Trp Thr Ala Ile Leu Gly Leu His Met Lys Ser Asn
    50                  55                  60

Leu Thr Ser Pro Gln Thr Val Pro Arg Leu Ile Asp Glu Ile Val Ile
```

-continued

```
            65                  70                  75                  80
Asn Pro His Tyr Asn Arg Arg Lys Asp Asn Asp Ile Ala Met Met
                85                  90                  95

His Leu Glu Phe Lys Val Asn Tyr Thr Asp Tyr Ile Gln Pro Ile Cys
                100                 105                 110

Leu Pro Glu Glu Asn Gln Val Phe Pro Pro Gly Arg Asn Cys Ser Ile
                115                 120                 125

Ala Gly Trp Gly Thr Val Val Tyr Gln Gly Thr Thr Ala Asn Ile Leu
            130                 135                 140

Gln Glu Ala Asp Val Pro Leu Leu Ser Asn Glu Arg Cys Gln Gln Gln
145                 150                 155                 160

Met Pro Glu Tyr Asn Ile Thr Glu Asn Met Ile Cys Ala Gly Tyr Glu
                165                 170                 175

Glu Gly Gly Ile Asp Ser Cys Gln Gly Asp Ser Gly Gly Pro Leu Met
                180                 185                 190

Cys Gln Glu Asn Asn Arg Trp Phe Leu Ala Gly Val Thr Ser Phe Gly
                195                 200                 205

Tyr Lys Cys Ala Leu Pro Asn Arg Pro Gly Val Tyr Ala Arg Val Ser
            210                 215                 220

Arg Phe Thr Glu Trp Ile Gln Ser Phe Leu His
225                 230                 235

<210> SEQ ID NO 7
<211> LENGTH: 275
<212> TYPE: PRT
<213> ORGANISM: Bacillus subtilis

<400> SEQUENCE: 7

Ile Ala His Glu Tyr Ala Gln Ser Val Pro Tyr Gly Ile Ser Gln Ile
1               5                   10                  15

Lys Ala Pro Ala Leu His Ser Gln Gly Tyr Thr Gly Ser Asn Val Lys
                20                  25                  30

Val Ala Val Ile Asp Ser Gly Ile Asp Ser Ser His Pro Asp Leu Asn
                35                  40                  45

Val Arg Gly Gly Ala Ser Phe Val Pro Ser Glu Thr Asn Pro Tyr Gln
50                  55                  60

Asp Gly Ser Ser His Gly Thr His Val Ala Gly Thr Ile Ala Ala Leu
65                  70                  75                  80

Asn Asn Ser Ile Gly Val Leu Gly Val Ser Pro Ser Ala Ser Leu Tyr
                85                  90                  95

Ala Val Lys Val Leu Asp Ser Thr Gly Ser Gly Gln Tyr Ser Trp Ile
                100                 105                 110

Ile Asn Gly Ile Glu Trp Ala Ile Ser Asn Asn Met Asp Val Ile Asn
            115                 120                 125

Met Ser Leu Gly Gly Pro Thr Gly Ser Thr Ala Leu Lys Thr Val Val
            130                 135                 140

Asp Lys Ala Val Ser Ser Gly Ile Val Val Ala Ala Ala Ala Gly Asn
145                 150                 155                 160

Glu Gly Ser Ser Gly Ser Thr Ser Thr Val Gly Tyr Pro Ala Lys Tyr
                165                 170                 175

Pro Ser Thr Ile Ala Val Gly Ala Val Asn Ser Ser Asn Gln Arg Ala
            180                 185                 190

Ser Phe Ser Ser Ala Gly Ser Glu Leu Asp Val Met Ala Pro Gly Val
            195                 200                 205
```

```
Ser Ile Gln Ser Thr Leu Pro Gly Gly Thr Tyr Gly Ala Tyr Asn Gly
    210                 215                 220
Thr Ser Met Ala Thr Pro His Val Ala Gly Ala Ala Leu Ile Leu
225                 230                 235                 240
Ser Lys His Pro Thr Trp Thr Asn Ala Gln Val Arg Asp Arg Leu Glu
            245                 250                 255
Ser Thr Ala Thr Tyr Leu Gly Asn Ser Phe Tyr Tyr Gly Lys Gly Leu
            260                 265                 270
Ile Asn Val
        275

<210> SEQ ID NO 8
<211> LENGTH: 320
<212> TYPE: PRT
<213> ORGANISM: Murinae gen. sp.

<400> SEQUENCE: 8

Val Ala Lys Arg Arg Ala Lys Arg Asp Val Tyr Gln Glu Pro Thr Asp
1               5                   10                  15
Pro Lys Phe Pro Gln Gln Trp Tyr Leu Ser Gly Val Thr Gln Arg Asp
            20                  25                  30
Leu Asn Val Lys Glu Ala Trp Ala Gln Gly Phe Thr Gly His Gly Ile
        35                  40                  45
Val Val Ser Ile Leu Asp Asp Gly Ile Glu Lys Asn His Pro Asp Leu
    50                  55                  60
Ala Gly Asn Tyr Asp Pro Gly Ala Ser Phe Asp Val Asn Asp Gln Asp
65                  70                  75                  80
Pro Asp Pro Gln Pro Arg Tyr Thr Gln Met Asn Asp Asn Arg His Gly
                85                  90                  95
Thr Arg Cys Ala Gly Glu Val Ala Ala Val Ala Asn Asn Gly Val Cys
            100                 105                 110
Gly Val Gly Val Ala Tyr Asn Ala Arg Ile Gly Gly Val Arg Met Leu
        115                 120                 125
Asp Gly Glu Val Thr Asp Ala Val Glu Ala Arg Ser Leu Gly Leu Asn
130                 135                 140
Pro Asn His Ile His Ile Tyr Ser Ala Ser Trp Gly Pro Glu Asp Asp
145                 150                 155                 160
Gly Lys Thr Val Asp Gly Pro Ala Arg Leu Ala Glu Glu Ala Phe Phe
                165                 170                 175
Arg Gly Val Ser Gln Gly Arg Gly Gly Leu Gly Ser Ile Phe Val Trp
            180                 185                 190
Ala Ser Gly Asn Gly Gly Arg Glu His Asp Ser Cys Asn Cys Asp Gly
        195                 200                 205
Tyr Thr Asn Ser Ile Tyr Thr Leu Ser Ile Ser Ser Ala Thr Gln Phe
    210                 215                 220
Gly Asn Val Pro Trp Tyr Ser Glu Ala Cys Ser Ser Thr Leu Ala Thr
225                 230                 235                 240
Thr Tyr Ser Ser Gly Asn Gln Asn Glu Lys Gln Ile Val Thr Thr Asp
                245                 250                 255
Leu Arg Gln Lys Cys Thr Glu Ser His Thr Gly Thr Ser Ala Ser Ala
            260                 265                 270
Pro Leu Ala Ala Gly Ile Ile Ala Leu Thr Leu Glu Ala Asn Lys Asn
        275                 280                 285
Leu Thr Trp Arg Asp Met Gln His Leu Val Val Gln Thr Ser Lys Pro
    290                 295                 300
```

```
Ala His Leu Asn Ala Asp Asp Trp Ala Thr Asn Gly Val Gly Arg Lys
305                 310                 315                 320
```

<210> SEQ ID NO 9
<211> LENGTH: 330
<212> TYPE: PRT
<213> ORGANISM: Homo sapiens

<400> SEQUENCE: 9

```
Glu Lys Glu Arg Ser Lys Arg Ser Ala Leu Arg Asp Ser Ala Leu Asn
1               5                   10                  15

Leu Phe Asn Asp Pro Met Trp Asn Gln Gln Trp Tyr Leu Gln Asp Thr
            20                  25                  30

Arg Met Thr Ala Ala Leu Pro Lys Leu Asp Leu His Val Ile Pro Val
        35                  40                  45

Trp Gln Lys Gly Ile Thr Gly Lys Gly Val Val Ile Thr Val Leu Asp
    50                  55                  60

Asp Gly Leu Glu Trp Asn His Thr Asp Ile Tyr Ala Asn Tyr Asp Pro
65                  70                  75                  80

Glu Ala Ser Tyr Asp Phe Asn Asp Asn Asp His Asp Pro Phe Pro Arg
                85                  90                  95

Tyr Asp Pro Thr Asn Glu Asn Lys His Gly Thr Arg Cys Ala Gly Glu
            100                 105                 110

Ile Ala Met Gln Ala Asn Asn His Lys Cys Gly Val Gly Val Ala Tyr
        115                 120                 125

Asn Ser Lys Val Gly Gly Ile Arg Met Leu Asp Gly Ile Val Thr Asp
130                 135                 140

Ala Ile Glu Ala Ser Ser Ile Gly Phe Asn Pro Gly His Val Asp Ile
145                 150                 155                 160

Tyr Ser Ala Ser Trp Gly Pro Asn Asp Asp Gly Lys Thr Val Glu Gly
                165                 170                 175

Pro Gly Arg Leu Ala Gln Lys Ala Phe Glu Tyr Gly Val Lys Gln Gly
            180                 185                 190

Arg Gln Gly Lys Gly Ser Ile Phe Val Trp Ala Ser Gly Asn Gly Gly
        195                 200                 205

Arg Gln Gly Asp Asn Cys Asp Cys Asp Gly Tyr Thr Asp Ser Ile Tyr
210                 215                 220

Thr Ile Ser Ile Ser Ser Ala Ser Gln Gln Gly Leu Ser Pro Trp Tyr
225                 230                 235                 240

Ala Glu Lys Cys Ser Ser Thr Leu Ala Thr Ser Tyr Ser Ser Gly Asp
                245                 250                 255

Tyr Thr Asp Gln Arg Ile Thr Ser Ala Asp Leu His Asn Asp Cys Thr
            260                 265                 270

Glu Thr His Thr Gly Thr Ser Ala Ser Ala Pro Leu Ala Ala Gly Ile
        275                 280                 285

Phe Ala Leu Ala Leu Glu Ala Asn Pro Asn Leu Thr Trp Arg Asp Met
290                 295                 300

Gln His Leu Val Val Trp Thr Ser Glu Tyr Asp Pro Leu Ala Asn Asn
305                 310                 315                 320

Pro Gly Trp Lys Lys Asn Gly Ala Gly Leu
                325                 330
```

<210> SEQ ID NO 10
<211> LENGTH: 297
<212> TYPE: PRT

<213> ORGANISM: Homo sapiens

<400> SEQUENCE: 10

```
Asn Thr His Pro Cys Gln Ser Asp Met Asn Ile Glu Gly Ala Trp Lys
1               5                   10                  15
Arg Gly Tyr Thr Gly Lys Asn Ile Val Val Thr Ile Leu Asp Asp Gly
            20                  25                  30
Ile Glu Arg Thr His Pro Asp Leu Met Gln Asn Tyr Asp Ala Leu Ala
        35                  40                  45
Ser Cys Asp Val Asn Gly Asn Asp Leu Asp Pro Met Pro Arg Tyr Asp
50                  55                  60
Ala Ser Asn Glu Asn Lys His Gly Thr Arg Cys Ala Gly Glu Val Ala
65                  70                  75                  80
Ala Ala Ala Asn Asn Ser His Cys Thr Val Gly Ile Ala Phe Asn Ala
                85                  90                  95
Lys Ile Gly Gly Val Arg Met Leu Asp Gly Asp Val Thr Asp Met Val
            100                 105                 110
Glu Ala Lys Ser Val Ser Phe Asn Pro Gln His Val His Ile Tyr Ser
        115                 120                 125
Ala Ser Trp Gly Pro Asp Asp Asp Gly Lys Thr Val Asp Gly Pro Ala
130                 135                 140
Pro Leu Thr Arg Gln Ala Phe Glu Asn Gly Val Arg Met Gly Arg Arg
145                 150                 155                 160
Gly Leu Gly Ser Val Phe Val Trp Ala Ser Gly Asn Gly Gly Arg Ser
                165                 170                 175
Lys Asp His Cys Ser Cys Asp Gly Tyr Thr Asn Ser Ile Tyr Thr Ile
            180                 185                 190
Ser Ile Ser Ser Thr Ala Glu Ser Gly Lys Lys Pro Trp Tyr Leu Glu
        195                 200                 205
Glu Cys Ser Ser Thr Leu Ala Thr Thr Tyr Ser Ser Gly Glu Ser Tyr
210                 215                 220
Asp Lys Lys Ile Ile Thr Thr Asp Leu Arg Gln Arg Cys Thr Asp Asn
225                 230                 235                 240
His Thr Gly Thr Ser Ala Ser Ala Pro Met Ala Ala Gly Ile Ile Ala
                245                 250                 255
Leu Ala Leu Glu Ala Asn Pro Phe Leu Thr Trp Arg Asp Val Gln His
            260                 265                 270
Val Ile Val Arg Thr Ser Arg Ala Gly His Leu Asn Ala Asn Asp Trp
        275                 280                 285
Lys Thr Asn Ala Ala Gly Phe Lys Val
    290                 295
```

<210> SEQ ID NO 11
<211> LENGTH: 328
<212> TYPE: PRT
<213> ORGANISM: Homo sapiens

<400> SEQUENCE: 11

```
Thr Leu Val Asp Glu Gln Pro Leu Glu Asn Tyr Leu Asp Met Glu Tyr
1               5                   10                  15
Phe Gly Thr Ile Gly Ile Gly Thr Pro Ala Gln Asp Phe Thr Val Val
            20                  25                  30
Phe Asp Thr Gly Ser Ser Asn Leu Trp Val Pro Ser Val Tyr Cys Ser
        35                  40                  45
Ser Leu Ala Cys Thr Asn His Asn Arg Phe Asn Pro Glu Asp Ser Ser
```

-continued

```
                50                  55                  60
Thr Tyr Gln Ser Thr Ser Glu Thr Val Ser Ile Thr Tyr Gly Thr Gly
 65                  70                  75                  80

Ser Met Thr Gly Ile Leu Gly Tyr Asp Thr Val Gln Val Gly Gly Ile
                 85                  90                  95

Ser Asp Thr Asn Gln Ile Phe Gly Leu Ser Glu Thr Glu Pro Gly Ser
                100                 105                 110

Phe Leu Tyr Tyr Ala Pro Phe Asp Gly Ile Leu Gly Leu Ala Tyr Pro
                115                 120                 125

Ser Ile Ser Ser Ser Gly Ala Thr Pro Val Phe Asp Asn Ile Trp Asn
130                 135                 140

Gln Gly Leu Val Ser Gln Asp Leu Phe Ser Val Tyr Leu Ser Ala Asp
145                 150                 155                 160

Asp Lys Ser Gly Ser Val Val Ile Phe Gly Gly Ile Asp Ser Ser Tyr
                165                 170                 175

Tyr Thr Gly Ser Leu Asn Trp Val Pro Val Thr Val Glu Gly Tyr Trp
                180                 185                 190

Gln Ile Thr Val Asp Ser Ile Thr Met Asn Gly Glu Thr Ile Ala Cys
                195                 200                 205

Ala Glu Gly Cys Gln Ala Ile Val Asp Thr Gly Thr Ser Leu Leu Thr
210                 215                 220

Gly Pro Thr Ser Pro Ile Ala Asn Ile Gln Ser Asp Ile Gly Ala Ser
225                 230                 235                 240

Glu Asn Ser Asp Gly Asp Met Val Val Ser Cys Ser Ala Ile Ser Ser
                245                 250                 255

Leu Pro Asp Ile Val Phe Thr Ile Asn Gly Val Gln Tyr Pro Val Pro
                260                 265                 270

Pro Ser Ala Tyr Ile Leu Gln Ser Glu Gly Ser Cys Ile Ser Gly Phe
                275                 280                 285

Gln Gly Met Asn Val Pro Thr Glu Ser Gly Glu Leu Trp Ile Leu Gly
                290                 295                 300

Asp Val Phe Ile Arg Gln Tyr Phe Thr Val Phe Asp Arg Ala Asn Asn
305                 310                 315                 320

Gln Val Gly Leu Ala Pro Val Ala
                325

<210> SEQ ID NO 12
<211> LENGTH: 358
<212> TYPE: PRT
<213> ORGANISM: Homo sapiens

<400> SEQUENCE: 12

Glu Met Val Asp Asn Leu Arg Gly Lys Ser Gly Gln Gly Tyr Tyr Val
 1               5                  10                  15

Glu Met Thr Val Gly Ser Pro Pro Gln Thr Leu Asn Ile Leu Val Asp
                 20                  25                  30

Thr Gly Ser Ser Asn Phe Ala Val Gly Ala Ala Pro His Pro Phe Leu
                 35                  40                  45

His Arg Tyr Tyr Gln Arg Gln Leu Ser Ser Thr Tyr Arg Asp Leu Arg
     50                  55                  60

Lys Gly Val Tyr Val Pro Tyr Thr Gln Gly Lys Trp Glu Gly Glu Leu
 65                  70                  75                  80

Gly Thr Asp Leu Val Ser Ile Pro His Gly Pro Asn Val Thr Val Arg
                 85                  90                  95
```

```
Ala Asn Ile Ala Ala Ile Thr Glu Ser Asp Lys Phe Phe Ile Asn Gly
            100                 105                 110

Ser Asn Trp Glu Gly Ile Leu Gly Leu Ala Tyr Ala Glu Ile Ala Arg
        115                 120                 125

Pro Asp Asp Ser Leu Glu Pro Phe Phe Asp Ser Leu Val Lys Gln Thr
    130                 135                 140

His Val Pro Asn Leu Phe Ser Leu Gln Leu Cys Gly Ala Gly Phe Pro
145                 150                 155                 160

Leu Asn Gln Ser Glu Val Leu Ala Ser Val Gly Gly Ser Met Ile Ile
                165                 170                 175

Gly Gly Ile Asp His Ser Leu Tyr Thr Gly Ser Leu Trp Tyr Thr Pro
            180                 185                 190

Ile Arg Arg Glu Trp Tyr Tyr Glu Val Ile Ile Val Arg Val Glu Ile
        195                 200                 205

Asn Gly Gln Asp Leu Lys Met Asp Cys Lys Glu Tyr Asn Tyr Asp Lys
    210                 215                 220

Ser Ile Val Asp Ser Gly Thr Thr Asn Leu Arg Leu Pro Lys Lys Val
225                 230                 235                 240

Phe Glu Ala Ala Val Lys Ser Ile Lys Ala Ala Ser Ser Thr Glu Lys
                245                 250                 255

Phe Pro Asp Gly Phe Trp Leu Gly Glu Gln Leu Val Cys Trp Gln Ala
            260                 265                 270

Gly Thr Thr Pro Trp Asn Ile Phe Pro Val Ile Ser Leu Tyr Leu Met
        275                 280                 285

Gly Glu Val Thr Asn Gln Ser Phe Arg Ile Thr Ile Leu Pro Gln Gln
    290                 295                 300

Tyr Leu Arg Pro Val Glu Asp Val Ala Thr Ser Gln Asp Asp Cys Tyr
305                 310                 315                 320

Lys Phe Ala Ile Ser Gln Ser Ser Thr Gly Thr Val Met Gly Ala Val
                325                 330                 335

Ile Met Glu Gly Phe Tyr Val Val Phe Asp Arg Ala Arg Lys Arg Ile
            340                 345                 350

Gly Phe Ala Val Ser Ala
        355

<210> SEQ ID NO 13
<211> LENGTH: 351
<212> TYPE: PRT
<213> ORGANISM: Homo sapiens

<400> SEQUENCE: 13

Pro Ala Val Thr Glu Gly Pro Ile Pro Glu Val Leu Lys Asn Tyr Met
1               5                   10                  15

Asp Ala Gln Tyr Tyr Gly Glu Ile Gly Ile Gly Thr Pro Pro Gln Cys
                20                  25                  30

Phe Thr Val Val Phe Asp Thr Gly Ser Ser Asn Leu Trp Val Pro Ser
            35                  40                  45

Ile His Cys Lys Leu Leu Asp Ile Ala Cys Trp Ile His His Lys Tyr
        50                  55                  60

Asn Ser Asp Lys Ser Ser Thr Tyr Val Lys Asn Gly Thr Ser Phe Asp
65                  70                  75                  80

Ile His Tyr Gly Ser Gly Ser Leu Ser Gly Tyr Leu Ser Gln Asp Thr
                85                  90                  95

Val Ser Val Pro Cys Gln Ser Ala Ser Ser Ala Ser Ala Leu Gly Gly
            100                 105                 110
```

```
Val Lys Val Glu Arg Gln Val Phe Gly Glu Ala Thr Lys Gln Pro Gly
        115                 120                 125

Ile Thr Phe Ile Ala Ala Lys Phe Asp Gly Ile Leu Gly Met Ala Tyr
130                 135                 140

Pro Arg Ile Ser Val Asn Asn Val Leu Pro Val Phe Asp Asn Leu Met
145                 150                 155                 160

Gln Gln Lys Leu Val Asp Gln Asn Ile Phe Ser Phe Tyr Leu Ser Arg
                165                 170                 175

Asp Pro Asp Ala Gln Pro Gly Gly Glu Leu Met Leu Gly Gly Thr Asp
            180                 185                 190

Ser Lys Tyr Tyr Lys Gly Ser Leu Ser Tyr Leu Asn Val Thr Arg Lys
        195                 200                 205

Ala Tyr Trp Gln Val His Leu Asp Gln Val Glu Val Ala Ser Gly Leu
210                 215                 220

Thr Leu Cys Lys Glu Gly Cys Glu Ala Ile Val Asp Thr Gly Thr Ser
225                 230                 235                 240

Leu Met Val Gly Pro Val Asp Glu Val Arg Glu Leu Gln Lys Ala Ile
                245                 250                 255

Gly Ala Val Pro Leu Ile Gln Gly Glu Tyr Met Ile Pro Cys Glu Lys
            260                 265                 270

Val Ser Thr Leu Pro Ala Ile Thr Leu Lys Leu Gly Gly Lys Gly Tyr
        275                 280                 285

Lys Leu Ser Pro Glu Asp Tyr Thr Leu Lys Val Ser Gln Ala Gly Lys
290                 295                 300

Thr Leu Cys Leu Ser Gly Phe Met Gly Met Asp Ile Pro Pro Pro Ser
305                 310                 315                 320

Gly Pro Leu Trp Ile Leu Gly Asp Val Phe Ile Gly Arg Tyr Tyr Thr
                325                 330                 335

Val Phe Asp Arg Asp Asn Asn Arg Val Gly Phe Ala Glu Ala Ala
            340                 345                 350

<210> SEQ ID NO 14
<211> LENGTH: 305
<212> TYPE: PRT
<213> ORGANISM: Homo sapiens

<400> SEQUENCE: 14

Met Leu Glu Ala Asp Asp Gln Gly Cys Ile Glu Glu Gln Gly Val Glu
1               5                   10                  15

Asp Ser Ala Asn Glu Asp Ser Val Asp Ala Lys Pro Asp Arg Ser Ser
                20                  25                  30

Phe Val Pro Ser Leu Phe Ser Lys Lys Lys Lys Asn Val Thr Met Arg
            35                  40                  45

Ser Ile Lys Thr Thr Arg Asp Arg Val Pro Thr Tyr Gln Tyr Asn Met
50                  55                  60

Asn Phe Glu Lys Leu Gly Lys Cys Ile Ile Asn Asn Lys Asn Phe
65                  70                  75                  80

Asp Lys Val Thr Gly Met Gly Val Arg Asn Gly Thr Asp Lys Asp Ala
                85                  90                  95

Glu Ala Leu Phe Lys Cys Phe Arg Ser Leu Gly Phe Asp Val Ile Val
            100                 105                 110

Tyr Asn Asp Cys Ser Cys Ala Lys Met Gln Asp Leu Leu Lys Lys Ala
        115                 120                 125

Ser Glu Glu Asp His Thr Asn Ala Ala Cys Phe Ala Cys Ile Leu Leu
```

```
                130                 135                 140
Ser His Gly Glu Glu Asn Val Ile Tyr Gly Lys Asp Gly Val Thr Pro
145                 150                 155                 160

Ile Lys Asp Leu Thr Ala His Phe Arg Gly Asp Arg Ser Lys Thr Leu
            165                 170                 175

Leu Glu Lys Pro Lys Leu Phe Phe Ile Gln Ala Cys Arg Gly Thr Glu
            180                 185                 190

Leu Asp Asp Gly Ile Gln Ala Asp Ser Gly Pro Ile Asn Asp Thr Asp
            195                 200                 205

Ala Asn Pro Arg Tyr Lys Ile Pro Val Glu Ala Asp Phe Leu Phe Ala
210                 215                 220

Tyr Ser Thr Val Pro Gly Tyr Tyr Ser Trp Arg Ser Pro Gly Arg Gly
225                 230                 235                 240

Ser Trp Phe Val Gln Ala Leu Cys Ser Ile Leu Glu Glu His Gly Lys
            245                 250                 255

Asp Leu Glu Ile Met Gln Ile Leu Thr Arg Val Asn Asp Arg Val Ala
            260                 265                 270

Arg His Phe Glu Ser Gln Ser Asp Asp Pro His Phe His Glu Lys Lys
            275                 280                 285

Gln Ile Pro Cys Val Val Ser Met Leu Thr Lys Glu Leu Tyr Phe Ser
            290                 295                 300

Gln
305

<210> SEQ ID NO 15
<211> LENGTH: 262
<212> TYPE: PRT
<213> ORGANISM: Streptomyces sp. K15

<400> SEQUENCE: 15

Val Thr Lys Pro Thr Ile Ala Ala Val Gly Gly Tyr Ala Met Asn Asn
1               5                   10                  15

Gly Thr Gly Thr Thr Leu Tyr Thr Lys Ala Ala Asp Thr Arg Arg Ser
            20                  25                  30

Thr Gly Ser Thr Thr Lys Ile Met Thr Ala Lys Val Val Leu Ala Gln
        35                  40                  45

Ser Asn Leu Asn Leu Asp Ala Lys Val Thr Ile Gln Lys Ala Tyr Ser
    50                  55                  60

Asp Tyr Val Val Ala Asn Asn Ala Ser Gln Ala His Leu Ile Val Gly
65                  70                  75                  80

Asp Lys Val Thr Val Arg Gln Leu Leu Tyr Gly Leu Met Leu Pro Ser
                85                  90                  95

Gly Cys Asp Ala Ala Tyr Ala Leu Ala Asp Lys Tyr Gly Ser Gly Ser
            100                 105                 110

Thr Arg Ala Ala Arg Val Lys Ser Phe Ile Gly Lys Met Asn Thr Ala
        115                 120                 125

Ala Thr Asn Leu Gly Leu His Asn Thr His Phe Asp Ser Phe Asp Gly
    130                 135                 140

Ile Gly Asn Gly Ala Asn Tyr Ser Thr Pro Arg Asp Leu Thr Lys Ile
145                 150                 155                 160

Ala Ser Ser Ala Met Lys Asn Ser Thr Phe Arg Thr Val Val Lys Thr
                165                 170                 175

Lys Ala Tyr Thr Ala Lys Thr Val Thr Lys Thr Gly Ser Ile Arg Thr
            180                 185                 190
```

Met Asp Thr Trp Lys Asn Thr Asn Gly Leu Leu Ser Ser Tyr Ser Gly
        195                 200                 205

Ala Ile Gly Val Lys Thr Gly Ser Gly Pro Glu Ala Lys Tyr Cys Leu
    210                 215                 220

Val Phe Ala Ala Thr Arg Gly Lys Thr Val Ile Gly Thr Val Leu
225                 230                 235                 240

Ala Ser Thr Ser Ile Pro Ala Arg Glu Ser Asp Ala Thr Lys Ile Met
                245                 250                 255

Asn Tyr Gly Phe Ala Leu
            260

<210> SEQ ID NO 16
<211> LENGTH: 256
<212> TYPE: PRT
<213> ORGANISM: Human cytomegalovirus

<400> SEQUENCE: 16

Met Thr Met Asp Glu Gln Gln Ser Gln Ala Val Ala Pro Val Tyr Val
1               5                   10                  15

Gly Gly Phe Leu Ala Arg Tyr Asp Gln Ser Pro Asp Glu Ala Glu Leu
            20                  25                  30

Leu Leu Pro Arg Asp Val Val Glu His Trp Leu His Ala Gln Gly Gln
        35                  40                  45

Gly Gln Pro Ser Leu Ser Val Ala Leu Pro Leu Asn Ile Asn His Asp
    50                  55                  60

Asp Thr Ala Val Val Gly His Val Ala Ala Met Gln Ser Val Arg Asp
65                  70                  75                  80

Gly Leu Phe Cys Leu Gly Cys Val Thr Ser Pro Arg Phe Leu Glu Ile
                85                  90                  95

Val Arg Arg Ala Ser Glu Lys Ser Glu Leu Val Ser Arg Gly Pro Val
            100                 105                 110

Ser Pro Leu Gln Pro Asp Lys Val Val Glu Phe Leu Ser Gly Ser Tyr
        115                 120                 125

Ala Gly Leu Ser Leu Ser Ser Arg Arg Cys Asp Asp Val Glu Gln Ala
    130                 135                 140

Thr Ser Leu Ser Gly Ser Glu Thr Thr Pro Phe Lys His Val Ala Leu
145                 150                 155                 160

Cys Ser Val Gly Arg Arg Gly Thr Leu Ala Val Tyr Gly Arg Asp
                165                 170                 175

Pro Glu Trp Val Thr Gln Arg Phe Pro Asp Leu Thr Ala Ala Asp Arg
            180                 185                 190

Asp Gly Leu Arg Ala Gln Trp Gln Arg Cys Gly Ser Thr Ala Val Asp
        195                 200                 205

Ala Ser Gly Asp Pro Phe Arg Ser Asp Ser Tyr Gly Leu Leu Gly Asn
    210                 215                 220

Ser Val Asp Ala Leu Tyr Ile Arg Glu Arg Leu Pro Lys Leu Arg Tyr
225                 230                 235                 240

Asp Lys Gln Leu Val Gly Val Thr Glu Arg Glu Ser Tyr Val Lys Ala
            245                 250                 255

<210> SEQ ID NO 17
<211> LENGTH: 248
<212> TYPE: PRT
<213> ORGANISM: Escherichia coli

<400> SEQUENCE: 17

-continued

```
Val Arg Ser Phe Ile Tyr Glu Pro Phe Gln Ile Pro Ser Gly Ser Met
1               5                   10                  15

Met Pro Thr Leu Leu Ile Gly Asp Phe Ile Leu Val Glu Lys Phe Ala
            20                  25                  30

Tyr Gly Ile Lys Asp Pro Ile Tyr Gln Lys Thr Leu Ile Glu Thr Gly
        35                  40                  45

His Pro Lys Arg Gly Asp Ile Val Val Phe Lys Tyr Pro Glu Asp Pro
    50                  55                  60

Lys Leu Asp Tyr Ile Lys Arg Ala Val Gly Leu Pro Gly Asp Lys Val
65                  70                  75                  80

Thr Tyr Asp Pro Val Ser Lys Glu Leu Thr Ile Gln Pro Gly Cys Ser
                85                  90                  95

Ser Gly Gln Ala Cys Glu Asn Ala Leu Pro Val Thr Tyr Ser Asn Val
            100                 105                 110

Glu Pro Ser Asp Phe Val Gln Thr Phe Ser Arg Arg Asn Gly Gly Glu
        115                 120                 125

Ala Thr Ser Gly Phe Phe Glu Val Pro Lys Asn Glu Thr Lys Glu Asn
    130                 135                 140

Gly Ile Arg Leu Ser Glu Arg Lys Glu Thr Leu Gly Asp Val Thr His
145                 150                 155                 160

Arg Ile Leu Thr Val Pro Ile Ala Gln Asp Gln Val Gly Met Tyr Tyr
                165                 170                 175

Gln Gln Pro Gly Gln Gln Leu Ala Thr Trp Ile Val Pro Pro Gly Gln
            180                 185                 190

Tyr Phe Met Met Gly Asp Asn Arg Asp Asn Ser Ala Asp Ser Arg Tyr
        195                 200                 205

Trp Gly Phe Val Pro Glu Ala Asn Leu Val Gly Arg Ala Thr Ala Ile
    210                 215                 220

Trp Met Ser Phe Asp Lys Gln Glu Gly Glu Trp Pro Thr Gly Leu Arg
225                 230                 235                 240

Leu Ser Arg Ile Gly Gly Ile His
                245
```

<210> SEQ ID NO 18
<211> LENGTH: 317
<212> TYPE: PRT
<213> ORGANISM: Serratia marcescens

<400> SEQUENCE: 18

```
Met Glu Gln Leu Arg Gly Leu Tyr Pro Pro Leu Ala Ala Tyr Asp Ser
1               5                   10                  15

Gly Trp Leu Asp Thr Gly Asp Gly His Arg Ile Tyr Trp Glu Leu Ser
            20                  25                  30

Gly Asn Pro Asn Gly Lys Pro Ala Val Phe Ile His Gly Gly Pro Gly
        35                  40                  45

Gly Gly Ile Ser Pro His His Arg Gln Leu Phe Asp Pro Glu Arg Tyr
    50                  55                  60

Lys Val Leu Leu Phe Asp Gln Arg Gly Cys Gly Arg Ser Arg Pro His
65                  70                  75                  80

Ala Ser Leu Asp Asn Asn Thr Thr Trp His Leu Val Ala Asp Ile Glu
                85                  90                  95

Arg Leu Arg Glu Met Ala Gly Val Glu Gln Trp Leu Val Phe Gly Gly
            100                 105                 110

Ser Trp Gly Ser Thr Leu Ala Leu Ala Tyr Ala Gln Thr His Pro Glu
        115                 120                 125
```

```
Arg Val Ser Glu Met Val Leu Arg Gly Ile Phe Thr Leu Arg Lys Gln
    130                 135                 140

Arg Leu His Trp Tyr Tyr Gln Asp Gly Ala Ser Arg Phe Phe Pro Glu
145                 150                 155                 160

Lys Trp Glu Arg Val Leu Ser Ile Leu Ser Asp Asp Glu Arg Lys Asp
                165                 170                 175

Val Ile Ala Ala Tyr Arg Gln Arg Leu Thr Ser Ala Asp Pro Gln Val
            180                 185                 190

Gln Leu Glu Ala Ala Lys Leu Trp Ser Val Trp Glu Gly Glu Thr Val
        195                 200                 205

Thr Leu Leu Pro Ser Arg Glu Ser Ala Ser Phe Gly Glu Asp Asp Phe
    210                 215                 220

Ala Leu Ala Phe Ala Arg Ile Glu Asn His Tyr Phe Thr His Leu Gly
225                 230                 235                 240

Phe Leu Glu Ser Asp Asp Gln Leu Leu Arg Asn Val Pro Leu Ile Arg
                245                 250                 255

His Ile Pro Ala Val Ile Val His Gly Arg Tyr Asp Met Ala Cys Gln
            260                 265                 270

Val Gln Asn Ala Trp Asp Leu Ala Lys Ala Trp Pro Glu Ala Glu Leu
        275                 280                 285

His Ile Val Glu Gly Ala Gly His Ser Tyr Asp Glu Pro Gly Ile Leu
    290                 295                 300

His Gln Leu Met Ile Ala Thr Asp Arg Phe Ala Gly Lys
305                 310                 315

<210> SEQ ID NO 19
<211> LENGTH: 229
<212> TYPE: PRT
<213> ORGANISM: Escherichia coli

<400> SEQUENCE: 19

Met Glu Leu Leu Leu Leu Ser Asn Ser Thr Leu Pro Gly Lys Ala Trp
1               5                   10                  15

Leu Glu His Ala Leu Pro Leu Ile Ala Asn Gln Leu Asn Gly Arg Arg
            20                  25                  30

Ser Ala Val Phe Ile Pro Phe Ala Gly Val Thr Gln Thr Trp Asp Glu
        35                  40                  45

Tyr Thr Asp Lys Thr Ala Glu Val Leu Ala Pro Leu Gly Val Asn Val
    50                  55                  60

Thr Gly Ile His Arg Val Ala Asp Pro Leu Ala Ala Ile Glu Lys Ala
65                  70                  75                  80

Glu Ile Ile Ile Val Gly Gly Gly Asn Thr Phe Gln Leu Leu Lys Glu
                85                  90                  95

Ser Arg Glu Arg Gly Leu Leu Ala Pro Met Ala Asp Arg Val Lys Arg
            100                 105                 110

Gly Ala Leu Tyr Ile Gly Trp Ser Ala Gly Ala Asn Leu Ala Cys Pro
        115                 120                 125

Thr Ile Arg Thr Thr Asn Asp Met Pro Ile Val Asp Pro Asn Gly Phe
    130                 135                 140

Asp Ala Leu Asp Leu Phe Pro Leu Gln Ile Asn Pro His Phe Thr Asn
145                 150                 155                 160

Ala Leu Pro Glu Gly His Lys Gly Glu Thr Arg Glu Gln Arg Ile Arg
                165                 170                 175

Glu Leu Leu Val Val Ala Pro Glu Leu Thr Val Ile Gly Leu Pro Glu
```

-continued

```
                    180                 185                 190
Gly Asn Trp Ile Gln Val Ser Asn Gly Gln Ala Val Leu Gly Gly Pro
            195                 200                 205
Asn Thr Thr Trp Val Phe Lys Ala Gly Glu Glu Ala Val Ala Leu Glu
        210                 215                 220
Ala Gly His Arg Phe
225

<210> SEQ ID NO 20
<211> LENGTH: 99
<212> TYPE: PRT
<213> ORGANISM: Human immunodeficiency virus

<400> SEQUENCE: 20

Pro Gln Ile Thr Leu Trp Gln Arg Pro Leu Val Thr Val Lys Ile Gly
1               5                   10                  15
Gly Gln Leu Arg Glu Ala Leu Leu Asp Thr Gly Ala Asp Asp Thr Val
            20                  25                  30
Leu Glu Asp Ile Asn Leu Pro Gly Lys Trp Lys Pro Lys Met Ile Gly
        35                  40                  45
Gly Ile Gly Gly Phe Ile Lys Val Arg Gln Tyr Asp Gln Ile Leu Ile
    50                  55                  60
Glu Ile Cys Gly Lys Lys Ala Ile Gly Thr Val Leu Val Gly Pro Thr
65                  70                  75                  80
Pro Val Asn Ile Ile Gly Arg Asn Met Leu Thr Gln Ile Gly Cys Thr
                85                  90                  95
Leu Asn Phe

<210> SEQ ID NO 21
<211> LENGTH: 297
<212> TYPE: PRT
<213> ORGANISM: Escherichia coli

<400> SEQUENCE: 21

Ser Thr Glu Thr Leu Ser Phe Thr Pro Asp Asn Ile Asn Ala Asp Ile
1               5                   10                  15
Ser Leu Gly Thr Leu Ser Gly Lys Thr Lys Glu Arg Val Tyr Leu Ala
            20                  25                  30
Glu Glu Gly Gly Arg Lys Val Ser Gln Leu Asp Trp Lys Phe Asn Asn
        35                  40                  45
Ala Ala Ile Ile Lys Gly Ala Ile Asn Trp Asp Leu Met Pro Gln Ile
    50                  55                  60
Ser Ile Gly Ala Ala Gly Trp Thr Thr Leu Gly Ser Arg Gly Gly Asn
65                  70                  75                  80
Met Val Asp Gln Asp Trp Met Asp Ser Ser Asn Pro Gly Thr Trp Thr
                85                  90                  95
Asp Glu Ala Arg His Pro Asp Thr Gln Leu Asn Tyr Ala Asn Glu Phe
            100                 105                 110
Asp Leu Asn Ile Lys Gly Trp Leu Leu Asn Glu Pro Asn Tyr Arg Leu
        115                 120                 125
Gly Leu Met Ala Gly Tyr Gln Glu Ser Arg Tyr Ser Phe Thr Ala Arg
    130                 135                 140
Gly Gly Ser Tyr Ile Tyr Ser Ser Glu Glu Gly Phe Arg Asp Asp Ile
145                 150                 155                 160
Gly Ser Phe Pro Asn Gly Glu Arg Ala Ile Gly Tyr Lys Gln Arg Phe
                165                 170                 175
```

```
Lys Met Pro Tyr Ile Gly Leu Thr Gly Ser Tyr Arg Tyr Glu Asp Phe
            180                 185                 190

Glu Leu Gly Gly Thr Phe Lys Tyr Ser Gly Trp Val Glu Ser Ser Asp
            195                 200                 205

Asn Asp Glu His Tyr Asp Pro Lys Gly Arg Ile Thr Tyr Arg Ser Lys
            210                 215                 220

Val Lys Asp Gln Asn Tyr Tyr Ser Val Ala Val Asn Ala Gly Tyr Tyr
225                 230                 235                 240

Val Thr Pro Asn Ala Lys Val Tyr Val Glu Gly Ala Trp Asn Arg Val
            245                 250                 255

Thr Asn Lys Lys Gly Asn Thr Ser Leu Tyr Asp His Asn Asn Asn Thr
            260                 265                 270

Ser Asp Tyr Ser Lys Asn Gly Ala Gly Ile Glu Asn Tyr Asn Phe Ile
            275                 280                 285

Thr Thr Ala Gly Leu Lys Tyr Thr Phe
            290                 295

<210> SEQ ID NO 22
<211> LENGTH: 212
<212> TYPE: PRT
<213> ORGANISM: Carica papaya

<400> SEQUENCE: 22

Ile Pro Glu Tyr Val Asp Trp Arg Gln Lys Gly Ala Val Thr Pro Val
1               5                   10                  15

Lys Asn Gln Gly Ser Cys Gly Ser Cys Trp Ala Phe Ser Ala Val Val
            20                  25                  30

Thr Ile Glu Gly Ile Ile Lys Ile Arg Thr Gly Asn Leu Asn Gln Tyr
            35                  40                  45

Ser Glu Gln Glu Leu Leu Asp Cys Asp Arg Arg Ser Tyr Gly Cys Asn
            50                  55                  60

Gly Gly Tyr Pro Trp Ser Ala Leu Gln Leu Val Ala Gln Tyr Gly Ile
65                  70                  75                  80

His Tyr Arg Asn Thr Tyr Pro Tyr Glu Gly Val Gln Arg Tyr Cys Arg
            85                  90                  95

Ser Arg Glu Lys Gly Pro Tyr Ala Ala Lys Thr Asp Gly Val Arg Gln
            100                 105                 110

Val Gln Pro Tyr Asn Gln Gly Ala Leu Leu Tyr Ser Ile Ala Asn Gln
            115                 120                 125

Pro Val Ser Val Val Leu Gln Ala Ala Gly Lys Asp Phe Gln Leu Tyr
            130                 135                 140

Arg Gly Gly Ile Phe Val Gly Pro Cys Gly Asn Lys Val Asp His Ala
145                 150                 155                 160

Val Ala Ala Val Gly Tyr Gly Pro Asn Tyr Ile Leu Ile Lys Asn Ser
            165                 170                 175

Trp Gly Thr Gly Trp Gly Glu Asn Gly Tyr Ile Arg Ile Lys Arg Gly
            180                 185                 190

Thr Gly Asn Ser Tyr Gly Val Cys Gly Leu Tyr Thr Ser Ser Phe Tyr
            195                 200                 205

Pro Val Lys Asn
    210

<210> SEQ ID NO 23
<211> LENGTH: 699
<212> TYPE: PRT
```

<213> ORGANISM: Homo sapiens

<400> SEQUENCE: 23

```
Ala Gly Ile Ala Ala Lys Leu Ala Lys Asp Arg Glu Ala Ala Glu Gly
1               5                   10                  15

Leu Gly Ser His Glu Arg Ala Ile Lys Tyr Leu Asn Gln Asp Tyr Glu
            20                  25                  30

Ala Leu Arg Asn Glu Cys Leu Glu Ala Gly Thr Leu Phe Gln Asp Pro
        35                  40                  45

Ser Phe Pro Ala Ile Pro Ser Ala Leu Gly Phe Lys Glu Leu Gly Pro
    50                  55                  60

Tyr Ser Ser Lys Thr Arg Gly Met Arg Trp Lys Arg Pro Thr Glu Ile
65                  70                  75                  80

Cys Ala Asp Pro Gln Phe Ile Ile Gly Gly Ala Thr Arg Thr Asp Ile
                85                  90                  95

Cys Gln Gly Ala Leu Gly Asp Cys Trp Leu Leu Ala Ala Ile Ala Ser
            100                 105                 110

Leu Thr Leu Asn Glu Glu Ile Leu Ala Arg Val Val Pro Leu Asn Gln
        115                 120                 125

Ser Phe Gln Glu Asn Tyr Ala Gly Ile Phe His Phe Gln Phe Trp Gln
    130                 135                 140

Tyr Gly Glu Trp Val Glu Val Val Asp Asp Arg Leu Pro Thr Lys
145                 150                 155                 160

Asp Gly Glu Leu Leu Phe Val His Ser Ala Glu Gly Ser Glu Phe Trp
                165                 170                 175

Ser Ala Leu Leu Glu Lys Ala Tyr Ala Lys Ile Asn Gly Cys Tyr Glu
            180                 185                 190

Ala Leu Ser Gly Gly Ala Thr Thr Glu Gly Phe Glu Asp Phe Thr Gly
        195                 200                 205

Gly Ile Ala Glu Trp Tyr Glu Leu Lys Lys Pro Pro Pro Asn Leu Phe
    210                 215                 220

Lys Ile Ile Gln Lys Ala Leu Gln Lys Gly Ser Leu Leu Gly Cys Ser
225                 230                 235                 240

Ile Asp Ile Thr Ser Ala Ala Asp Ser Glu Ala Ile Thr Phe Gln Lys
                245                 250                 255

Leu Val Lys Gly His Ala Tyr Ser Val Thr Gly Ala Glu Glu Val Glu
            260                 265                 270

Ser Asn Gly Ser Leu Gln Lys Leu Ile Arg Ile Arg Asn Pro Trp Gly
        275                 280                 285

Glu Val Glu Trp Thr Gly Arg Trp Asn Asp Asn Cys Pro Ser Trp Asn
    290                 295                 300

Thr Ile Asp Pro Glu Glu Arg Glu Arg Leu Thr Arg Arg His Glu Asp
305                 310                 315                 320

Gly Glu Phe Trp Met Ser Phe Ser Asp Phe Leu Arg His Tyr Ser Arg
                325                 330                 335

Leu Glu Ile Cys Asn Leu Thr Pro Asp Thr Leu Thr Ser Asp Thr Tyr
            340                 345                 350

Lys Lys Trp Lys Leu Thr Lys Met Asp Gly Asn Trp Arg Arg Gly Ser
        355                 360                 365

Thr Ala Gly Gly Cys Arg Asn Tyr Pro Asn Thr Phe Trp Met Asn Pro
    370                 375                 380

Gln Tyr Leu Ile Lys Leu Glu Glu Glu Asp Glu Asp Glu Glu Asp Gly
385                 390                 395                 400
```

Glu Ser Gly Cys Thr Phe Leu Val Gly Leu Ile Gln Lys His Arg Arg
                    405                 410                 415

Arg Gln Arg Lys Met Gly Glu Asp Met His Thr Ile Gly Phe Gly Ile
                420                 425                 430

Tyr Glu Val Pro Glu Glu Leu Ser Gly Gln Thr Asn Ile His Leu Ser
            435                 440                 445

Lys Asn Phe Phe Leu Thr Asn Arg Ala Arg Glu Arg Ser Asp Thr Phe
        450                 455                 460

Ile Asn Leu Arg Glu Val Leu Asn Arg Phe Lys Leu Pro Pro Gly Glu
465                 470                 475                 480

Tyr Ile Leu Val Pro Ser Thr Phe Glu Pro Asn Lys Asp Gly Asp Phe
                485                 490                 495

Cys Ile Arg Val Phe Ser Glu Lys Lys Ala Asp Tyr Gln Ala Val Asp
                500                 505                 510

Asp Glu Ile Glu Ala Asn Leu Glu Glu Phe Asp Ile Ser Glu Asp Asp
                515                 520                 525

Ile Asp Asp Gly Val Arg Arg Leu Phe Ala Gln Leu Ala Gly Glu Asp
            530                 535                 540

Ala Glu Ile Ser Ala Phe Glu Leu Gln Thr Ile Leu Arg Arg Val Leu
545                 550                 555                 560

Ala Lys Arg Gln Asp Ile Lys Ser Asp Gly Phe Ser Ile Glu Thr Cys
                565                 570                 575

Lys Ile Met Val Asp Met Leu Asp Ser Asp Gly Ser Gly Lys Leu Gly
                580                 585                 590

Leu Lys Glu Phe Tyr Ile Leu Trp Thr Lys Ile Gln Lys Tyr Gln Lys
            595                 600                 605

Ile Tyr Arg Glu Ile Asp Val Asp Arg Ser Gly Thr Met Asn Ser Tyr
        610                 615                 620

Glu Met Arg Lys Ala Leu Glu Glu Ala Gly Phe Lys Met Pro Cys Gln
625                 630                 635                 640

Leu His Gln Val Ile Val Ala Arg Phe Ala Asp Asp Gln Leu Ile Ile
                645                 650                 655

Asp Phe Asp Asn Phe Val Arg Cys Leu Val Arg Leu Glu Thr Leu Phe
                660                 665                 670

Lys Ile Phe Lys Gln Leu Asp Pro Glu Asn Thr Gly Thr Ile Glu Leu
            675                 680                 685

Asp Leu Ile Ser Trp Leu Cys Phe Ser Val Leu
    690                 695

<210> SEQ ID NO 24
<211> LENGTH: 221
<212> TYPE: PRT
<213> ORGANISM: Tobacco etch virus

<400> SEQUENCE: 24

Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

-continued

Asp Met Ile Ile Ile Arg Met Pro Lys Asp Phe Pro Phe Pro Gln
                85                  90                  95

Lys Leu Lys Phe Arg Glu Pro Gln Arg Glu Arg Ile Cys Leu Val
            100                 105                 110

Thr Thr Asn Phe Gln Thr Lys Ser Met Ser Ser Met Val Ser Asp Thr
            115                 120                 125

Ser Cys Thr Phe Pro Ser Ser Asp Gly Ile Phe Trp Lys His Trp Ile
    130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Asp Lys Pro
    210                 215                 220

<210> SEQ ID NO 25
<211> LENGTH: 371
<212> TYPE: PRT
<213> ORGANISM: Streptococcus pyogenes

<400> SEQUENCE: 25

Asp Gln Asn Phe Ala Arg Asn Glu Lys Glu Ala Lys Asp Ser Ala Ile
1               5                   10                  15

Thr Phe Ile Gln Lys Ser Ala Ala Ile Lys Ala Gly Ala Arg Ser Ala
            20                  25                  30

Glu Asp Ile Lys Leu Asp Lys Val Asn Leu Gly Gly Glu Leu Ser Gly
        35                  40                  45

Ser Asn Met Tyr Val Tyr Asn Ile Ser Thr Gly Gly Phe Val Ile Val
    50                  55                  60

Ser Gly Asp Lys Arg Ser Pro Glu Ile Leu Gly Tyr Ser Thr Ser Gly
65                  70                  75                  80

Ser Phe Asp Val Asn Gly Lys Glu Asn Ile Ala Ser Phe Met Glu Ser
                85                  90                  95

Tyr Val Glu Gln Ile Lys Glu Asn Lys Lys Leu Asp Ser Thr Tyr Ala
            100                 105                 110

Gly Thr Ala Glu Ile Lys Gln Pro Val Val Lys Ser Leu Leu Asp Ser
        115                 120                 125

Lys Gly Ile His Tyr Asn Gln Gly Asn Pro Tyr Asn Leu Leu Thr Pro
    130                 135                 140

Val Ile Glu Lys Val Lys Pro Gly Glu Gln Ser Phe Val Gly Gln His
145                 150                 155                 160

Ala Ala Thr Gly Ser Val Ala Thr Ala Gln Ile Met Lys Tyr
                165                 170                 175

His Asn Tyr Pro Asn Lys Gly Leu Lys Asp Tyr Thr Tyr Thr Leu Ser
            180                 185                 190

Ser Asn Asn Pro Tyr Phe Asn His Pro Lys Asn Leu Phe Ala Ala Ile
        195                 200                 205

Ser Thr Arg Gln Tyr Asn Trp Asn Asn Ile Leu Pro Thr Tyr Ser Gly
    210                 215                 220

Arg Glu Ser Asn Val Gln Lys Met Ala Ile Ser Glu Leu Met Ala Asp

-continued

```
                225                 230                 235                 240
Val Gly Ile Ser Val Asp Met Asp Tyr Gly Pro Ser Ser Gly Ser Ala
                245                 250                 255

Gly Ser Ser Arg Val Gln Arg Ala Leu Lys Glu Asn Phe Gly Tyr Asn
                260                 265                 270

Gln Ser Val His Gln Ile Asn Arg Gly Asp Phe Ser Lys Gln Asp Trp
                275                 280                 285

Glu Ala Gln Ile Asp Lys Glu Leu Ser Gln Asn Gln Pro Val Tyr Tyr
                290                 295                 300

Gln Gly Val Gly Lys Val Gly His Ala Phe Val Ile Asp Gly Ala
305                 310                 315                 320

Asp Gly Arg Asn Phe Tyr His Val Asn Trp Gly Trp Gly Gly Val Ser
                325                 330                 335

Asp Gly Phe Phe Arg Leu Asp Ala Leu Asn Pro Ser Ala Leu Gly Thr
                340                 345                 350

Gly Gly Gly Ala Gly Gly Phe Asn Gly Tyr Gln Ser Ala Val Val Gly
                355                 360                 365

Ile Lys Pro
    370

<210> SEQ ID NO 26
<211> LENGTH: 353
<212> TYPE: PRT
<213> ORGANISM: Homo sapiens

<400> SEQUENCE: 26

Lys Lys His Thr Gly Tyr Val Gly Leu Lys Asn Gln Gly Ala Thr Cys
1               5                   10                  15

Tyr Met Asn Ser Leu Leu Gln Thr Leu Phe Phe Thr Asn Gln Leu Arg
                20                  25                  30

Lys Ala Val Tyr Met Met Pro Thr Glu Gly Asp Asp Ser Ser Lys Ser
                35                  40                  45

Val Pro Leu Ala Leu Gln Arg Val Phe Tyr Glu Leu Gln His Ser Asp
                50                  55                  60

Lys Pro Val Gly Thr Lys Lys Leu Thr Lys Ser Phe Gly Trp Glu Thr
65                  70                  75                  80

Leu Asp Ser Phe Met Gln His Asp Val Gln Glu Leu Cys Arg Val Leu
                85                  90                  95

Leu Asp Asn Val Glu Asn Lys Met Lys Gly Thr Cys Val Glu Gly Thr
                100                 105                 110

Ile Pro Lys Leu Phe Arg Gly Lys Met Val Ser Tyr Ile Gln Cys Lys
                115                 120                 125

Glu Val Asp Tyr Arg Ser Asp Arg Arg Glu Asp Tyr Tyr Asp Ile Gln
                130                 135                 140

Leu Ser Ile Lys Gly Lys Lys Asn Ile Phe Glu Ser Phe Val Asp Tyr
145                 150                 155                 160

Val Ala Val Glu Gln Leu Asp Gly Asp Asn Lys Tyr Asp Ala Gly Glu
                165                 170                 175

His Gly Leu Gln Glu Ala Glu Lys Gly Val Lys Phe Leu Thr Leu Pro
                180                 185                 190

Pro Val Leu His Leu Gln Leu Met Arg Phe Met Tyr Asp Pro Gln Thr
                195                 200                 205

Asp Gln Asn Ile Lys Ile Asn Asp Arg Phe Glu Phe Pro Glu Gln Leu
                210                 215                 220
```

```
Pro Leu Asp Glu Phe Leu Gln Lys Thr Asp Pro Lys Asp Pro Ala Asn
225                 230                 235                 240

Tyr Ile Leu His Ala Val Leu Val His Ser Gly Asp Asn His Gly Gly
            245                 250                 255

His Tyr Val Val Tyr Leu Asn Pro Lys Gly Asp Gly Lys Trp Cys Lys
        260                 265                 270

Phe Asp Asp Val Val Ser Arg Cys Thr Lys Glu Glu Ala Ile Glu
        275                 280                 285

His Asn Tyr Gly Gly His Asp Asp Leu Ser Val Arg His Cys Thr
    290                 295                 300

Asn Ala Tyr Met Leu Val Tyr Ile Arg Glu Ser Lys Leu Ser Glu Val
305                 310                 315                 320

Leu Gln Ala Val Thr Asp His Asp Ile Pro Gln Gln Leu Val Glu Arg
                325                 330                 335

Leu Gln Glu Glu Lys Arg Ile Glu Ala Gln Lys Arg Lys Glu Arg Gln
                340                 345                 350

Glu

<210> SEQ ID NO 27
<211> LENGTH: 174
<212> TYPE: PRT
<213> ORGANISM: Staphylococcus aureus

<400> SEQUENCE: 27

Tyr Asn Glu Gln Tyr Val Asn Lys Leu Glu Asn Phe Lys Ile Arg Glu
1               5                   10                  15

Thr Gln Gly Asn Asn Gly Trp Cys Ala Gly Tyr Thr Met Ser Ala Leu
                20                  25                  30

Leu Asn Ala Thr Tyr Asn Thr Asn Lys Tyr His Ala Glu Ala Val Met
            35                  40                  45

Arg Phe Leu His Pro Asn Leu Gln Gly Gln Gln Phe Gln Phe Thr Gly
        50                  55                  60

Leu Thr Pro Arg Glu Met Ile Tyr Phe Gly Gln Thr Gln Gly Arg Ser
65                  70                  75                  80

Pro Gln Leu Leu Asn Arg Met Thr Thr Tyr Asn Glu Val Asp Asn Leu
                85                  90                  95

Thr Lys Asn Asn Lys Gly Ile Ala Ile Leu Gly Ser Arg Val Glu Ser
                100                 105                 110

Arg Asn Gly Met His Ala Gly His Ala Met Ala Val Val Gly Asn Ala
            115                 120                 125

Lys Leu Asn Asn Gly Gln Glu Val Ile Ile Trp Asn Pro Trp Asp
    130                 135                 140

Asn Gly Phe Met Thr Gln Asp Ala Lys Asn Asn Val Ile Pro Val Ser
145                 150                 155                 160

Asn Gly Asp His Tyr Gln Trp Tyr Ser Ser Ile Tyr Gly Tyr
                165                 170

<210> SEQ ID NO 28
<211> LENGTH: 221
<212> TYPE: PRT
<213> ORGANISM: Saccharomyces cerevisiae

<400> SEQUENCE: 28

Gly Ser Leu Val Pro Glu Leu Asn Glu Lys Asp Asp Gln Val Gln
1               5                   10                  15

Lys Ala Leu Ala Ser Arg Glu Asn Thr Gln Leu Met Asn Arg Asp Asn
```

-continued

```
                    20                  25                  30
Ile Glu Ile Thr Val Arg Asp Phe Lys Thr Leu Ala Pro Arg Arg Trp
            35                  40                  45

Leu Asn Asp Thr Ile Ile Glu Phe Phe Met Lys Tyr Ile Glu Lys Ser
        50                  55                  60

Thr Pro Asn Thr Val Ala Phe Asn Ser Phe Phe Tyr Thr Asn Leu Ser
65                  70                  75                  80

Glu Arg Gly Tyr Gln Gly Val Arg Arg Trp Met Lys Arg Lys Lys Thr
                85                  90                  95

Gln Ile Asp Lys Leu Asp Lys Ile Phe Thr Pro Ile Asn Leu Asn Gln
            100                 105                 110

Ser His Trp Ala Leu Gly Ile Ile Asp Leu Lys Lys Lys Thr Ile Gly
        115                 120                 125

Tyr Val Asp Ser Leu Ser Asn Gly Pro Asn Ala Met Ser Phe Ala Ile
    130                 135                 140

Leu Thr Asp Leu Gln Lys Tyr Val Met Glu Glu Ser Lys His Thr Ile
145                 150                 155                 160

Gly Glu Asp Phe Asp Leu Ile His Leu Asp Cys Pro Gln Gln Pro Asn
                165                 170                 175

Gly Tyr Asp Cys Gly Ile Tyr Val Cys Met Asn Thr Leu Tyr Gly Ser
            180                 185                 190

Ala Asp Ala Pro Leu Asp Phe Asp Tyr Lys Asp Ala Ile Arg Met Arg
        195                 200                 205

Arg Phe Ile Ala His Leu Ile Leu Thr Asp Ala Leu Lys
    210                 215                 220

<210> SEQ ID NO 29
<211> LENGTH: 166
<212> TYPE: PRT
<213> ORGANISM: Pyrococcus horikoshii

<400> SEQUENCE: 29

Met Lys Val Leu Phe Leu Thr Ala Asn Glu Phe Glu Asp Val Glu Leu
1               5                   10                  15

Ile Tyr Pro Tyr His Arg Leu Lys Glu Glu Gly His Glu Val Tyr Ile
            20                  25                  30

Ala Ser Phe Glu Arg Gly Thr Ile Thr Gly Lys His Gly Tyr Ser Val
        35                  40                  45

Lys Val Asp Leu Thr Phe Asp Lys Val Asn Pro Glu Glu Phe Asp Ala
    50                  55                  60

Leu Val Leu Pro Gly Gly Arg Ala Pro Glu Arg Val Arg Leu Asn Glu
65                  70                  75                  80

Lys Ala Val Ser Ile Ala Arg Lys Met Phe Ser Glu Gly Lys Pro Val
                85                  90                  95

Ala Ser Ile Cys His Gly Pro Gln Ile Leu Ile Ser Ala Gly Val Leu
            100                 105                 110

Arg Gly Arg Lys Gly Thr Ser Tyr Pro Gly Ile Lys Asp Asp Met Ile
        115                 120                 125

Asn Ala Gly Val Glu Trp Val Asp Ala Glu Val Val Asp Gly Asn
    130                 135                 140

Trp Val Ser Ser Arg Val Pro Ala Asp Leu Tyr Ala Trp Met Arg Glu
145                 150                 155                 160

Phe Val Lys Leu Leu Lys
                165
```

<210> SEQ ID NO 30
<211> LENGTH: 316
<212> TYPE: PRT
<213> ORGANISM: Bacillus thermoproteolyticus

<400> SEQUENCE: 30

```
Ile Thr Gly Thr Ser Thr Val Gly Val Gly Arg Gly Val Leu Gly Asp
1               5                   10                  15

Gln Lys Asn Ile Asn Thr Thr Tyr Ser Thr Tyr Tyr Tyr Leu Gln Asp
            20                  25                  30

Asn Thr Arg Gly Asp Gly Ile Phe Thr Tyr Asp Ala Lys Tyr Arg Thr
        35                  40                  45

Thr Leu Pro Gly Ser Leu Trp Ala Asp Ala Asp Asn Gln Phe Phe Ala
    50                  55                  60

Ser Tyr Asp Ala Pro Ala Val Asp Ala His Tyr Tyr Ala Gly Val Thr
65                  70                  75                  80

Tyr Asp Tyr Tyr Lys Asn Val His Asn Arg Leu Ser Tyr Asp Gly Asn
                85                  90                  95

Asn Ala Ala Ile Arg Ser Ser Val His Tyr Ser Gln Gly Tyr Asn Asn
            100                 105                 110

Ala Phe Trp Asn Gly Ser Glu Met Val Tyr Gly Asp Gly Asp Gly Gln
        115                 120                 125

Thr Phe Ile Pro Leu Ser Gly Gly Ile Asp Val Val Ala His Glu Leu
    130                 135                 140

Thr His Ala Val Thr Asp Tyr Thr Ala Gly Leu Ile Tyr Gln Asn Glu
145                 150                 155                 160

Ser Gly Ala Ile Asn Glu Ala Ile Ser Asp Ile Phe Gly Thr Leu Val
                165                 170                 175

Glu Phe Tyr Ala Asn Lys Asn Pro Asp Trp Glu Ile Gly Glu Asp Val
            180                 185                 190

Tyr Thr Pro Gly Ile Ser Gly Asp Ser Leu Arg Ser Met Ser Asp Pro
        195                 200                 205

Ala Lys Tyr Gly Asp Pro Asp His Tyr Ser Lys Arg Tyr Thr Gly Thr
    210                 215                 220

Gln Asp Asn Gly Gly Val His Ile Asn Ser Gly Ile Ile Asn Lys Ala
225                 230                 235                 240

Ala Tyr Leu Ile Ser Gln Gly Gly Thr His Tyr Gly Val Ser Val Val
                245                 250                 255

Gly Ile Gly Arg Asp Lys Leu Gly Lys Ile Phe Tyr Arg Ala Leu Thr
            260                 265                 270

Gln Tyr Leu Thr Pro Thr Ser Asn Phe Ser Gln Leu Arg Ala Ala Ala
        275                 280                 285

Val Gln Ser Ala Thr Asp Leu Tyr Gly Ser Thr Ser Gln Glu Val Ala
    290                 295                 300

Ser Val Lys Gln Ala Phe Asp Ala Val Gly Val Lys
305                 310                 315
```

<210> SEQ ID NO 31
<211> LENGTH: 169
<212> TYPE: PRT
<213> ORGANISM: Homo sapiens

<400> SEQUENCE: 31

```
Val Leu Thr Glu Gly Asn Pro Arg Trp Glu Gln Thr His Leu Thr Tyr
1               5                   10                  15
```

-continued

```
Arg Ile Glu Asn Tyr Thr Pro Asp Leu Pro Arg Ala Asp Val Asp His
             20                  25                  30

Ala Ile Glu Lys Ala Phe Gln Leu Trp Ser Asn Val Thr Pro Leu Thr
         35                  40                  45

Phe Thr Lys Val Ser Glu Gly Gln Ala Asp Ile Met Ile Ser Phe Val
     50                  55                  60

Arg Gly Asp His Arg Asp Asn Ser Pro Phe Asp Gly Pro Gly Gly Asn
 65                  70                  75                  80

Leu Ala His Ala Phe Gln Pro Gly Pro Gly Ile Gly Gly Asp Ala His
                 85                  90                  95

Phe Asp Glu Asp Glu Arg Trp Thr Asn Asn Phe Arg Glu Tyr Asn Leu
            100                 105                 110

His Arg Val Ala Ala His Glu Leu Gly His Ser Leu Gly Leu Ser His
        115                 120                 125

Ser Thr Asp Ile Gly Ala Leu Met Tyr Pro Ser Tyr Thr Phe Ser Gly
    130                 135                 140

Asp Val Gln Leu Ala Gln Asp Asp Ile Asp Gly Ile Gln Ala Ile Tyr
145                 150                 155                 160

Gly Arg Ser Gln Asn Pro Val Gln Pro
                165

<210> SEQ ID NO 32
<211> LENGTH: 496
<212> TYPE: PRT
<213> ORGANISM: Homo sapiens

<400> SEQUENCE: 32

Gln Tyr Ser Pro Asn Thr Gln Gln Gly Arg Thr Ser Ile Val His Leu
 1               5                  10                  15

Phe Glu Trp Arg Trp Val Asp Ile Ala Leu Glu Cys Glu Arg Tyr Leu
             20                  25                  30

Ala Pro Lys Gly Phe Gly Gly Val Gln Val Ser Pro Pro Asn Glu Asn
         35                  40                  45

Val Ala Ile Tyr Asn Pro Phe Arg Pro Trp Trp Glu Arg Tyr Gln Pro
     50                  55                  60

Val Ser Tyr Lys Leu Cys Thr Arg Ser Gly Asn Glu Asp Glu Phe Arg
 65                  70                  75                  80

Asn Met Val Thr Arg Cys Asn Asn Val Gly Val Arg Ile Tyr Val Asp
                 85                  90                  95

Ala Val Ile Asn His Met Cys Gly Asn Ala Val Ser Ala Gly Thr Ser
            100                 105                 110

Ser Thr Cys Gly Ser Tyr Phe Asn Pro Gly Ser Arg Asp Phe Pro Ala
        115                 120                 125

Val Pro Tyr Ser Gly Trp Asp Phe Asn Asp Gly Lys Cys Lys Thr Gly
    130                 135                 140

Ser Gly Asp Ile Glu Asn Tyr Asn Asp Ala Thr Gln Val Arg Asp Cys
145                 150                 155                 160

Arg Leu Thr Gly Leu Leu Asp Leu Ala Leu Glu Lys Asp Tyr Val Arg
                165                 170                 175

Ser Lys Ile Ala Glu Tyr Met Asn His Leu Ile Asp Ile Gly Val Ala
            180                 185                 190

Gly Phe Arg Leu Asp Ala Ser Lys His Met Trp Pro Gly Asp Ile Lys
        195                 200                 205

Ala Ile Leu Asp Lys Leu His Asn Leu Asn Ser Asn Trp Phe Pro Ala
    210                 215                 220
```

Gly Ser Lys Pro Phe Ile Tyr Gln Glu Val Ile Asp Leu Gly Glu
225                 230                 235                 240

Pro Ile Lys Ser Ser Asp Tyr Phe Gly Asn Gly Arg Val Thr Glu Phe
                245                 250                 255

Lys Tyr Gly Ala Lys Leu Gly Thr Val Ile Arg Lys Trp Asn Gly Glu
            260                 265                 270

Lys Met Ser Tyr Leu Lys Asn Trp Gly Glu Gly Trp Gly Phe Val Pro
        275                 280                 285

Ser Asp Arg Ala Leu Val Phe Val Asp Asn His Asp Asn Gln Arg Gly
    290                 295                 300

His Gly Ala Gly Gly Ala Ser Ile Leu Thr Phe Trp Asp Ala Arg Leu
305                 310                 315                 320

Tyr Lys Met Ala Val Gly Phe Met Leu Ala His Pro Tyr Gly Phe Thr
                325                 330                 335

Arg Val Met Ser Ser Tyr Arg Trp Pro Arg Gln Phe Gln Asn Gly Asn
                340                 345                 350

Asp Val Asn Asp Trp Val Gly Pro Pro Asn Asn Asn Gly Val Ile Lys
            355                 360                 365

Glu Val Thr Ile Asn Pro Asp Thr Thr Cys Gly Asn Asp Trp Val Cys
370                 375                 380

Glu His Arg Trp Arg Gln Ile Arg Asn Met Val Ile Phe Arg Asn Val
385                 390                 395                 400

Val Asp Gly Gln Pro Phe Thr Asn Trp Tyr Asp Asn Gly Ser Asn Gln
                405                 410                 415

Val Ala Phe Gly Arg Gly Asn Arg Gly Phe Ile Val Phe Asn Asn Asp
                420                 425                 430

Asp Trp Ser Phe Ser Leu Thr Leu Gln Thr Gly Leu Pro Ala Gly Thr
            435                 440                 445

Tyr Cys Asp Val Ile Ser Gly Asp Lys Ile Asn Gly Asn Cys Thr Gly
            450                 455                 460

Ile Lys Ile Tyr Val Ser Asp Asp Gly Lys Ala His Phe Ser Ile Ser
465                 470                 475                 480

Asn Ser Ala Glu Asp Pro Phe Ile Ala Ile His Ala Glu Ser Lys Leu
                485                 490                 495

<210> SEQ ID NO 33
<211> LENGTH: 370
<212> TYPE: PRT
<213> ORGANISM: Trichoderma reesei

<400> SEQUENCE: 33

Gln Pro Gly Thr Ser Thr Pro Glu Val His Pro Lys Leu Thr Thr Tyr
1               5                   10                  15

Lys Cys Thr Lys Ser Gly Gly Cys Val Ala Gln Asp Thr Ser Val Val
            20                  25                  30

Leu Asp Trp Asn Tyr Arg Trp Met His Asp Ala Asn Tyr Asn Ser Cys
        35                  40                  45

Thr Val Asn Gly Gly Val Asn Thr Thr Leu Cys Pro Asp Glu Ala Thr
    50                  55                  60

Cys Gly Lys Asn Cys Phe Ile Glu Gly Val Asp Tyr Ala Ala Ser Gly
65                  70                  75                  80

Val Thr Thr Ser Gly Ser Ser Leu Thr Met Asn Gln Tyr Met Pro Ser
                85                  90                  95

Ser Ser Gly Gly Tyr Ser Ser Val Ser Pro Arg Leu Tyr Leu Leu Asp

```
                    100                 105                 110
Ser Asp Gly Glu Tyr Val Met Leu Lys Leu Asn Gly Gln Glu Leu Ser
            115                 120                 125

Phe Asp Val Asp Leu Ser Ala Leu Pro Cys Gly Glu Asn Gly Ser Leu
130                 135                 140

Tyr Leu Ser Gln Met Asp Glu Asn Gly Gly Ala Asn Gln Tyr Asn Thr
145                 150                 155                 160

Ala Gly Ala Asn Tyr Gly Ser Gly Tyr Cys Asp Ala Gln Cys Pro Val
            165                 170                 175

Gln Thr Trp Arg Asn Gly Thr Leu Asn Thr Ser His Gln Gly Phe Cys
            180                 185                 190

Cys Asn Glu Met Asp Ile Leu Glu Gly Asn Ser Arg Ala Asn Ala Leu
            195                 200                 205

Thr Pro His Ser Cys Thr Ala Thr Ala Cys Asp Ser Ala Gly Cys Gly
            210                 215                 220

Phe Asn Pro Tyr Gly Ser Gly Tyr Lys Ser Tyr Tyr Gly Pro Gly Asp
225                 230                 235                 240

Thr Val Asp Thr Ser Lys Thr Phe Thr Ile Ile Thr Gln Phe Asn Thr
            245                 250                 255

Asp Asn Gly Ser Pro Ser Gly Asn Leu Val Ser Ile Thr Arg Lys Tyr
            260                 265                 270

Gln Gln Asn Gly Val Asp Ile Pro Ser Ala Gln Pro Gly Gly Asp Thr
            275                 280                 285

Ile Ser Ser Cys Pro Ser Ala Ser Ala Tyr Gly Gly Leu Ala Thr Met
            290                 295                 300

Gly Lys Ala Leu Ser Ser Gly Met Val Leu Val Phe Ser Ile Trp Asn
305                 310                 315                 320

Asp Asn Ser Gln Tyr Met Asn Trp Leu Asp Ser Gly Asn Ala Gly Pro
            325                 330                 335

Cys Ser Ser Thr Glu Gly Asn Pro Ser Asn Ile Leu Ala Asn Asn Pro
            340                 345                 350

Asn Thr His Val Val Phe Ser Asn Ile Arg Trp Gly Asp Ile Gly Ser
            355                 360                 365

Thr Thr
   370

<210> SEQ ID NO 34
<211> LENGTH: 223
<212> TYPE: PRT
<213> ORGANISM: Aspergillus niger

<400> SEQUENCE: 34

Gln Thr Met Cys Ser Gln Tyr Asp Ser Ala Ser Ser Pro Pro Tyr Ser
1               5                   10                  15

Val Asn Gln Asn Leu Trp Gly Glu Tyr Gln Gly Thr Gly Ser Gln Cys
            20                  25                  30

Val Tyr Val Asp Lys Leu Ser Ser Gly Ala Ser Trp His Thr Glu
            35                  40                  45

Trp Thr Trp Ser Gly Gly Glu Gly Thr Val Lys Ser Tyr Ser Asn Ser
        50                  55                  60

Gly Val Thr Phe Asn Lys Lys Leu Val Ser Asp Val Ser Ser Ile Pro
65                  70                  75                  80

Thr Ser Val Glu Trp Lys Gln Asp Asn Thr Asn Val Asn Ala Asp Val
                85                  90                  95
```

Ala Tyr Asp Leu Phe Thr Ala Ala Asn Val Asp His Ala Thr Ser Ser
            100                 105                 110

Gly Asp Tyr Glu Leu Met Ile Trp Leu Ala Arg Tyr Gly Asn Ile Gln
        115                 120                 125

Pro Ile Gly Lys Gln Ile Ala Thr Ala Thr Val Gly Gly Lys Ser Trp
    130                 135                 140

Glu Val Trp Tyr Gly Ser Thr Thr Gln Ala Gly Ala Glu Gln Arg Thr
145                 150                 155                 160

Tyr Ser Phe Val Ser Glu Ser Pro Ile Asn Ser Tyr Ser Gly Asp Ile
                165                 170                 175

Asn Ala Phe Phe Ser Tyr Leu Thr Gln Asn Gln Gly Phe Pro Ala Ser
            180                 185                 190

Ser Gln Tyr Leu Ile Asn Leu Gln Phe Gly Thr Glu Ala Phe Thr Gly
        195                 200                 205

Gly Pro Ala Thr Phe Thr Val Asp Asn Trp Thr Ala Ser Val Asn
    210                 215                 220

<210> SEQ ID NO 35
<211> LENGTH: 184
<212> TYPE: PRT
<213> ORGANISM: Aspergillus niger

<400> SEQUENCE: 35

Ser Ala Gly Ile Asn Tyr Val Gln Asn Tyr Asn Gly Asn Leu Gly Asp
1               5                   10                  15

Phe Thr Tyr Asp Glu Ser Ala Gly Thr Phe Ser Met Tyr Trp Glu Asp
            20                  25                  30

Gly Val Ser Ser Asp Phe Val Val Gly Leu Gly Trp Thr Thr Gly Ser
        35                  40                  45

Ser Asn Ala Ile Thr Tyr Ser Ala Glu Tyr Ser Ala Ser Gly Ser Ala
    50                  55                  60

Ser Tyr Leu Ala Val Tyr Gly Trp Val Asn Tyr Pro Gln Ala Glu Tyr
65                  70                  75                  80

Tyr Ile Val Glu Asp Tyr Gly Asp Tyr Asn Pro Cys Ser Ser Ala Thr
                85                  90                  95

Ser Leu Gly Thr Val Tyr Ser Asp Gly Ser Thr Tyr Gln Val Cys Thr
            100                 105                 110

Asp Thr Arg Thr Asn Glu Pro Ser Ile Thr Gly Thr Ser Thr Phe Thr
        115                 120                 125

Gln Tyr Phe Ser Val Arg Glu Ser Thr Arg Thr Ser Gly Thr Val Thr
    130                 135                 140

Val Ala Asn His Phe Asn Phe Trp Ala His His Gly Phe Gly Asn Ser
145                 150                 155                 160

Asp Phe Asn Tyr Gln Val Val Ala Val Glu Ala Trp Ser Gly Ala Gly
                165                 170                 175

Ser Ala Ser Val Thr Ile Ser Ser
            180

<210> SEQ ID NO 36
<211> LENGTH: 313
<212> TYPE: PRT
<213> ORGANISM: Streptomyces lividans

<400> SEQUENCE: 36

Ala Glu Ser Thr Leu Gly Ala Ala Ala Gln Ser Gly Arg Tyr Phe
1               5                   10                  15

```
Gly Thr Ala Ile Ala Ser Gly Arg Leu Ser Asp Ser Thr Tyr Thr Ser
            20                  25                  30

Ile Ala Gly Arg Glu Phe Asn Met Val Thr Ala Glu Asn Glu Met Lys
            35                  40                  45

Ile Asp Ala Thr Glu Pro Gln Arg Gly Gln Phe Asn Phe Ser Ser Ala
50                  55                  60

Asp Arg Val Tyr Asn Trp Ala Val Gln Asn Gly Lys Gln Val Arg Gly
65                  70                  75                  80

His Thr Leu Ala Trp His Ser Gln Pro Gly Trp Met Gln Ser Leu
                85                  90                  95

Ser Gly Ser Ala Leu Arg Gln Ala Met Ile Asp His Ile Asn Gly Val
            100                 105                 110

Met Ala His Tyr Lys Gly Lys Ile Val Gln Trp Asp Val Val Asn Glu
            115                 120                 125

Ala Phe Ala Asp Gly Ser Ser Gly Ala Arg Arg Asp Ser Asn Leu Gln
130                 135                 140

Arg Ser Gly Asn Asp Trp Ile Glu Val Ala Phe Arg Thr Ala Arg Ala
145                 150                 155                 160

Ala Asp Pro Ser Ala Lys Leu Cys Tyr Asn Asp Tyr Asn Val Glu Asn
            165                 170                 175

Trp Thr Trp Ala Lys Thr Gln Ala Met Tyr Asn Met Val Arg Asp Phe
            180                 185                 190

Lys Gln Arg Gly Val Pro Ile Asp Cys Val Gly Phe Gln Ser His Phe
            195                 200                 205

Asn Ser Gly Ser Pro Tyr Asn Ser Asn Phe Arg Thr Thr Leu Gln Asn
            210                 215                 220

Phe Ala Ala Leu Gly Val Asp Val Ala Ile Thr Glu Leu Asp Ile Gln
225                 230                 235                 240

Gly Ala Pro Ala Ser Thr Tyr Ala Asn Val Thr Asn Asp Cys Leu Ala
            245                 250                 255

Val Ser Arg Cys Leu Gly Ile Thr Val Trp Gly Val Arg Asp Ser Asp
            260                 265                 270

Ser Trp Arg Ser Glu Gln Thr Pro Leu Leu Phe Asn Asn Asp Gly Ser
            275                 280                 285

Lys Lys Ala Ala Tyr Thr Ala Val Leu Asp Ala Leu Asn Gly Gly Ala
            290                 295                 300

Ser Ser Glu Pro Pro Ala Asp Gly Gly
305                 310

<210> SEQ ID NO 37
<211> LENGTH: 362
<212> TYPE: PRT
<213> ORGANISM: Aspergillus niger

<400> SEQUENCE: 37

Met His Ser Phe Ala Ser Leu Leu Ala Tyr Gly Leu Val Ala Gly Ala
1               5                   10                  15

Thr Phe Ala Ser Ala Ser Pro Ile Glu Ala Arg Asp Ser Cys Thr Phe
            20                  25                  30

Thr Thr Ala Ala Ala Lys Ala Gly Lys Ala Lys Cys Ser Thr Ile
            35                  40                  45

Thr Leu Asn Asn Ile Glu Val Pro Ala Gly Thr Thr Leu Asp Leu Thr
            50                  55                  60

Gly Leu Thr Ser Gly Thr Lys Val Ile Phe Glu Gly Thr Thr Thr Phe
65                  70                  75                  80
```

Gln Tyr Glu Glu Trp Ala Gly Pro Leu Ile Ser Met Ser Gly Glu His
                85                  90                  95

Ile Thr Val Thr Gly Ala Ser Gly His Leu Ile Asn Cys Asp Gly Ala
            100                 105                 110

Arg Trp Trp Asp Gly Lys Gly Thr Gly Lys Lys Pro Lys Phe
        115                 120                 125

Phe Tyr Ala His Gly Leu Asp Ser Ser Ile Thr Gly Leu Asn Ile
    130                 135                 140

Lys Asn Thr Pro Leu Met Ala Phe Ser Val Gln Ala Asn Asp Ile Thr
145                 150                 155                 160

Phe Thr Asp Val Thr Ile Asn Asn Ala Asp Gly Asp Thr Gln Gly Gly
                165                 170                 175

His Asn Thr Asp Ala Phe Asp Val Gly Asn Ser Val Gly Val Asn Ile
            180                 185                 190

Ile Lys Pro Trp Val His Asn Gln Asp Asp Cys Leu Ala Val Asn Ser
        195                 200                 205

Gly Glu Asn Ile Trp Phe Thr Gly Gly Thr Cys Ile Gly Gly His Gly
    210                 215                 220

Leu Ser Ile Gly Ser Val Gly Asp Arg Ser Asn Asn Val Val Lys Asn
225                 230                 235                 240

Val Thr Ile Glu His Ser Thr Val Ser Asn Ser Glu Asn Ala Val Arg
                245                 250                 255

Ile Lys Thr Ile Ser Gly Ala Thr Gly Ser Val Ser Glu Ile Thr Tyr
            260                 265                 270

Ser Asn Ile Val Met Ser Gly Ile Ser Asp Tyr Gly Val Val Ile Gln
        275                 280                 285

Gln Asp Tyr Glu Asp Gly Lys Pro Thr Gly Lys Pro Thr Asn Gly Val
    290                 295                 300

Thr Ile Gln Asp Val Lys Leu Glu Ser Val Thr Gly Ser Val Asp Ser
305                 310                 315                 320

Gly Ala Thr Glu Ile Tyr Leu Leu Cys Gly Ser Gly Ser Cys Ser Asp
                325                 330                 335

Trp Thr Trp Asp Asp Val Lys Val Thr Gly Gly Lys Lys Ser Thr Ala
            340                 345                 350

Cys Lys Asn Phe Pro Ser Val Ala Ser Cys
        355                 360

<210> SEQ ID NO 38
<211> LENGTH: 383
<212> TYPE: PRT
<213> ORGANISM: Pseudomonas cellulosa

<400> SEQUENCE: 38

Arg Ala Asp Val Lys Pro Val Thr Val Lys Leu Val Asp Ser Gln Ala
1               5                   10                  15

Thr Met Glu Thr Arg Ser Leu Phe Ala Phe Met Gln Glu Gln Arg Arg
                20                  25                  30

His Ser Ile Met Phe Gly His Gln His Glu Thr Thr Gln Gly Leu Thr
            35                  40                  45

Ile Thr Arg Thr Asp Gly Thr Gln Ser Asp Thr Phe Asn Ala Val Gly
        50                  55                  60

Asp Phe Ala Ala Val Tyr Gly Trp Asp Thr Leu Ser Ile Val Ala Pro
65                  70                  75                  80

Lys Ala Glu Gly Asp Ile Val Ala Gln Val Lys Lys Ala Tyr Ala Arg

-continued

```
                85                  90                  95
Gly Gly Ile Ile Thr Val Ser Ser His Phe Asp Asn Pro Lys Thr Asp
            100                 105                 110

Thr Gln Lys Gly Val Trp Pro Val Gly Thr Ser Trp Asp Gln Thr Pro
            115                 120                 125

Ala Val Val Asp Ser Leu Pro Gly Gly Ala Tyr Asn Pro Val Leu Asn
            130                 135                 140

Gly Tyr Leu Asp Gln Val Ala Glu Trp Ala Asn Asn Leu Lys Asp Glu
145                 150                 155                 160

Gln Gly Arg Leu Ile Pro Val Ile Phe Arg Leu Tyr His Ala Asn Thr
                165                 170                 175

Gly Ser Trp Phe Trp Trp Gly Asp Lys Gln Ser Thr Pro Glu Gln Tyr
            180                 185                 190

Lys Gln Leu Phe Arg Tyr Ser Val Glu Tyr Leu Arg Asp Val Lys Gly
            195                 200                 205

Val Arg Asn Phe Leu Tyr Ala Tyr Ser Pro Asn Asn Phe Trp Asp Val
            210                 215                 220

Thr Glu Ala Asn Tyr Leu Glu Arg Tyr Pro Gly Asp Glu Trp Val Asp
225                 230                 235                 240

Val Leu Gly Phe Asp Thr Tyr Gly Pro Val Ala Asp Asn Ala Asp Trp
                245                 250                 255

Phe Arg Asn Val Val Ala Asn Ala Ala Leu Val Ala Arg Met Ala Glu
            260                 265                 270

Ala Arg Gly Lys Ile Pro Val Ile Ser Glu Ile Gly Ile Arg Ala Pro
            275                 280                 285

Asp Ile Glu Ala Gly Leu Tyr Asp Asn Gln Trp Tyr Arg Lys Leu Ile
            290                 295                 300

Ser Gly Leu Lys Ala Asp Pro Asp Ala Arg Glu Ile Ala Phe Leu Leu
305                 310                 315                 320

Val Trp Arg Asn Ala Pro Gln Gly Val Pro Gly Pro Asn Gly Thr Gln
                325                 330                 335

Val Pro His Tyr Trp Val Pro Ala Asn Arg Pro Glu Asn Ile Asn Asn
            340                 345                 350

Gly Thr Leu Glu Asp Phe Gln Ala Phe Tyr Ala Asp Glu Phe Thr Ala
            355                 360                 365

Phe Asn Arg Asp Ile Glu Gln Val Tyr Gln Arg Pro Thr Leu Ile
            370                 375                 380

<210> SEQ ID NO 39
<211> LENGTH: 419
<212> TYPE: PRT
<213> ORGANISM: Bacillus circulans

<400> SEQUENCE: 39

Leu Gln Pro Ala Thr Ala Glu Ala Ala Asp Ser Tyr Lys Ile Val Gly
1               5                   10                  15

Tyr Tyr Pro Ser Trp Ala Ala Tyr Gly Arg Asn Tyr Asn Val Ala Asp
            20                  25                  30

Ile Asp Pro Thr Lys Val Thr His Ile Asn Tyr Ala Phe Ala Asp Ile
            35                  40                  45

Cys Trp Asn Gly Ile His Gly Asn Pro Asp Pro Ser Gly Pro Asn Pro
        50                  55                  60

Val Thr Trp Thr Cys Gln Asn Glu Lys Ser Gln Thr Ile Asn Val Pro
65              70                  75                  80
```

```
Asn Gly Thr Ile Val Leu Gly Asp Pro Trp Ile Asp Thr Gly Lys Thr
                85                  90                  95

Phe Ala Gly Asp Thr Trp Asp Gln Pro Ile Ala Gly Asn Ile Asn Gln
            100                 105                 110

Leu Asn Lys Leu Lys Gln Thr Asn Pro Asn Leu Lys Thr Ile Ile Ser
        115                 120                 125

Val Gly Gly Trp Thr Trp Ser Asn Arg Phe Ser Asp Val Ala Ala Thr
    130                 135                 140

Ala Ala Thr Arg Glu Val Phe Ala Asn Ser Ala Val Asp Phe Leu Arg
145                 150                 155                 160

Lys Tyr Asn Phe Asp Gly Val Asp Leu Asp Trp Glu Tyr Pro Val Ser
                165                 170                 175

Gly Gly Leu Asp Gly Asn Ser Lys Arg Pro Glu Asp Lys Gln Asn Tyr
            180                 185                 190

Thr Leu Leu Leu Ser Lys Ile Arg Glu Lys Leu Asp Ala Ala Gly Ala
        195                 200                 205

Val Asp Gly Lys Lys Tyr Leu Leu Thr Ile Ala Ser Gly Ala Ser Ala
    210                 215                 220

Thr Tyr Ala Ala Asn Thr Glu Leu Ala Lys Ile Ala Ala Ile Val Asp
225                 230                 235                 240

Trp Ile Asn Ile Met Thr Tyr Asp Phe Asn Gly Ala Trp Gln Lys Ile
                245                 250                 255

Ser Ala His Asn Ala Pro Leu Asn Tyr Asp Pro Ala Ala Ser Ala Ala
            260                 265                 270

Gly Val Pro Asp Ala Asn Thr Phe Asn Val Ala Ala Gly Ala Gln Gly
        275                 280                 285

His Leu Asp Ala Gly Val Pro Ala Ala Lys Leu Val Leu Gly Val Pro
    290                 295                 300

Phe Tyr Gly Arg Gly Trp Asp Gly Cys Ala Gln Ala Gly Asn Gly Gln
305                 310                 315                 320

Tyr Gln Thr Cys Thr Gly Gly Ser Ser Val Gly Thr Trp Glu Ala Gly
                325                 330                 335

Ser Phe Asp Phe Tyr Asp Leu Glu Ala Asn Tyr Ile Asn Lys Asn Gly
            340                 345                 350

Tyr Thr Arg Tyr Trp Asn Asp Thr Ala Lys Val Pro Tyr Leu Tyr Asn
        355                 360                 365

Ala Ser Asn Lys Arg Phe Ile Ser Tyr Asp Asp Ala Glu Ser Val Gly
    370                 375                 380

Tyr Lys Thr Ala Tyr Ile Lys Ser Lys Gly Leu Gly Gly Ala Met Phe
385                 390                 395                 400

Trp Glu Leu Ser Gly Asp Arg Asn Lys Thr Leu Gln Asn Lys Leu Lys
                405                 410                 415

Ala Asp Leu

<210> SEQ ID NO 40
<211> LENGTH: 317
<212> TYPE: PRT
<213> ORGANISM: Candida antarctica

<400> SEQUENCE: 40

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30
```

```
Pro Ile Leu Leu Val Pro Gly Thr Gly Thr Gly Pro Gln Ser Phe
            35                  40                  45

Asp Ser Asn Trp Ile Pro Leu Ser Thr Gln Leu Gly Tyr Thr Pro Cys
        50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Asp His
    210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315
```

<210> SEQ ID NO 41
<211> LENGTH: 434
<212> TYPE: PRT
<213> ORGANISM: artificial sequence
<220> FEATURE:
<223> OTHER INFORMATION: chimera of guinea pig and homo sapiens (human=
      approx. last 30 amino acids)

<400> SEQUENCE: 41

```
Ala Glu Val Cys Tyr Ser His Leu Gly Cys Phe Ser Asp Glu Lys Pro
1               5                   10                  15

Trp Ala Gly Thr Ser Gln Arg Pro Ile Lys Ser Leu Pro Ser Asp Pro
            20                  25                  30

Lys Lys Ile Asn Thr Arg Phe Leu Leu Tyr Thr Asn Glu Asn Gln Asn
        35                  40                  45

Ser Tyr Gln Leu Ile Thr Ala Thr Asp Ile Ala Thr Ile Lys Ala Ser
    50                  55                  60

Asn Phe Asn Leu Asn Arg Lys Thr Arg Phe Ile Ile His Gly Phe Thr
65                  70                  75                  80
```

-continued

Asp Ser Gly Glu Asn Ser Trp Leu Ser Asp Met Cys Lys Asn Met Phe
                85                  90                  95

Gln Val Glu Lys Val Asn Cys Ile Cys Val Asp Trp Lys Gly Gly Ser
            100                 105                 110

Lys Ala Gln Tyr Ser Gln Ala Ser Gln Asn Ile Arg Val Val Gly Ala
        115                 120                 125

Glu Val Ala Tyr Leu Val Gln Val Leu Ser Thr Ser Leu Asn Tyr Ala
    130                 135                 140

Pro Glu Asn Val His Ile Ile Gly His Ser Leu Gly Ala His Thr Ala
145                 150                 155                 160

Gly Glu Ala Gly Lys Arg Leu Asn Gly Leu Val Gly Arg Ile Thr Gly
                165                 170                 175

Leu Asp Pro Ala Glu Pro Tyr Phe Gln Asp Thr Pro Glu Glu Val Arg
            180                 185                 190

Leu Asp Pro Ser Asp Ala Lys Phe Val Asp Val Ile His Thr Asp Ile
        195                 200                 205

Ser Pro Ile Leu Pro Ser Leu Gly Phe Gly Met Ser Gln Lys Val Gly
    210                 215                 220

His Met Asp Phe Phe Pro Asn Gly Gly Lys Asp Met Pro Gly Cys Lys
225                 230                 235                 240

Thr Gly Ile Ser Cys Asn His His Arg Ser Ile Glu Tyr Tyr His Ser
                245                 250                 255

Ser Ile Leu Asn Pro Glu Gly Phe Leu Gly Tyr Pro Cys Ala Ser Tyr
            260                 265                 270

Asp Glu Phe Gln Glu Ser Gly Cys Phe Pro Cys Pro Ala Lys Gly Cys
        275                 280                 285

Pro Lys Met Gly His Phe Ala Asp Gln Tyr Pro Gly Lys Thr Asn Ala
    290                 295                 300

Val Glu Gln Thr Phe Phe Leu Asn Thr Gly Ala Ser Asp Asn Phe Thr
305                 310                 315                 320

Arg Trp Arg Tyr Lys Val Thr Val Thr Leu Ser Gly Glu Lys Asp Pro
                325                 330                 335

Ser Gly Asn Ile Asn Val Ala Leu Leu Gly Lys Asn Gly Asn Ser Ala
            340                 345                 350

Gln Tyr Gln Val Phe Lys Gly Thr Leu Lys Pro Asp Ala Ser Tyr Thr
        355                 360                 365

Asn Ser Ile Asp Val Glu Leu Asn Val Gly Thr Ile Gln Lys Val Thr
    370                 375                 380

Phe Leu Trp Lys Arg Ser Gly Ile Ser Val Ser Lys Pro Lys Met Gly
385                 390                 395                 400

Ala Ser Arg Ile Thr Val Gln Ser Gly Lys Asp Gly Thr Lys Tyr Asn
                405                 410                 415

Phe Cys Ser Ser Asp Ile Val Gln Glu Asn Val Glu Gln Thr Leu Ser
            420                 425                 430

Pro Cys

<210> SEQ ID NO 42
<211> LENGTH: 471
<212> TYPE: PRT
<213> ORGANISM: Escherichia coli

<400> SEQUENCE: 42

Met Lys Gln Ser Thr Ile Ala Leu Ala Leu Leu Pro Leu Leu Phe Thr
1               5                   10                  15

```
Pro Val Thr Lys Ala Arg Thr Pro Glu Met Pro Val Leu Glu Asn Arg
                20                  25                  30

Ala Ala Gln Gly Asp Ile Thr Ala Pro Gly Gly Ala Arg Arg Leu Thr
            35                  40                  45

Gly Asp Gln Thr Ala Ala Leu Arg Asp Ser Leu Ser Asp Lys Pro Ala
        50                  55                  60

Lys Asn Ile Ile Leu Leu Ile Gly Asp Gly Met Gly Asp Ser Glu Ile
 65                  70                  75                  80

Thr Ala Ala Arg Asn Tyr Ala Glu Gly Ala Gly Gly Phe Phe Lys Gly
                85                  90                  95

Ile Asp Ala Leu Pro Leu Thr Gly Gln Tyr Thr His Tyr Ala Leu Asn
            100                 105                 110

Lys Lys Thr Gly Lys Pro Asp Tyr Val Thr Asp Ser Ala Ala Ser Ala
        115                 120                 125

Thr Ala Trp Ser Thr Gly Val Lys Thr Tyr Asn Gly Ala Leu Gly Val
    130                 135                 140

Asp Ile His Glu Lys Asp His Pro Thr Ile Leu Glu Met Ala Lys Ala
145                 150                 155                 160

Ala Gly Leu Ala Thr Gly Asn Val Ser Thr Ala Glu Leu Gln Asp Ala
                165                 170                 175

Thr Pro Ala Ala Leu Val Ala His Val Thr Ser Arg Lys Cys Tyr Gly
            180                 185                 190

Pro Ser Ala Thr Ser Glu Lys Cys Pro Gly Asn Ala Leu Glu Lys Gly
        195                 200                 205

Gly Lys Gly Ser Ile Thr Glu Gln Leu Leu Asn Ala Arg Ala Asp Val
    210                 215                 220

Thr Leu Gly Gly Gly Ala Lys Thr Phe Ala Glu Thr Ala Thr Ala Gly
225                 230                 235                 240

Glu Trp Gln Gly Lys Thr Leu Arg Glu Gln Ala Gln Ala Arg Gly Tyr
                245                 250                 255

Gln Leu Val Ser Asp Ala Ala Ser Leu Asn Ser Val Thr Glu Ala Asn
            260                 265                 270

Gln Gln Lys Pro Leu Leu Gly Leu Phe Ala Asp Gly Asn Met Pro Val
        275                 280                 285

Arg Trp Leu Gly Pro Lys Ala Thr Tyr His Gly Asn Ile Asp Lys Pro
    290                 295                 300

Ala Val Thr Cys Thr Pro Asn Pro Gln Arg Asn Asp Ser Val Pro Thr
305                 310                 315                 320

Leu Ala Gln Met Thr Asp Lys Ala Ile Glu Leu Leu Ser Lys Asn Glu
                325                 330                 335

Lys Gly Phe Phe Leu Gln Val Glu Gly Ala Ser Ile Asp Lys Gln Asp
            340                 345                 350

His Ala Ala Asn Pro Cys Gly Gln Ile Gly Glu Thr Val Asp Leu Asp
        355                 360                 365

Glu Ala Val Gln Arg Ala Leu Glu Phe Ala Lys Lys Glu Gly Asn Thr
    370                 375                 380

Leu Val Ile Val Thr Ala Asp His Ala His Ala Ser Gln Ile Val Ala
385                 390                 395                 400

Pro Asp Thr Lys Ala Pro Gly Leu Thr Gln Ala Leu Asn Thr Lys Asp
                405                 410                 415

Gly Ala Val Met Val Met Ser Tyr Gly Asn Ser Glu Glu Asp Ser Gln
            420                 425                 430
```

```
Glu His Thr Gly Ser Gln Leu Arg Ile Ala Ala Tyr Gly Pro His Ala
        435                 440                 445

Ala Asn Val Val Gly Leu Thr Asp Gln Thr Asp Leu Phe Tyr Thr Met
        450                 455                 460

Lys Ala Ala Leu Gly Leu Lys
465                 470

<210> SEQ ID NO 43
<211> LENGTH: 260
<212> TYPE: PRT
<213> ORGANISM: Bovine

<400> SEQUENCE: 43

Leu Lys Ile Ala Ala Phe Asn Ile Arg Thr Phe Gly Glu Thr Lys Met
1               5                   10                  15

Ser Asn Ala Thr Leu Ala Ser Tyr Ile Val Arg Ile Val Arg Arg Tyr
                20                  25                  30

Asp Ile Val Leu Ile Gln Glu Val Arg Asp Ser His Leu Val Ala Val
            35                  40                  45

Gly Lys Leu Leu Asp Tyr Leu Asn Gln Asp Asp Pro Asn Thr Tyr His
        50                  55                  60

Tyr Val Val Ser Glu Pro Leu Gly Arg Asn Ser Tyr Lys Glu Arg Tyr
65                  70                  75                  80

Leu Phe Leu Phe Arg Pro Asn Lys Val Ser Val Leu Asp Thr Tyr Gln
                85                  90                  95

Tyr Asp Asp Gly Cys Glu Ser Cys Gly Asn Asp Ser Phe Ser Arg Glu
            100                 105                 110

Pro Ala Val Val Lys Phe Ser Ser His Ser Thr Lys Val Lys Glu Phe
        115                 120                 125

Ala Ile Val Ala Leu His Ser Ala Pro Ser Asp Ala Val Ala Glu Ile
    130                 135                 140

Asn Ser Leu Tyr Asp Val Tyr Leu Asp Val Gln Gln Lys Trp His Leu
145                 150                 155                 160

Asn Asp Val Met Leu Met Gly Asp Phe Asn Ala Asp Cys Ser Tyr Val
                165                 170                 175

Thr Ser Ser Gln Trp Ser Ser Ile Arg Leu Arg Thr Ser Ser Thr Phe
            180                 185                 190

Gln Trp Leu Ile Pro Asp Ser Ala Asp Thr Thr Ala Thr Ser Thr Asn
        195                 200                 205

Cys Ala Tyr Asp Arg Ile Val Val Ala Gly Ser Leu Leu Gln Ser Ser
    210                 215                 220

Val Val Pro Gly Ser Ala Ala Pro Phe Asp Phe Gln Ala Ala Tyr Gly
225                 230                 235                 240

Leu Ser Asn Glu Met Ala Leu Ala Ile Ser Asp His Tyr Pro Val Glu
                245                 250                 255

Val Thr Leu Thr
            260

<210> SEQ ID NO 44
<211> LENGTH: 686
<212> TYPE: PRT
<213> ORGANISM: Bacillus circulans

<400> SEQUENCE: 44

Ala Pro Asp Thr Ser Val Ser Asn Lys Gln Asn Phe Ser Thr Asp Val
1               5                   10                  15
```

```
Ile Tyr Gln Ile Phe Thr Asp Arg Phe Ser Asp Gly Asn Pro Ala Asn
            20                  25                  30

Asn Pro Thr Gly Ala Ala Phe Asp Gly Thr Cys Thr Asn Leu Arg Leu
        35                  40                  45

Tyr Cys Gly Gly Asp Trp Gln Gly Ile Ile Asn Lys Ile Asn Asp Gly
 50                  55                  60

Tyr Leu Thr Gly Met Gly Val Thr Ala Ile Trp Ile Ser Gln Pro Val
65                   70                  75                  80

Glu Asn Ile Tyr Ser Ile Ile Asn Tyr Ser Gly Val Asn Asn Thr Ala
                85                  90                  95

Tyr His Gly Tyr Trp Ala Arg Asp Phe Lys Lys Thr Asn Pro Ala Tyr
            100                 105                 110

Gly Thr Ile Ala Asp Phe Gln Asn Leu Ile Ala Ala His Ala Lys
        115                 120                 125

Asn Ile Lys Val Ile Ile Asp Phe Ala Pro Asn His Thr Ser Pro Ala
130                 135                 140

Ser Ser Asp Gln Pro Ser Phe Ala Glu Asn Gly Arg Leu Tyr Asp Asn
145                 150                 155                 160

Gly Thr Leu Leu Gly Gly Tyr Thr Asn Asp Thr Gln Asn Leu Phe His
                165                 170                 175

His Asn Gly Gly Thr Asp Phe Ser Thr Thr Glu Asn Gly Ile Tyr Lys
            180                 185                 190

Asn Leu Tyr Asp Leu Ala Asp Leu Asn His Asn Asn Ser Thr Val Asp
        195                 200                 205

Val Tyr Leu Lys Asp Ala Ile Lys Met Trp Leu Asp Leu Gly Ile Asp
    210                 215                 220

Gly Ile Arg Met Asp Ala Val Lys His Met Pro Phe Gly Trp Gln Lys
225                 230                 235                 240

Ser Phe Met Ala Ala Val Asn Asn Tyr Lys Pro Val Phe Thr Phe Gly
                245                 250                 255

Glu Trp Phe Leu Gly Val Asn Glu Val Ser Pro Glu Asn His Lys Phe
            260                 265                 270

Ala Asn Glu Ser Gly Met Ser Leu Leu Asp Phe Arg Phe Ala Gln Lys
        275                 280                 285

Val Arg Gln Val Phe Arg Asp Asn Thr Asp Asn Met Tyr Gly Leu Lys
290                 295                 300

Ala Met Leu Glu Gly Ser Ala Ala Asp Tyr Ala Gln Val Asp Asp Gln
305                 310                 315                 320

Val Thr Phe Ile Asp Asn His Asp Met Glu Arg Phe His Ala Ser Asn
                325                 330                 335

Ala Asn Arg Arg Lys Leu Glu Gln Ala Leu Ala Phe Thr Leu Thr Ser
            340                 345                 350

Arg Gly Val Pro Ala Ile Tyr Tyr Gly Thr Glu Gln Tyr Met Ser Gly
        355                 360                 365

Gly Thr Asp Pro Asp Asn Arg Ala Arg Ile Pro Ser Phe Ser Thr Ser
370                 375                 380

Thr Thr Ala Tyr Gln Val Ile Gln Lys Leu Ala Pro Leu Arg Lys Cys
385                 390                 395                 400

Asn Pro Ala Ile Ala Tyr Gly Ser Thr Gln Glu Arg Trp Ile Asn Asn
                405                 410                 415

Asp Val Leu Ile Tyr Glu Arg Lys Phe Gly Ser Asn Val Ala Val Val
            420                 425                 430

Ala Val Asn Arg Asn Leu Asn Ala Pro Ala Ser Ile Ser Gly Leu Val
```

```
                  435                 440                 445
Thr Ser Leu Pro Gln Gly Ser Tyr Asn Asp Val Leu Gly Gly Leu Leu
    450                 455                 460

Asn Gly Asn Thr Leu Ser Val Gly Ser Gly Ala Ala Ser Asn Phe
465                 470                 475                 480

Thr Leu Ala Ala Gly Gly Thr Ala Val Trp Gln Tyr Thr Ala Thr
                485                 490                 495

Ala Thr Pro Thr Ile Gly His Val Gly Pro Met Met Ala Lys Pro Gly
            500                 505                 510

Val Thr Ile Thr Ile Asp Gly Arg Gly Phe Gly Ser Ser Lys Gly Thr
            515                 520                 525

Val Tyr Phe Gly Thr Thr Ala Val Ser Gly Ala Asp Ile Thr Ser Trp
    530                 535                 540

Glu Asp Thr Gln Ile Lys Val Lys Ile Pro Ala Val Ala Gly Gly Asn
545                 550                 555                 560

Tyr Asn Ile Lys Val Ala Asn Ala Ala Gly Thr Ala Ser Asn Val Tyr
                565                 570                 575

Asp Asn Phe Glu Val Leu Ser Gly Asp Gln Val Ser Val Arg Phe Val
            580                 585                 590

Val Asn Asn Ala Thr Thr Ala Leu Gly Gln Asn Val Tyr Leu Thr Gly
        595                 600                 605

Ser Val Ser Glu Leu Gly Asn Trp Asp Pro Ala Lys Ala Ile Gly Pro
    610                 615                 620

Met Tyr Asn Gln Val Val Tyr Gln Tyr Pro Asn Trp Tyr Tyr Asp Val
625                 630                 635                 640

Ser Val Pro Ala Gly Lys Thr Ile Glu Phe Lys Phe Leu Lys Lys Gln
                645                 650                 655

Gly Ser Thr Val Thr Trp Glu Gly Gly Ser Asn His Thr Phe Thr Ala
            660                 665                 670

Pro Ser Ser Gly Thr Ala Thr Ile Asn Val Asn Trp Gln Pro
        675                 680                 685

<210> SEQ ID NO 45
<211> LENGTH: 404
<212> TYPE: PRT
<213> ORGANISM: Amycolatopsis orientalis

<400> SEQUENCE: 45

Met Arg Val Leu Ile Thr Gly Cys Gly Ser Arg Gly Asp Thr Glu Pro
1               5                   10                  15

Leu Val Ala Leu Ala Ala Arg Leu Arg Glu Leu Gly Ala Asp Ala Arg
            20                  25                  30

Met Cys Leu Pro Pro Asp Tyr Val Glu Arg Cys Ala Glu Val Gly Val
        35                  40                  45

Pro Met Val Pro Val Gly Arg Ala Val Arg Ala Gly Ala Arg Glu Pro
    50                  55                  60

Gly Glu Leu Pro Pro Gly Ala Ala Glu Val Val Thr Glu Val Val Ala
65                  70                  75                  80

Glu Trp Phe Asp Lys Val Pro Ala Ala Ile Glu Gly Cys Asp Ala Val
                85                  90                  95

Val Thr Thr Gly Leu Leu Pro Ala Ala Val Ala Val Arg Ser Met Ala
            100                 105                 110

Glu Lys Leu Gly Ile Pro Tyr Arg Tyr Thr Val Leu Ser Pro Asp His
        115                 120                 125
```

-continued

Leu Pro Ser Glu Gln Ser Gln Ala Glu Arg Asp Met Tyr Asn Gln Gly
    130                 135                 140

Ala Asp Arg Leu Phe Gly Asp Ala Val Asn Ser His Arg Ala Ser Ile
145                 150                 155                 160

Gly Leu Pro Pro Val Glu His Leu Tyr Asp Tyr Gly Tyr Thr Asp Gln
                165                 170                 175

Pro Trp Leu Ala Ala Asp Pro Val Leu Ser Pro Leu Arg Pro Thr Asp
            180                 185                 190

Leu Gly Thr Val Gln Thr Gly Ala Trp Ile Leu Pro Asp Glu Arg Pro
        195                 200                 205

Leu Ser Ala Glu Leu Glu Ala Phe Leu Ala Ala Gly Ser Thr Pro Val
    210                 215                 220

Tyr Val Gly Phe Gly Ser Ser Ser Arg Pro Ala Thr Ala Asp Ala Ala
225                 230                 235                 240

Lys Met Ala Ile Lys Ala Val Arg Ala Ser Gly Arg Arg Ile Val Leu
                245                 250                 255

Ser Arg Gly Trp Ala Asp Leu Val Leu Pro Asp Asp Gly Ala Asp Cys
            260                 265                 270

Phe Val Val Gly Glu Val Asn Leu Gln Glu Leu Phe Gly Arg Val Ala
        275                 280                 285

Ala Ala Ile His His Asp Ser Ala Gly Thr Thr Leu Leu Ala Met Arg
    290                 295                 300

Ala Gly Ile Pro Gln Ile Val Val Arg Arg Val Val Asp Asn Val Val
305                 310                 315                 320

Glu Gln Ala Tyr His Ala Asp Arg Val Ala Glu Leu Gly Val Gly Val
                325                 330                 335

Ala Val Asp Gly Pro Val Pro Thr Ile Asp Ser Leu Ser Ala Ala Leu
            340                 345                 350

Asp Thr Ala Leu Ala Pro Glu Ile Arg Ala Arg Ala Thr Thr Val Ala
        355                 360                 365

Asp Thr Ile Arg Ala Asp Gly Thr Thr Val Ala Ala Gln Leu Leu Phe
    370                 375                 380

Asp Ala Val Ser Leu Glu Lys Pro Thr Val Pro Ala Leu Glu His His
385                 390                 395                 400

His His His His

<210> SEQ ID NO 46
<211> LENGTH: 292
<212> TYPE: PRT
<213> ORGANISM: Pseudomonas sp.

<400> SEQUENCE: 46

Ser Ile Glu Arg Leu Gly Tyr Leu Gly Phe Ala Val Lys Asp Val Pro
1               5                   10                  15

Ala Trp Asp His Phe Leu Thr Lys Ser Val Gly Leu Met Ala Ala Gly
            20                  25                  30

Ser Ala Gly Asp Ala Ala Leu Tyr Arg Ala Asp Gln Arg Ala Trp Arg
        35                  40                  45

Ile Ala Val Gln Pro Gly Glu Leu Asp Leu Ala Tyr Ala Gly Leu
    50                  55                  60

Glu Val Asp Asp Ala Ala Ala Leu Glu Arg Met Ala Asp Lys Leu Arg
65                  70                  75                  80

Gln Ala Gly Val Ala Phe Thr Arg Gly Asp Glu Ala Leu Met Gln Gln
                85                  90                  95

```
Arg Lys Val Met Gly Leu Leu Cys Leu Gln Asp Pro Phe Gly Leu Pro
            100                 105                 110

Leu Glu Ile Tyr Tyr Gly Pro Ala Glu Ile Phe His Glu Pro Phe Leu
        115                 120                 125

Pro Ser Ala Pro Val Ser Gly Phe Val Thr Gly Asp Gln Gly Ile Gly
    130                 135                 140

His Phe Val Arg Cys Val Pro Asp Thr Ala Lys Ala Met Ala Phe Tyr
145                 150                 155                 160

Thr Glu Val Leu Gly Phe Val Leu Ser Asp Ile Ile Asp Ile Gln Met
                165                 170                 175

Gly Pro Glu Thr Ser Val Pro Ala His Phe Leu His Cys Asn Gly Arg
            180                 185                 190

His His Thr Ile Ala Leu Ala Ala Phe Pro Ile Pro Lys Arg Ile His
        195                 200                 205

His Phe Met Leu Gln Ala Asn Thr Ile Asp Asp Val Gly Tyr Ala Phe
    210                 215                 220

Asp Arg Leu Asp Ala Ala Gly Arg Ile Thr Ser Leu Leu Gly Arg His
225                 230                 235                 240

Thr Asn Asp Gln Thr Leu Ser Phe Tyr Ala Asp Thr Pro Ser Pro Met
                245                 250                 255

Ile Glu Val Glu Phe Gly Trp Gly Pro Arg Thr Val Asp Ser Ser Trp
            260                 265                 270

Thr Val Ala Arg His Ser Arg Thr Ala Met Trp Gly His Lys Ser Val
        275                 280                 285

Arg Gly Gln Arg
    290

<210> SEQ ID NO 47
<211> LENGTH: 311
<212> TYPE: PRT
<213> ORGANISM: Acitenobacter sp.

<400> SEQUENCE: 47

Met Glu Val Lys Ile Phe Asn Thr Gln Asp Val Gln Asp Phe Leu Arg
1               5                   10                  15

Val Ala Ser Gly Leu Glu Gln Glu Gly Gly Asn Pro Arg Val Lys Gln
            20                  25                  30

Ile Ile His Arg Val Leu Ser Asp Leu Tyr Lys Ala Ile Glu Asp Leu
        35                  40                  45

Asn Ile Thr Ser Asp Glu Tyr Trp Ala Gly Val Ala Tyr Leu Asn Gln
    50                  55                  60

Leu Gly Ala Asn Gln Glu Ala Gly Leu Leu Ser Pro Gly Leu Gly Phe
65                  70                  75                  80

Asp His Tyr Leu Asp Met Arg Met Asp Ala Glu Asp Ala Leu Gly
                85                  90                  95

Ile Glu Asn Ala Thr Pro Arg Thr Ile Glu Gly Pro Leu Tyr Val Ala
            100                 105                 110

Gly Ala Pro Glu Ser Val Gly Tyr Ala Arg Met Asp Asp Gly Ser Asp
        115                 120                 125

Pro Asn Gly His Thr Leu Ile Leu His Gly Thr Ile Phe Asp Ala Asp
    130                 135                 140

Gly Lys Pro Leu Pro Asn Ala Lys Val Glu Ile Trp His Ala Asn Thr
145                 150                 155                 160

Lys Gly Phe Tyr Ser His Phe Asp Pro Thr Gly Glu Gln Gln Ala Phe
                165                 170                 175
```

Asn Met Arg Arg Ser Ile Ile Thr Asp Glu Asn Gly Gln Tyr Arg Val
            180                 185                 190

Arg Thr Ile Leu Pro Ala Gly Tyr Gly Cys Pro Pro Glu Gly Pro Thr
            195                 200                 205

Gln Gln Leu Leu Asn Gln Leu Gly Arg His Gly Asn Arg Pro Ala His
            210                 215                 220

Ile His Tyr Phe Val Ser Ala Asp Gly His Arg Lys Leu Thr Thr Gln
225                 230                 235                 240

Ile Asn Val Ala Gly Asp Pro Tyr Thr Tyr Asp Asp Phe Ala Tyr Ala
            245                 250                 255

Thr Arg Glu Gly Leu Val Val Asp Ala Val Glu His Thr Asp Pro Glu
            260                 265                 270

Ala Ile Lys Ala Asn Asp Val Glu Gly Pro Phe Ala Glu Met Val Phe
            275                 280                 285

Asp Leu Lys Leu Thr Arg Leu Val Asp Gly Val Asp Asn Gln Val Val
            290                 295                 300

Asp Arg Pro Arg Leu Ala Val
305                 310

<210> SEQ ID NO 48
<211> LENGTH: 414
<212> TYPE: PRT
<213> ORGANISM: Pseudomonas putida

<400> SEQUENCE: 48

Thr Thr Glu Thr Ile Gln Ser Asn Ala Asn Leu Ala Pro Leu Pro Pro
1               5                   10                  15

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
            35                  40                  45

Asn Val Pro Asp Leu Val Trp Thr Arg Cys Asn Gly Gly His Trp Ile
50                  55                  60

Ala Thr Arg Gly Gln Leu Ile Arg Glu Ala Tyr Glu Asp Tyr Arg His
65                  70                  75                  80

Phe Ser Ser Glu Cys Pro Phe Ile Pro Arg Glu Ala Gly Glu Ala Tyr
            85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
            115                 120                 125

Asn Arg Ile Gln Glu Leu Ala Cys Ser Leu Ile Glu Ser Leu Arg Pro
            130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
            165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
            195                 200                 205

Glu Gln Arg Arg Gln Lys Pro Gly Thr Asp Ala Ile Ser Ile Val Ala
            210                 215                 220

Asn Gly Gln Val Asn Gly Arg Pro Ile Thr Ser Asp Glu Ala Lys Arg

-continued

```
                225                 230                 235                 240
Met Cys Gly Leu Leu Leu Val Gly Gly Leu Asp Thr Val Val Asn Phe
                    245                 250                 255

Leu Ser Phe Ser Met Glu Phe Leu Ala Lys Ser Pro Glu His Arg Gln
                260                 265                 270

Glu Leu Ile Gln Arg Pro Glu Arg Ile Pro Ala Ala Cys Glu Glu Leu
            275                 280                 285

Leu Arg Arg Phe Ser Leu Val Ala Asp Gly Arg Ile Leu Thr Ser Asp
        290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Glu Asn Ala Cys Pro Met
                325                 330                 335

His Val Asp Phe Ser Arg Gln Lys Val Ser His Thr Thr Phe Gly His
                340                 345                 350

Gly Ser His Leu Cys Leu Gly Gln His Leu Ala Arg Arg Glu Ile Ile
            355                 360                 365

Val Thr Leu Lys Glu Trp Leu Thr Arg Ile Pro Asp Phe Ser Ile Ala
        370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                    405                 410

<210> SEQ ID NO 49
<211> LENGTH: 374
<212> TYPE: PRT
<213> ORGANISM: Equus caballus

<400> SEQUENCE: 49

Ser Thr Ala Gly Lys Val Ile Lys Cys Lys Ala Ala Val Leu Trp Glu
1               5                   10                  15

Glu Lys Lys Pro Phe Ser Ile Glu Glu Val Glu Val Ala Pro Pro Lys
                20                  25                  30

Ala His Glu Val Arg Ile Lys Met Val Ala Thr Gly Ile Cys Arg Ser
            35                  40                  45

Asp Asp His Val Val Ser Gly Thr Leu Val Thr Pro Leu Pro Val Ile
        50                  55                  60

Ala Gly His Glu Ala Ala Gly Ile Val Glu Ser Ile Gly Glu Gly Val
65                  70                  75                  80

Thr Thr Val Arg Pro Gly Asp Lys Val Ile Pro Leu Phe Thr Pro Gln
                85                  90                  95

Cys Gly Lys Cys Arg Val Cys Lys His Pro Glu Gly Asn Phe Cys Leu
            100                 105                 110

Lys Asn Asp Leu Ser Met Pro Arg Gly Thr Met Gln Asp Gly Thr Ser
        115                 120                 125

Arg Phe Thr Cys Arg Gly Lys Pro Ile His His Phe Leu Gly Thr Ser
    130                 135                 140

Thr Phe Ser Gln Tyr Thr Val Val Asp Glu Ile Ser Val Ala Lys Ile
145                 150                 155                 160

Asp Ala Ala Ser Pro Leu Glu Lys Val Cys Leu Ile Gly Cys Gly Phe
                165                 170                 175

Ser Thr Gly Tyr Gly Ser Ala Val Lys Val Ala Lys Val Thr Gln Gly
            180                 185                 190
```

```
Ser Thr Cys Ala Val Phe Gly Leu Gly Gly Val Gly Leu Ser Val Ile
        195                 200                 205

Met Gly Cys Lys Ala Ala Gly Ala Ala Arg Ile Ile Gly Val Asp Ile
        210                 215                 220

Asn Lys Asp Lys Phe Ala Lys Ala Lys Glu Val Gly Ala Thr Glu Cys
225                 230                 235                 240

Val Asn Pro Gln Asp Tyr Lys Lys Pro Ile Gln Glu Val Leu Thr Glu
                245                 250                 255

Met Ser Asn Gly Gly Val Asp Phe Ser Phe Glu Val Ile Gly Arg Leu
            260                 265                 270

Asp Thr Met Val Thr Ala Leu Ser Cys Cys Gln Glu Ala Tyr Gly Val
        275                 280                 285

Ser Val Ile Val Gly Val Pro Pro Asp Ser Gln Asn Leu Ser Met Asn
        290                 295                 300

Pro Met Leu Leu Leu Ser Gly Arg Thr Trp Lys Gly Ala Ile Phe Gly
305                 310                 315                 320

Gly Phe Lys Ser Lys Asp Ser Val Pro Lys Leu Val Ala Asp Phe Met
                325                 330                 335

Ala Lys Lys Phe Ala Leu Asp Pro Leu Ile Thr His Val Leu Pro Phe
            340                 345                 350

Glu Lys Ile Asn Glu Gly Phe Asp Leu Leu Arg Ser Gly Glu Ser Ile
        355                 360                 365

Arg Thr Ile Leu Thr Phe
    370

<210> SEQ ID NO 50
<211> LENGTH: 297
<212> TYPE: PRT
<213> ORGANISM: Escherichia coli

<400> SEQUENCE: 50

Met Ala Thr Asn Leu Arg Gly Val Met Ala Ala Leu Leu Thr Pro Phe
1               5                   10                  15

Asp Gln Gln Gln Ala Leu Asp Lys Ala Ser Leu Arg Arg Leu Val Gln
            20                  25                  30

Phe Asn Ile Gln Gln Gly Ile Asp Gly Leu Tyr Val Gly Gly Ser Thr
        35                  40                  45

Gly Glu Ala Phe Val Gln Ser Leu Ser Glu Arg Glu Gln Val Leu Glu
    50                  55                  60

Ile Val Ala Glu Glu Gly Lys Gly Lys Ile Lys Leu Ile Ala His Val
65                  70                  75                  80

Gly Cys Val Thr Thr Ala Glu Ser Gln Gln Leu Ala Ala Ser Ala Lys
                85                  90                  95

Arg Tyr Gly Phe Asp Ala Val Ser Ala Val Thr Pro Phe Tyr Tyr Pro
            100                 105                 110

Phe Ser Phe Glu Glu His Cys Asp His Tyr Arg Ala Ile Ile Asp Ser
        115                 120                 125

Ala Asp Gly Leu Pro Met Val Val Tyr Asn Ile Pro Ala Leu Ser Gly
    130                 135                 140

Val Lys Leu Thr Leu Asp Gln Ile Asn Thr Leu Val Thr Leu Pro Gly
145                 150                 155                 160

Val Gly Ala Leu Lys Gln Thr Ser Gly Asp Leu Tyr Gln Met Glu Gln
                165                 170                 175

Ile Arg Arg Glu His Pro Asp Leu Val Leu Tyr Asn Gly Tyr Asp Glu
            180                 185                 190
```

```
Ile Phe Ala Ser Gly Leu Leu Ala Gly Ala Asp Gly Gly Ile Gly Ser
        195                 200                 205

Thr Tyr Asn Ile Met Gly Trp Arg Tyr Gln Gly Ile Val Lys Ala Leu
        210                 215                 220

Lys Glu Gly Asp Ile Gln Thr Ala Gln Lys Leu Gln Thr Glu Cys Asn
225                 230                 235                 240

Lys Val Ile Asp Leu Leu Ile Lys Thr Gly Val Phe Arg Gly Leu Lys
                245                 250                 255

Thr Val Leu His Tyr Met Asp Val Val Ser Val Pro Leu Cys Arg Lys
        260                 265                 270

Pro Phe Gly Pro Val Asp Glu Lys Tyr Leu Pro Glu Leu Lys Ala Leu
        275                 280                 285

Ala Gln Gln Leu Met Gln Glu Arg Gly
        290                 295

<210> SEQ ID NO 51
<211> LENGTH: 268
<212> TYPE: PRT
<213> ORGANISM: Salmonella typhimurium

<400> SEQUENCE: 51

Met Glu Arg Tyr Glu Asn Leu Phe Ala Gln Leu Asn Asp Arg Arg Glu
1               5                   10                  15

Gly Ala Phe Val Pro Phe Val Thr Leu Gly Asp Pro Gly Ile Glu Gln
                20                  25                  30

Ser Leu Lys Ile Ile Asp Thr Leu Ile Asp Ala Gly Ala Asp Ala Leu
            35                  40                  45

Glu Leu Gly Val Pro Phe Ser Asp Pro Leu Ala Asp Gly Pro Thr Ile
        50                  55                  60

Gln Asn Ala Asn Leu Arg Ala Phe Ala Ala Gly Val Thr Pro Ala Gln
65                  70                  75                  80

Cys Phe Glu Met Leu Ala Leu Ile Arg Glu Lys His Pro Thr Ile Pro
                85                  90                  95

Ile Gly Leu Leu Met Tyr Ala Asn Leu Val Phe Asn Asn Gly Ile Asp
            100                 105                 110

Ala Phe Tyr Ala Arg Cys Glu Gln Val Gly Val Asp Ser Val Leu Val
        115                 120                 125

Ala Asp Val Pro Val Glu Glu Ser Ala Pro Phe Arg Gln Ala Ala Leu
130                 135                 140

Arg His Asn Ile Ala Pro Ile Phe Ile Cys Pro Pro Asn Ala Asp Asp
145                 150                 155                 160

Asp Leu Leu Arg Gln Val Ala Ser Tyr Gly Arg Gly Tyr Thr Tyr Leu
                165                 170                 175

Leu Ser Arg Ser Gly Val Thr Gly Ala Glu Asn Arg Gly Ala Leu Pro
            180                 185                 190

Leu His His Leu Ile Glu Lys Leu Lys Glu Tyr His Ala Ala Pro Ala
        195                 200                 205

Leu Gln Gly Phe Gly Ile Ser Ser Pro Glu Gln Val Ser Ala Ala Val
        210                 215                 220

Arg Ala Gly Ala Ala Gly Ala Ile Ser Gly Ser Ala Ile Val Lys Ile
225                 230                 235                 240

Ile Glu Lys Asn Leu Ala Ser Pro Lys Gln Met Leu Ala Glu Leu Arg
                245                 250                 255

Ser Phe Val Ser Ala Met Lys Ala Ala Ser Arg Ala
            260                 265
```

-continued

```
                    260                 265

<210> SEQ ID NO 52
<211> LENGTH: 393
<212> TYPE: PRT
<213> ORGANISM: Actinoplanes missouriensis

<400> SEQUENCE: 52

Ser Val Gln Ala Thr Arg Glu Asp Lys Phe Ser Phe Gly Leu Trp Thr
1               5                   10                  15

Val Gly Trp Gln Ala Arg Asp Ala Phe Gly Asp Ala Thr Arg Thr Ala
            20                  25                  30

Leu Asp Pro Val Glu Ala Val His Lys Leu Ala Glu Ile Gly Ala Tyr
        35                  40                  45

Gly Ile Thr Phe His Asp Asp Leu Val Pro Phe Gly Ser Asp Ala
    50                  55                  60

Gln Thr Arg Asp Gly Ile Ile Ala Gly Phe Lys Lys Ala Leu Asp Glu
65                  70                  75                  80

Thr Gly Leu Ile Val Pro Met Val Thr Thr Asn Leu Phe Thr His Pro
                85                  90                  95

Val Phe Lys Asp Gly Gly Phe Thr Ser Asn Asp Arg Ser Val Arg Arg
            100                 105                 110

Tyr Ala Ile Arg Lys Val Leu Arg Gln Met Asp Leu Gly Ala Glu Leu
        115                 120                 125

Gly Ala Lys Thr Leu Val Leu Trp Gly Gly Arg Glu Gly Ala Glu Tyr
    130                 135                 140

Asp Ser Ala Lys Asp Val Ser Ala Ala Leu Asp Arg Tyr Arg Glu Ala
145                 150                 155                 160

Leu Asn Leu Leu Ala Gln Tyr Ser Glu Asp Arg Gly Tyr Gly Leu Arg
                165                 170                 175

Phe Ala Ile Glu Pro Lys Pro Asn Glu Pro Arg Gly Asp Ile Leu Leu
            180                 185                 190

Pro Thr Ala Gly His Ala Ile Ala Phe Val Gln Glu Leu Glu Arg Pro
        195                 200                 205

Glu Leu Phe Gly Ile Asn Pro Glu Thr Gly Asn Glu Gln Met Ser Asn
    210                 215                 220

Leu Asn Phe Thr Gln Gly Ile Ala Gln Ala Leu Trp His Lys Lys Leu
225                 230                 235                 240

Phe His Ile Asp Leu Asn Gly Gln His Gly Pro Lys Phe Asp Gln Asp
                245                 250                 255

Leu Val Phe Gly His Gly Asp Leu Leu Asn Ala Phe Ser Leu Val Asp
            260                 265                 270

Leu Leu Glu Asn Gly Pro Asp Gly Ala Pro Ala Tyr Asp Gly Pro Arg
        275                 280                 285

His Phe Asp Tyr Lys Pro Ser Arg Thr Glu Asp Tyr Asp Gly Val Trp
    290                 295                 300

Glu Ser Ala Lys Ala Asn Ile Arg Met Tyr Leu Leu Leu Lys Glu Arg
305                 310                 315                 320

Ala Lys Ala Phe Arg Ala Asp Pro Glu Val Gln Glu Ala Leu Ala Ala
                325                 330                 335

Ser Lys Val Ala Glu Leu Lys Thr Pro Thr Leu Asn Pro Gly Glu Gly
            340                 345                 350

Tyr Ala Glu Leu Leu Ala Asp Arg Ser Ala Phe Glu Asp Tyr Asp Ala
        355                 360                 365
```

```
Asp Ala Val Gly Ala Lys Gly Phe Gly Phe Val Lys Leu Asn Gln Leu
    370                 375                 380

Ala Ile Glu His Leu Leu Gly Ala Arg
385                 390

<210> SEQ ID NO 53
<211> LENGTH: 348
<212> TYPE: PRT
<213> ORGANISM: Bacteriophage T7

<400> SEQUENCE: 53

Val Asn Ile Lys Thr Asn Pro Phe Lys Ala Val Ser Phe Val Glu Ser
1               5                   10                  15

Ala Ile Lys Lys Ala Leu Asp Asn Ala Gly Tyr Leu Ile Ala Glu Ile
            20                  25                  30

Lys Tyr Asp Gly Val Arg Gly Asn Ile Cys Val Asp Asn Thr Ala Asn
        35                  40                  45

Ser Tyr Trp Leu Ser Arg Val Ser Lys Thr Ile Pro Ala Leu Glu His
    50                  55                  60

Leu Asn Gly Phe Asp Val Arg Trp Lys Arg Leu Leu Asn Asp Asp Arg
65                  70                  75                  80

Cys Phe Tyr Lys Asp Gly Phe Met Leu Asp Gly Glu Leu Met Val Lys
                85                  90                  95

Gly Val Asp Phe Asn Thr Gly Ser Gly Leu Leu Arg Thr Lys Trp Thr
            100                 105                 110

Asp Thr Lys Asn Gln Glu Phe His Glu Glu Leu Phe Val Glu Pro Ile
        115                 120                 125

Arg Lys Lys Asp Lys Val Pro Phe Lys Leu His Thr Gly His Leu His
    130                 135                 140

Ile Lys Leu Tyr Ala Ile Leu Pro Leu His Ile Val Glu Ser Gly Glu
145                 150                 155                 160

Asp Cys Asp Val Met Thr Leu Leu Met Gln Glu His Val Lys Asn Met
                165                 170                 175

Leu Pro Leu Leu Gln Glu Tyr Phe Pro Glu Ile Glu Trp Gln Ala Ala
            180                 185                 190

Glu Ser Tyr Glu Val Tyr Asp Met Val Glu Leu Gln Gln Leu Tyr Glu
        195                 200                 205

Gln Lys Arg Ala Glu Gly His Glu Gly Leu Ile Val Lys Asp Pro Met
    210                 215                 220

Cys Ile Tyr Lys Arg Gly Lys Lys Ser Gly Trp Trp Lys Met Lys Pro
225                 230                 235                 240

Glu Asn Glu Ala Asp Gly Ile Ile Gln Gly Leu Val Trp Gly Thr Lys
                245                 250                 255

Gly Leu Ala Asn Glu Gly Lys Val Ile Gly Phe Glu Val Leu Leu Glu
            260                 265                 270

Ser Gly Arg Leu Val Asn Ala Thr Asn Ile Ser Arg Ala Leu Met Asp
        275                 280                 285

Glu Phe Thr Glu Thr Val Lys Glu Ala Thr Leu Ser Gln Trp Gly Phe
    290                 295                 300

Phe Ser Pro Tyr Gly Ile Gly Asp Asn Asp Ala Cys Thr Ile Asn Pro
305                 310                 315                 320

Tyr Asp Gly Trp Ala Cys Gln Ile Ser Tyr Met Glu Glu Thr Pro Asp
                325                 330                 335

Gly Ser Leu Arg His Pro Ser Phe Val Met Phe Arg
            340                 345
```

```
<210> SEQ ID NO 54
<211> LENGTH: 42
<212> TYPE: DNA
<213> ORGANISM: artificial sequence
<220> FEATURE:
<223> OTHER INFORMATION: binding site for restr1 and restr2
<220> FEATURE:
<221> NAME/KEY: CDS
<222> LOCATION: (2)..(40)

<400> SEQUENCE: 54 g gtg gta tca gca ggc cac tgc tac aag tcc cgc atc cag gt       42
  Val Val Ser Ala Gly His Cys Tyr Lys Ser Arg Ile Gln
  1               5                   10

<210> SEQ ID NO 55
<211> LENGTH: 13
<212> TYPE: PRT
<213> ORGANISM: artificial sequence
<220> FEATURE:
<223> OTHER INFORMATION: binding site for restr1 and restr2

<400> SEQUENCE: 55

Val Val Ser Ala Gly His Cys Tyr Lys Ser Arg Ile Gln
1               5                   10

<210> SEQ ID NO 56
<211> LENGTH: 42
<212> TYPE: DNA
<213> ORGANISM: artificial sequence
<220> FEATURE:
<223> OTHER INFORMATION: forward primer restr1

<400> SEQUENCE: 56
ggtggtatcc gcgggccact gctacaagtc ccggatccag gt                 42

<210> SEQ ID NO 57
<211> LENGTH: 42
<212> TYPE: DNA
<213> ORGANISM: artificial sequence
<220> FEATURE:
<223> OTHER INFORMATION: reverse primer restr2

<400> SEQUENCE: 57
acctggatcc gggacttgta gcagtggccc gcggatacca cc                 42

<210> SEQ ID NO 58
<211> LENGTH: 50
<212> TYPE: DNA
<213> ORGANISM: artificial sequence
<220> FEATURE:
<223> OTHER INFORMATION: binding site for restr3 and restr4
<220> FEATURE:
<221> NAME/KEY: CDS
<222> LOCATION: (3)..(50)

<400> SEQUENCE: 58 cc act ggc acg aag tgc ctc atc tct ggc tgg ggc aac act gcg agc    47
   Thr Gly Thr Lys Cys Leu Ile Ser Gly Trp Gly Asn Thr Ala Ser
   1               5                   10                  15 tct                                                            50
Ser

<210> SEQ ID NO 59
<211> LENGTH: 16
<212> TYPE: PRT
```

```
<213> ORGANISM: artificial sequence
<220> FEATURE:
<223> OTHER INFORMATION: binding site for restr3 and restr4

<400> SEQUENCE: 59

Thr Gly Thr Lys Cys Leu Ile Ser Gly Trp Gly Asn Thr Ala Ser Ser
1               5                   10                  15

<210> SEQ ID NO 60
<211> LENGTH: 50
<212> TYPE: DNA
<213> ORGANISM: artificial sequence
<220> FEATURE:
<223> OTHER INFORMATION: forward primer restr3

<400> SEQUENCE: 60
ccactggcac gaagtgcctc atctctggct ggggcaacac tgcgagctct            50

<210> SEQ ID NO 61
<211> LENGTH: 50
<212> TYPE: DNA
<213> ORGANISM: artificial sequence
<220> FEATURE:
<223> OTHER INFORMATION: reverse primer restr4

<400> SEQUENCE: 61
agagctagca gtgttgcccc agccagagat gaggcacttg gtaccagtgg            50

<210> SEQ ID NO 62
<211> LENGTH: 30
<212> TYPE: DNA
<213> ORGANISM: artificial sequence
<220> FEATURE:
<223> OTHER INFORMATION: primer puc-forward

<400> SEQUENCE: 62
ggggtacccc accaccatga atccactcct                                  30

<210> SEQ ID NO 63
<211> LENGTH: 30
<212> TYPE: DNA
<213> ORGANISM: artificial sequence
<220> FEATURE:
<223> OTHER INFORMATION: primer puc-reverse

<400> SEQUENCE: 63
cgggatccgg tatagagact gaagagatac                                  30

<210> SEQ ID NO 64
<211> LENGTH: 39
<212> TYPE: DNA
<213> ORGANISM: artificial sequence
<220> FEATURE:
<223> OTHER INFORMATION: oligox-SDR1f
<220> FEATURE:
<221> NAME/KEY: misc_feature
<222> LOCATION: 1 - 39
<223> OTHER INFORMATION: any nucleotide
<220> FEATURE:
<221> NAME/KEY: CDS
<222> LOCATION: (2)..(37)

<400> SEQUENCE: 64 g ggc cac tgc tac nnn nnn nnn nnn nnn nnn aag tcc cg             39
  Gly His Cys Tyr Xaa Xaa Xaa Xaa Xaa Xaa Lys Ser
  1               5                   10
```

```
<210> SEQ ID NO 65
<211> LENGTH: 12
<212> TYPE: PRT
<213> ORGANISM: artificial sequence
<220> FEATURE:
<221> NAME/KEY: Variant
<222> LOCATION: 1 - 12
<223> OTHER INFORMATION: any amino acid
<220> FEATURE:
<223> OTHER INFORMATION: oligox-SDR1f

<400> SEQUENCE: 65

Gly His Cys Tyr Xaa Xaa Xaa Xaa Xaa Xaa Lys Ser
1               5                   10

<210> SEQ ID NO 66
<211> LENGTH: 45
<212> TYPE: DNA
<213> ORGANISM: artificial sequence
<220> FEATURE:
<223> OTHER INFORMATION: oligox-SDR1r
<220> FEATURE:
<221> NAME/KEY: misc_feature
<222> LOCATION: 1 - 45
<223> OTHER INFORMATION: any nucleotide

<400> SEQUENCE: 66
cgcccggtga cgatgnnnnn nnnnnnnnnn nnnttcaggg cctag               45

<210> SEQ ID NO 67
<211> LENGTH: 47
<212> TYPE: DNA
<213> ORGANISM: artificial sequence
<220> FEATURE:
<223> OTHER INFORMATION: oligox-SDR2f
<220> FEATURE:
<221> NAME/KEY: CDS
<222> LOCATION: 2 - 46
<220> FEATURE:
<221> NAME/KEY: misc_feature
<222> LOCATION: 1 - 47
<223> OTHER INFORMATION: any nucleotide

<400> SEQUENCE: 67 c aag tgc ctc atc tct ggc tgg ggc aac nnn nnn nnn nnn nnn act g       47
  Lys Cys Leu Ile Ser Gly Trp Gly Asn Xaa Xaa Xaa Xaa Xaa Thr
  1               5                   10                  15

<210> SEQ ID NO 68
<211> LENGTH: 15
<212> TYPE: PRT
<213> ORGANISM: artificial sequence
<220> FEATURE:
<223> OTHER INFORMATION: oligox-SDR2f
<220> FEATURE:
<221> NAME/KEY: Variant
<222> LOCATION: 1 - 15
<223> OTHER INFORMATION: any amino acid

<400> SEQUENCE: 68

Lys Cys Leu Ile Ser Gly Trp Gly Asn Xaa Xaa Xaa Xaa Xaa Thr
1               5                   10                  15

<210> SEQ ID NO 69
<211> LENGTH: 55
<212> TYPE: DNA
<213> ORGANISM: artificial sequence
<220> FEATURE:
<223> OTHER INFORMATION: oligox-SDR2r
<220> FEATURE:
<221> NAME/KEY: misc_feature
```

```
<222> LOCATION: 1 - 55
<223> OTHER INFORMATION: any nucleotide

<400> SEQUENCE: 69
catggttcac ggagtagaga ccgaccccgt tgnnnnnnnn nnnnnnntga cgatc          55

<210> SEQ ID NO 70
<211> LENGTH: 59
<212> TYPE: DNA
<213> ORGANISM: artificial sequence
<220> FEATURE:
<223> OTHER INFORMATION: primer SDR1-mutnnb-forward
<220> FEATURE:
<221> NAME/KEY: misc_feature
<222> LOCATION: 1 - 59
<223> OTHER INFORMATION: N=A, C, G, T; B=C, G, T

<400> SEQUENCE: 70
tggtatccgc gggccactgc tacnnbnnbn nbnnbnnbnn baagtcccgg atccaggtg     59

<210> SEQ ID NO 71
<211> LENGTH: 52
<212> TYPE: DNA
<213> ORGANISM: artificial sequence
<220> FEATURE:
<223> OTHER INFORMATION: primer SDR2-mutnnb-reverse
<220> FEATURE:
<221> NAME/KEY: misc_feature
<222> LOCATION: 1 - 52
<223> OTHER INFORMATION: N=A, C, G, T; V=A, C, G

<400> SEQUENCE: 71
ggcgccagag ctagcagtvn nvnnvnnvnn vnngttgccc cagccagaga tg            52

<210> SEQ ID NO 72
<211> LENGTH: 6
<212> TYPE: PRT
<213> ORGANISM: artificial sequence
<220> FEATURE:
<223> OTHER INFORMATION: variant g SDR1

<400> SEQUENCE: 72

Ala Phe Phe Asn Gly Asp
1               5

<210> SEQ ID NO 73
<211> LENGTH: 5
<212> TYPE: PRT
<213> ORGANISM: artificial sequence
<220> FEATURE:
<223> OTHER INFORMATION: variant g SDR2

<400> SEQUENCE: 73

Arg Lys Asp Pro Trp
1               5

<210> SEQ ID NO 74
<211> LENGTH: 234
<212> TYPE: PRT
<213> ORGANISM: artificial sequence
<220> FEATURE:
<223> OTHER INFORMATION: artificial sequence

<400> SEQUENCE: 74

Ile Val Gly Gly Tyr Asn Cys Glu Glu Asn Ser Val Pro Tyr Gln Val
1               5                   10                  15

Ser Leu Asn Ser Gly Tyr His Phe Cys Gly Gly Ser Leu Ile Asn Glu
```

```
                    20                  25                  30

Gln Trp Val Val Ser Ala Gly His Cys Tyr Ala Ala Phe Asn Gly Lys
            35                  40                  45

Ser Arg Ile Gln Val Arg Leu Gly Glu His Asn Ile Glu Val Leu Glu
        50                  55                  60

Gly Asn Glu Gln Phe Ile Asn Ala Ala Lys Ile Ile Arg His Pro Gln
65                  70                  75                  80

Tyr Asp Arg Lys Thr Leu Asn Asn Asp Ile Met Leu Ile Lys Leu Ser
                85                  90                  95

Ser Arg Ala Val Ile Asn Ala Arg Val Ser Thr Ile Ser Leu Pro Thr
            100                 105                 110

Ala Pro Pro Ala Thr Gly Thr Lys Cys Leu Ile Ser Gly Trp Gly Asn
        115                 120                 125

Arg Lys Asp Phe Trp Thr Ala Ser Ser Gly Ala Asp Tyr Pro Asp Glu
130                 135                 140

Leu Gln Cys Leu Asp Ala Pro Val Leu Ser Gln Ala Lys Cys Glu Ala
145                 150                 155                 160

Ser Tyr Pro Gly Lys Ile Thr Ser Asn Met Phe Cys Val Gly Phe Leu
                165                 170                 175

Glu Gly Gly Lys Asp Ser Cys Gln Gly Asp Ser Gly Gly Pro Val Val
            180                 185                 190

Cys Asn Gly Gln Leu Gln Gly Val Val Ser Trp Gly Asp Gly Cys Ala
        195                 200                 205

Gln Lys Asn Lys Pro Gly Val Tyr Thr Lys Val Tyr Asn Tyr Val Lys
    210                 215                 220

Trp Ile Lys Asn Thr Ile Ala Ala Asn Ser
225                 230

<210> SEQ ID NO 75
<211> LENGTH: 234
<212> TYPE: PRT
<213> ORGANISM: artificial sequence
<220> FEATURE:
<223> OTHER INFORMATION: artificial sequence

<400> SEQUENCE: 75

Ile Val Gly Gly Tyr Asn Cys Glu Glu Asn Ser Val Pro Tyr Gln Val
1               5                   10                  15

Ser Leu Asn Ser Gly Tyr His Phe Cys Gly Gly Ser Leu Ile Asn Glu
            20                  25                  30

Gln Trp Val Val Ser Ala Gly His Cys Tyr Ala Ala Phe Asn Gly Lys
        35                  40                  45

Ser Arg Ile Gln Val Arg Leu Gly Glu His Asn Ile Gly Val Leu Glu
    50                  55                  60

Gly Asn Glu Gln Phe Ile Asn Ala Ala Lys Ile Ile Arg His Pro Gln
65                  70                  75                  80

Tyr Asp Trp Lys Thr Leu Asn Asn Asp Ile Met Leu Ile Lys Leu Ser
                85                  90                  95

Ser Arg Ala Val Ile Asn Ala Arg Val Ser Thr Ile Ser Leu Pro Thr
            100                 105                 110

Ala Pro Pro Ala Thr Gly Thr Lys Cys Leu Ile Ser Gly Trp Gly Asn
        115                 120                 125

Arg Lys Asp Phe Trp Thr Ala Ser Ser Gly Ala Asp Phe Pro Asp Glu
130                 135                 140

Leu Gln Cys Leu Asp Ala Pro Val Leu Ser Gln Thr Lys Cys Glu Ala
```

```
                145                 150                 155                 160
Ser Tyr Pro Gly Lys Ile Thr Ser Asn Met Phe Cys Val Gly Phe Leu
                    165                 170                 175

Glu Gly Gly Lys Asp Ser Cys Gln Gly Asp Ser Gly Pro Val Val
                180                 185                 190

Arg Asn Gly Gln Leu Gln Gly Val Val Ser Trp Gly Asp Gly Cys Ala
            195                 200                 205

Gln Lys Asn Lys Pro Gly Val Tyr Thr Lys Val Tyr Asn Tyr Val Lys
    210                 215                 220

Trp Ile Lys Asn Thr Ile Ala Ala Asn Ser
225                 230

<210> SEQ ID NO 76
<211> LENGTH: 12
<212> TYPE: PRT
<213> ORGANISM: artificial sequence
<220> FEATURE:
<223> OTHER INFORMATION: substrate A

<400> SEQUENCE: 76

Leu Leu Trp Leu Gly Arg Val Val Gly Gly Pro Val
1               5                   10

<210> SEQ ID NO 77
<211> LENGTH: 12
<212> TYPE: PRT
<213> ORGANISM: artificial sequence
<220> FEATURE:
<223> OTHER INFORMATION: substrate B

<400> SEQUENCE: 77

Lys Lys Trp Leu Gly Arg Val Pro Gly Gly Pro Val
1               5                   10

<210> SEQ ID NO 78
<211> LENGTH: 6
<212> TYPE: PRT
<213> ORGANISM: artificial sequence
<220> FEATURE:
<223> OTHER INFORMATION: variant1 SDR1

<400> SEQUENCE: 78

Asp Ala Val Gly Arg Asp
1               5

<210> SEQ ID NO 79
<211> LENGTH: 6
<212> TYPE: PRT
<213> ORGANISM: artificial sequence
<220> FEATURE:
<223> OTHER INFORMATION: variant2 SDR1

<400> SEQUENCE: 79

Asn Gly Arg Asp Leu Glu
1               5

<210> SEQ ID NO 80
<211> LENGTH: 6
<212> TYPE: PRT
<213> ORGANISM: artificial sequence
<220> FEATURE:
<223> OTHER INFORMATION: variant3 SDR1

<400> SEQUENCE: 80
```

```
Gly Phe Val Met Phe Asn
1               5

<210> SEQ ID NO 81
<211> LENGTH: 5
<212> TYPE: PRT
<213> ORGANISM: artificial sequence
<220> FEATURE:
<223> OTHER INFORMATION: variant1 SDR2

<400> SEQUENCE: 81

Arg Val His Pro Ser
1               5

<210> SEQ ID NO 82
<211> LENGTH: 5
<212> TYPE: PRT
<213> ORGANISM: artificial sequence
<220> FEATURE:
<223> OTHER INFORMATION: variant2 SDR2

<400> SEQUENCE: 82

Val Arg Gly Thr Trp
1               5

<210> SEQ ID NO 83
<211> LENGTH: 5
<212> TYPE: PRT
<213> ORGANISM: artificial sequence
<220> FEATURE:
<223> OTHER INFORMATION: variant3 SDR2

<400> SEQUENCE: 83

Arg Ser Pro Leu Thr
1               5

<210> SEQ ID NO 84
<211> LENGTH: 6
<212> TYPE: PRT
<213> ORGANISM: artificial sequence
<220> FEATURE:
<223> OTHER INFORMATION: variant a SDR1

<400> SEQUENCE: 84

Arg Pro Trp Asp Pro Ser
1               5

<210> SEQ ID NO 85
<211> LENGTH: 6
<212> TYPE: PRT
<213> ORGANISM: artificial sequence
<220> FEATURE:
<223> OTHER INFORMATION: variant b SDR1

<400> SEQUENCE: 85

Gly Phe Val Met Phe Asn
1               5

<210> SEQ ID NO 86
<211> LENGTH: 6
<212> TYPE: PRT
<213> ORGANISM: artificial sequence
<220> FEATURE:
<223> OTHER INFORMATION: variant c SDR1

<400> SEQUENCE: 86

Glu Ile Ala Asn Arg Glu
```

```
<210> SEQ ID NO 87
<211> LENGTH: 6
<212> TYPE: PRT
<213> ORGANISM: artificial sequence
<220> FEATURE:
<223> OTHER INFORMATION: variant d SDR1

<400> SEQUENCE: 87

Lys Ala Val Val Gly Thr
1               5

<210> SEQ ID NO 88
<211> LENGTH: 6
<212> TYPE: PRT
<213> ORGANISM: artificial sequence
<220> FEATURE:
<223> OTHER INFORMATION: variant e SDR1

<400> SEQUENCE: 88

Val Asn Ile Met Ala Ala
1               5

<210> SEQ ID NO 89
<211> LENGTH: 6
<212> TYPE: PRT
<213> ORGANISM: artificial sequence
<220> FEATURE:
<223> OTHER INFORMATION: variant f SDR1

<400> SEQUENCE: 89

Ala Ala Phe Asn Gly Asp
1               5

<210> SEQ ID NO 90
<211> LENGTH: 5
<212> TYPE: PRT
<213> ORGANISM: artificial sequence
<220> FEATURE:
<223> OTHER INFORMATION: variant a SDR2

<400> SEQUENCE: 90

Val His Pro Thr Ser
1               5

<210> SEQ ID NO 91
<211> LENGTH: 5
<212> TYPE: PRT
<213> ORGANISM: artificial sequence
<220> FEATURE:
<223> OTHER INFORMATION: variant b SDR2

<400> SEQUENCE: 91

Arg Ser Pro Leu Thr
1               5

<210> SEQ ID NO 92
<211> LENGTH: 5
<212> TYPE: PRT
<213> ORGANISM: artificial sequence
<220> FEATURE:
<223> OTHER INFORMATION: variant c SDR2

<400> SEQUENCE: 92

Arg Gly Ala Arg Thr
1               5
```

```
<210> SEQ ID NO 93
<211> LENGTH: 5
<212> TYPE: PRT
<213> ORGANISM: artificial sequence
<220> FEATURE:
<223> OTHER INFORMATION: variant d SDR2

<400> SEQUENCE: 93

Arg Thr Pro Ile Ser
1               5

<210> SEQ ID NO 94
<211> LENGTH: 5
<212> TYPE: PRT
<213> ORGANISM: artificial sequence
<220> FEATURE:
<223> OTHER INFORMATION: variant e SDR2

<400> SEQUENCE: 94

Thr Thr Ala Arg Lys
1               5

<210> SEQ ID NO 95
<211> LENGTH: 5
<212> TYPE: PRT
<213> ORGANISM: artificial sequence
<220> FEATURE:
<223> OTHER INFORMATION: variant f SDR2

<400> SEQUENCE: 95

Arg Lys Asp Phe Trp
1               5

<210> SEQ ID NO 96
<211> LENGTH: 157
<212> TYPE: PRT
<213> ORGANISM: Homo sapiens

<400> SEQUENCE: 96

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Leu Phe
    130                 135                 140

Ala Glu Ser Gly Gln Val Tyr Phe Gly Ile Ile Ala Leu
145                 150                 155
```

```
<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 1
<223> OTHER INFORMATION: Xaa can be Leu, Ile, Val of Phe
<220> FEATURE:
<221> NAME/KEY: VARIANT
<222> LOCATION: 2
<223> OTHER INFORMATION: Xaa can be any amino acid

<400> SEQUENCE: 97

Xaa Xaa Pro Arg Asn Ala
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 98

Cys Pro Gly Arg Val Val Gly Gly
1               5

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 99

Asp Asp Asp Lys
1

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 100

Ala Gly Gly Gly
1

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 101

Gly Val Gly Gly
1

<210> SEQ ID NO 102
```

```
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 102

Gly Gly Leu Gly
 1

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 103

Gly Gly Gly Ile
 1

<210> SEQ ID NO 104
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 104

Ala Gly Gly Gly
 1

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 105

Val Gly Gly Gly
 1

<210> SEQ ID NO 106
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 106

Leu Gly Gly Gly
 1

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 107
```

-continued

Ile Gly Gly Gly
1

<210> SEQ ID NO 108
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 108

Ala Arg Leu Thr
1

<210> SEQ ID NO 109
<211> LENGTH: 12
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 109
gcgcgcctta cc                                                         12

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 110

Ala Arg Leu Thr
1

<210> SEQ ID NO 111
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 111

Val Pro Gly Ser
1

<210> SEQ ID NO 112
<211> LENGTH: 12
<212> TYPE: DNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 2
<223> OTHER INFORMATION: n= c or t
<220> FEATURE:
<221> NAME/KEY: misc_feature
<222> LOCATION: 5
<223> OTHER INFORMATION: n = g or c
<220> FEATURE:
<221> NAME/KEY: misc_feature
<222> LOCATION: 7-8
<223> OTHER INFORMATION: n = g or t
<220> FEATURE:

-continued

```
<221> NAME/KEY: misc_feature
<222> LOCATION: 10
<223> OTHER INFORMATION: n = a or t

<400> SEQUENCE: 112
gngcncnngn cc                                                            12

<210> SEQ ID NO 113
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 1
<223> OTHER INFORMATION: Xaa can be Ala or Val
<220> FEATURE:
<221> NAME/KEY: VARIANT
<222> LOCATION: 2
<223> OTHER INFORMATION: Xaa can be Arg or Pro
<220> FEATURE:
<221> NAME/KEY: VARIANT
<222> LOCATION: 3
<223> OTHER INFORMATION: Xaa can be Leu, Gly, Val, or Trp
<220> FEATURE:
<221> NAME/KEY: VARIANT
<222> LOCATION: 4
<223> OTHER INFORMATION: Xaa can be Thr or Ser

<400> SEQUENCE: 113

Xaa Xaa Xaa Xaa
  1
```